(12) United States Patent
Pekoe et al.

(10) Patent No.: US 12,150,970 B2
(45) Date of Patent: Nov. 26, 2024

(54) COMPOSITION FOR TREATMENT OF TOPICAL DERMATOLOGICAL BACTERIAL SKIN CONDITIONS

(71) Applicant: ALPHYN BIOLOGICS, INC., Annapolis, MD (US)

(72) Inventors: Gary Michael Pekoe, Cincinnati, OH (US); Jazmyne Kristyne Mink, Cincinnati, OH (US); Steven Aaron Pentelnik, Cincinnati, OH (US); Neal G. Koller, Annapolis, MD (US); Daniel Banov, Sugar Land, TX (US); Zahraa I. Foraida, Pearland, TX (US)

(73) Assignee: Alphyn Biologics, Inc., Annapolis, MD (US)

( * ) Notice: Subject to any disclaimer, the term of this patent is extended or adjusted under 35 U.S.C. 154(b) by 322 days.

(21) Appl. No.: 17/680,970

(22) Filed: Feb. 25, 2022

(65) Prior Publication Data

US 2022/0265750 A1    Aug. 25, 2022

Related U.S. Application Data

(60) Provisional application No. 63/189,276, filed on May 17, 2021, provisional application No. 63/153,864, filed on Feb. 25, 2021.

(51) Int. Cl.
| | | |
|---|---|---|
| *A61K 36/47* | (2006.01) | |
| *A61K 45/06* | (2006.01) | |
| *A61P 17/00* | (2006.01) | |
| *A61P 31/04* | (2006.01) | |
| *A61P 31/00* | (2006.01) | |

(52) U.S. Cl.
CPC ............. *A61K 36/47* (2013.01); *A61K 45/06* (2013.01); *A61P 17/00* (2018.01); *A61P 31/04* (2018.01); *A61P 31/00* (2018.01)

(58) Field of Classification Search
CPC ...... A61K 36/47; A61K 45/06; A61K 9/0014; A61K 31/353; A61K 47/06; A61K 47/10; A61K 47/14; A61K 47/183; A61K 47/24; A61K 47/26; A61K 47/34; A61P 17/00; A61P 31/04; A61P 31/00
See application file for complete search history.

(56) References Cited

U.S. PATENT DOCUMENTS

| | | |
|---|---|---|
| 2002/0119997 A1 | 8/2002 | Bader et al. |
| 2008/0166426 A1 | 7/2008 | Pekoe |
| 2012/0190661 A1 | 7/2012 | Trogden et al. |
| 2016/0338973 A1 | 11/2016 | Sonti et al. |
| 2019/0021989 A1 | 1/2019 | Cantina et al. |

FOREIGN PATENT DOCUMENTS

| | | |
|---|---|---|
| WO | 2011024049 A2 | 3/2011 |
| WO | 2020058992 A1 | 3/2020 |
| WO | 2020191384 A1 | 9/2020 |

OTHER PUBLICATIONS

International Preliminary Report on Patentability for PCT/US2022/017922 dated Sep. 7, 2023.
International Search Report and Written Opinion for PCTUS2022017922 dated May 18, 2022.
Vilchez, et al. "Evaluation of the in vitro effect of Croton lechleri Latex "Grade Blood" versus Staphylococcus aureus. ATCC 25923" Knowledge for Development Jan.-Jun. 2018, 9(1): 129-136 w/English abstract.

*Primary Examiner* — Jessica Worsham
(74) *Attorney, Agent, or Firm* — DLA Piper LLP

(57) ABSTRACT

The present disclosure provides for a hydrogel formulation comprising a therapeutically effective amount of an extract of the *Croton lechleri* tree. The present disclosure also provides for a method of treating a dermatological condition in a subject via the topical administration of a hydrogel formulation comprising a therapeutically effective amount of an extract of the *Croton lechleri* tree.

56 Claims, 20 Drawing Sheets

COMPOSITION FOR TREATMENT OF TOPICAL DERMATOLOGICAL BACTERIAL SKIN CONDITIONS

CROSS-REFERENCE TO RELATED APPLICATIONS

This application claims the benefit of U.S. Provisional Application No. 63/153,864 filed Feb. 25, 2021 and U.S. Provisional Application No. 63/189,276 filed May 17, 2021. The disclosures of each of these applications are incorporated herein by reference.

SUMMARY

The present invention is generally related to a hydrogel formulation comprising a therapeutically effective amount of latex of *Croton lechleri*, preferably filtered latex of *Croton lechleri*, preferably filtered latex of *Croton lechleri* Müll.Arg., wherein the therapeutically effective amount contains at least the concentration of components of the reference standard. The concentration of components and performance standards of latex of *Croton lechleri*, preferably the concentration of components and performance standards of filtered latex of *Croton lechleri*, preferably the concentration of components and performance standards of filtered latex of *Croton lechleri* Müll.Arg of the reference standard are found in Tables 1a-e.

DEFINITIONS

Figure 1:
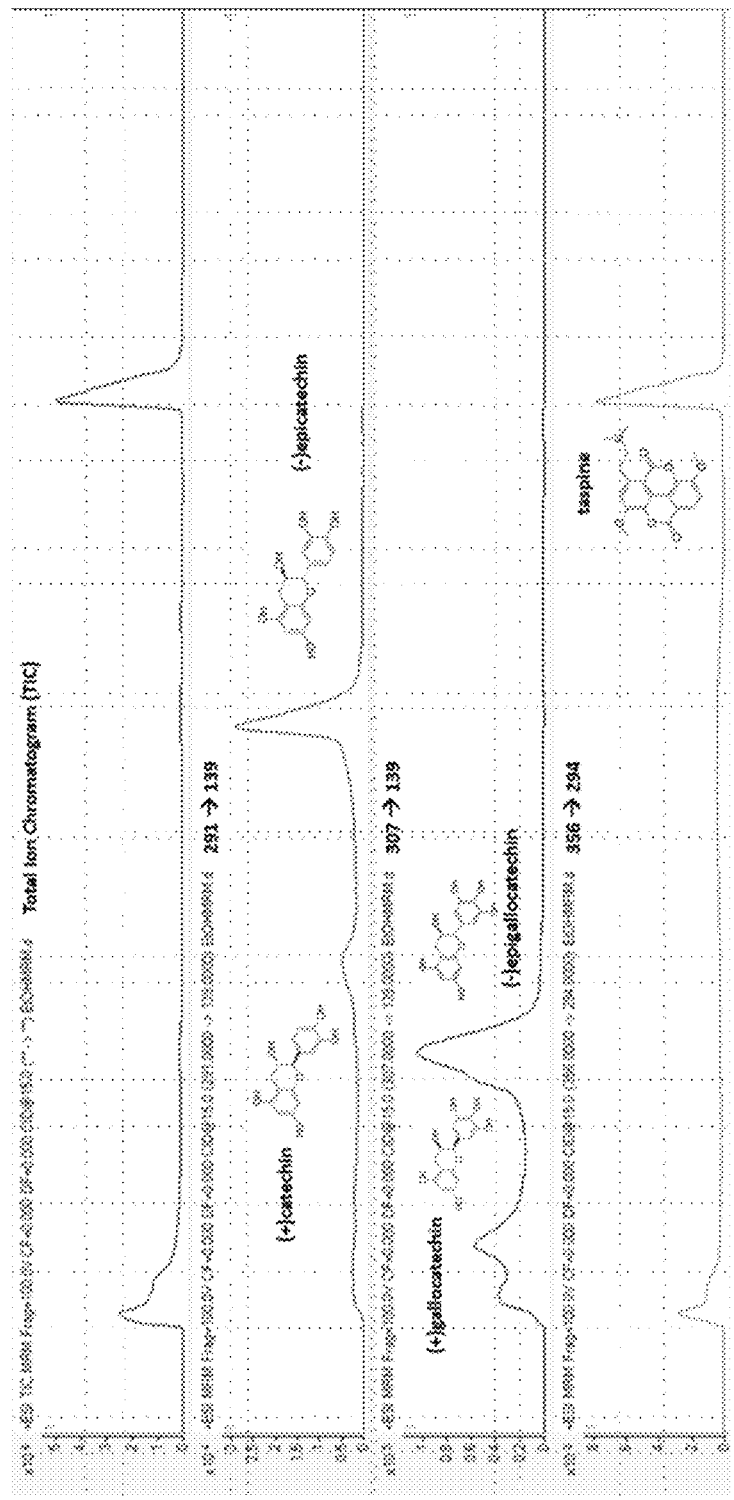
FIG. 1 depicts a representative Total Ion Chromatogram as well as additional Multiple Reaction Monitoring spectra that identify the marker compounds in an AB-101 composition.

Before the present compositions and methods are described, it is to be understood that this invention is not limited to the particular processes, compositions, or methodologies described, as these may vary. It is also to be understood that the terminology used in the description is for the purpose of describing the particular versions or embodiments only and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein are not entitled to antedate such disclosure by virtue of prior invention.

As used herein, the terms below have the meanings indicated.

It must also be noted that as used herein and in the appended claims, the singular forms "a," "an," and "the" include plural reference unless the context clearly dictates otherwise.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean plus or minus 10% of the numerical value of the number with which it is being used. Therefore, about 50% means in the range of 45%-55%.

As used herein, the term "AB-101" maybe used interchangeably with latex of *Croton lechleri*, preferably filtered latex of *Croton lechleri*, preferably filtered latex of *Croton lechleri* Müll.Arg. and botanical raw material. The latex is excreted material from the wounded trunk of *Croton lechleri*, preferably of *Croton lechleri* Müll.Arg. In all such instances the latex is the whole latex. In all such instances, the latex is unfractionated.

As used herein, the term "acute bacterial skin or skin structure infection" is defined as a bacterial infection of the skin including but not limited to bacterial skin infections, drug resistant bacterial skin infections or multi drug resistant bacterial skin infections. Additionally, such infections may be uncomplicated or complicated, mild or serious. Such infections may be without a lesion, abscess or wound (e.g., primary infections, such as all forms of impetigo including but not limited to Mupirocin-resistant impetigo), or with a lesion, abscess or wound. Additionally, such infections may be of any size, including those with a any lesion 75 cm2 or larger (often referred to as Acute Bacterial Skin and Skin Structure Infections (or ABSSSIs)) or lesser sized skin infections (often referred to as Secondarily Infected Traumatic Lesions (or SITLs), Skin and Soft Tissue Infections (or SSTIs).

"Administering" when used in conjunction with a therapeutic, such as AB-101, means to administer a therapeutic directly into or onto a target tissue or to administer a therapeutic to a patient whereby the therapeutic positively impacts the tissue to which it is targeted. Thus, as used herein, the term "administering", when used in conjunction with a composition of embodiments herein, can include, but is not limited to, providing the composition into or onto the target tissue; providing the composition to a patient by, e.g., topical application whereby the therapeutic reaches the target tissue. "Administering" a composition may be accomplished topically or in combination with other known techniques.

As used herein the term "cellulitis/erysipelas" is defined as a diffuse bacterial skin infection characterized by spreading areas of redness, edema, and/or induration.

The transitional term "comprising," which is synonymous with "including," "containing," or "characterized by," is inclusive or open-ended and does not exclude additional, unrecited elements or method steps.

In embodiments or claims where the term "comprising" is used as the transition phrase, such embodiments can also be envisioned with replacement of the term "comprising" with the terms "consisting of" or "consisting essentially of."

As used herein, the term "consists of" or "consisting of" means that the hydrogel formulation, pharmaceutical composition, composition or the method includes only the elements, steps, or ingredients specifically recited in the particular claimed embodiment or claim.

As used herein, the term "consisting essentially of" or "consists essentially of" means that the hydrogel formulation, or the method includes only the elements, steps or ingredients specifically recited in the particular claimed embodiment or claim and may optionally include additional elements, steps or ingredients that do not materially affect the basic and novel characteristics of the particular embodiment or claim. For example, the only active ingredient(s) in the composition or method that treats the specified condition (e.g., nutrient depletion) is the specifically recited therapeutic(s) in the particular embodiment or claim.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The terms "excipient" and "pharmaceutically acceptable excipient" as used herein are intended to be generally synonymous, and is used interchangeably with, the terms "carrier," "pharmaceutically acceptable carrier," "diluent," "pharmaceutically acceptable diluent."

As used herein, the term "extract" refers to the liquid that runs between the bark and the wood portions of the tree, which is and remains unfractionated.

As used herein the term "major cutaneous abscess" is defined as a bacterial infection characterized by a collection of pus within the dermis or deeper that is accompanied by redness, edema, and/or induration.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

As used herein, the term "pharmaceutically acceptable salt" refers to a salt prepared from a base or acid which is acceptable for administration to a patient, such as a mammal. The term "pharmaceutically acceptable salts" embraces salts commonly used to form alkali metal salts and to form addition salts of free acids or free bases. The nature of the salt is not critical, provided that it is pharmaceutically-acceptable. Such salts can be derived from pharmaceutically-acceptable inorganic or organic bases and from pharmaceutically-acceptable inorganic or organic acids.

As used in each of the embodiments here in, sap may be include among others sap, latex, resin, extract, or any combination of the foregoing.

As used herein, the term "therapeutic" or "therapeutic agent" or "pharmaceutically active agent" means an agent utilized to treat, combat, ameliorate, prevent or improve an unwanted condition or disease of a patient.

The term "therapeutically acceptable" refers to those compositions which are suitable for use in contact with the tissues of patients without undue toxicity, irritation, and allergic response, are commensurate with a reasonable benefit/risk ratio, and are effective for their intended use.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid.

The phrase "therapeutically effective" is intended to qualify the amount of active ingredients used in the treatment of a disease or disorder or on the effecting of a clinical endpoint.

A "therapeutically effective amount" or "effective amount" of a composition is a predetermined amount calculated to achieve the desired effect, i.e., to, inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per application will normally fall within the range of from 0.001 to 10 mg/kg, more usually in the range of from 0.01 to 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of the composition of this invention is typically an amount such that when it is administered in a physiologically tolerable excipient composition, it is sufficient to achieve an effective systemic concentration or local concentration in the tissue.

The terms "treat," "treated," "treating", or "treatment" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "topical" includes administering to any skin or mucosal surface or being suitable for such administration. In some embodiments, "topical" may be the skin surface. Skin surface includes any part of the body, including but not limited to face, hands, legs, neck, abdominal area, eyes, nose, and chest. Mucosal surface includes, without limitation, mucosa of the mouth or oral mucosa, lips, tongue, nasal, buccal mucosa, palate, gingiva, nasopharynx, respiratory epithelium, conjunctiva, vagina, cervix, and urethral mucosa.

As used herein, the term "wound" is defined as an injury to living tissue caused by a cut, blow, or other impact, typically one in which the skin is cut or broken.

As used herein the term "wound infection" is defined as a bacterial infection characterized by purulent drainage from a wound with surrounding redness, edema, pain, tenderness and/or induration.

Also provided are embodiments wherein any embodiment herein may be combined with any one or more of the other embodiments, unless otherwise stated and provided the combination is not mutually exclusive.

DETAILED DESCRIPTION

The chemical defenses of plants include complex mixtures of organic compounds and typically do not involve individual substances; these compounds appear in different concentrations (majority or minority) within various products derived from natural species. The biological activities of these products can be found to originate from their ability to interact among themselves and other substances through synergistic, additive, antagonistic effects—and can be optimized through the modification of the pharmacokinetics and/or pharmacodynamics of the component substances. The biological effects may occur from the interaction with all the organic compounds or by the interaction among certain components, which may present themselves as majority or minority. Accordingly, when described herein, AB101 consists of the whole latex obtained from the *Croton lechleri* tree—it is unfractionated—but is selected based upon the presence of select components that meet the reference standard as described herein.

In natural product research, the major compound's role and mechanism in its associated biological activity is commonly investigated. Thus, in the scientific literature, there are innumerous published studies where the major components have been found to be responsible for these activities. However, this disregards the possible interactions among the totality of compounds that may be present at lower concentrations in natural products. A study carried out with the essential oil *Thymus vulgaris* and its major constituent, thymol identified that the effect of the constituents of the oil was not phytotoxic to lettuce seeds, whereas the isolated action of thymol caused significant inhibitory effects on seed germination, raising the possibility of a partial inhibition of thymol activity by other components of the oil. Demonstrating the importance of considering the interactions among all components of the product.

For example, evaluation of the activity of the sap of *Dracaena cochinchinensis* and three active constituents regarding the analgesic activity from the inhibition of currents on the TRPV1 channel, induced by capsaicin. As a result, the authors found that the combination of the three active components of the sap is responsible for the analgesic activity of the species in question, where these components act synergistically, as the compounds found in greater concentration were not directly responsible for the biological activity found.

Another consideration regarding interactions among the active components of a natural product is the ability to alter the pharmacokinetics of the components when compared with the administration of these molecules in isolation. This can be achieved by modifying the absorption, distribution, metabolism and elimination profiles. A study reported the pharmacokinetic profile of chlorogenic acid and coryloin alone in comparison with the product formed by the hydroalcoholic extract of *Pharbitis nil* and *Corydalis tuber*, DA-9701, which contains the two components in equivalent concentrations. Results showed a significant increase in the AUC of coryloin when DA-9701 was administered compared with the two compounds in isolation, both orally. This increase in AUC can be explained by decreased hepatic and/or gastrointestinal first-pass metabolism compared with pure coryloin. In addition, there may be inhibition of corticosteroid presystemic metabolism by other components of DA-9701.

Another example is the complexity of metabolic pathways and the complexity of essential oils, extracts and herbal products may be directly related to the recorded biological effect. In a study with essential oil of *Eucalyptus tereticornis* and its major constituents, it was observed that all three major constituents reinforce the constricting effect of acetylcholine in the trachea of rats, however with a stimulus of potassium, the essential oil presents a relaxing effect, may be due to the inhibition of acetylcholinesterase activity.

*Croton lechleri* (a member of the family Euphorbiaceae, commonly called the spurge family) has approximately 1,300 species of plants that are either herbaceous (plants that have no persistent woody stem above ground), shrub (a woody plant which is smaller than a tree and has several main stems arising at or near the ground), tree (a perennial plant with an elongated stem, or trunk, supporting branches and leaves in most species), or liana (any of various long-stemmed, woody vines that are rooted in the soil at ground level and use trees, as well as other means of vertical support, to climb up to the canopy to get access to well-lit areas of the forest) forms. The *Croton* genus is a diverse and complex group of flowering plants ranging from herbs and shrubs to trees. The *Croton* genus is widely distributed in tropical and subtropical regions around the world.

Dragon's blood refers to a bright red resin that is obtained from different species of a number of distinct plant genus: *Croton, Dracaena, Daemonorops, Calamus rotang* and *Pterocarpus*. The red resin has been in continuous use since ancient times as varnish, medicine, incense, and dye. The name dragon's blood is used to refer to all of the above plant genus, often without any distinction as to the genus or species it is coming from. Those with the same genus will be similar in any therapeutic or nutritional value, with factors such as local soil, local rainfall, local humidity, local sunlight, local fauna and the like imparting variability and inconsistency. However, the difference between the red resin coming from *Croton* versus *Daemonorops* (a genus of rattan palms in the family Arecaceae found primarily in the tropics and subtropics of southeastern Asia with a few species extending into southern China and the Himalayas) will be significant. The *Croton* and *Daemonorops* genus originate from opposite sides of the world so their components are different and therefore specificity of source plant is important to deliver the desired medicinal benefits or avoid undesirable toxic results. For example milky white latex that is often toxic or at least irritating to the skin is common to the members of the spurge or Euphorbiaceae family. Therefore selecting the specific genus, species, and local geographical area of the spurge or Euphorbiaceae family is essential to having the possiblity for the latex to have specific and repetitive medicinal properties.

A handful of *Croton* species found in the South America rainforest (in countries of Bolivia, Brazil, Colombia, Ecuador and Peru) Central America and Mexico produce the red latex, commonly known as dragon's blood, that has medicinal properties. The dragon's blood trees grown in these areas include *Croton lechleri, Croton draco, Croton palanostigma, Croton sordidus, Croton urucurana,* and *Croton xalapenesis*.

In certain embodiments, the specific dragon's blood tree of the present application is *Croton lechleri* Müll.Arg. of the Family: Euphorbiaceae. Dragon's blood is also referred to as Sangre de drago (Peru), Sangre de grado (Ecuador).

While the desired medicinal properties could be found by extracting the compositions from either the leaves or bark, in preferred embodiments, it is the deep red latex of *Croton lechleri*, preferably filtered latex of *Croton lechleri*, preferably filtered latex of *Croton lechleri* Müll.Arg, wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard, that is also referred to as latex, that is utilized. According to Langenheim (2003) resin "is a lipid-soluble mixture of volatile and non-volatile terpenoid and/or phenolic secondary compounds that are usually secreted in specialized structures located either internally or on the surface of the plant and are of potential significance in ecological interactions". By contrast, latex, is a mixture of terpenoids, phenolic compounds, acids, carbohydrates, etc. having a protective role (Lewisohn 1991) and produced in special cells called laticifers (Fahn 1979). Chemical characterization of dragon's blood is species specific and has been undertaken by many authors. For example, it is possible to distinguish between dragon's blood from some individual species used in works of art, since it has been sold as a colorant for many centuries (Baumer and Dietemann 2010). Dragon's blood of *Croton* spp. is usually referred to as latex due to the fact that it is secreted and stored by laticifers, and its major constituents are polymeric anthocyanidins, which co-occur with many minor constituents, including diterpenes and simple phenols (Salatino et al. 2007). Dragon's blood secreted by stems of *Pterocarpus officinalis* is also called latex (Weaver 1997; Guerrero and Guzman 2004); however, information about the chemical composition of the exudate and its ecological function is poorly known. Dragon's blood derived from species of *Dracaena* and *Daemonorops* is a phenolic resin (Langenheim 2003), with well-recognized chemical content (e.g. Gonzalez et al. 2000; Shen et al. 2007; Sousa et al. 2008). Sometimes, dragon's blood is referred to as latex (e.g. Philipson 2001). However, this could prove to be a source of confusion, since plants produce other exudates referred to by that name, such as xylem latex and phloem latex, which are entirely different in terms of their location, chemical composition and function. The resin is obtained through tapping the tree or other common draining methods. Draining the tree latex has the additional benefit of not having to use complex and costly extraction technology to obtain the desired composition from either the leaves or bark. The latex of *Croton lechleri* Müll.Arg. of the present application is then filtered in a 30 micron filter to remove plant debris and thick, resinous material. Chemical characterization of dragon's blood is local geography specific and has not been undertaken by prior authors.

Medicinal and toxic properties of various species of the *Croton* genus have been ascribed to a wide variety of chemical compounds, such as terpenoids and steroids, alkaloids, and phenolic compounds, the latter including predominantly flavonoids, lignans, and proanthocyanidins. Some embodiments of the present application utilize the whole latex, thereby leveraging the "organic" synergy of all the latex components as intended by nature. The molecular classes found in latex of *Croton lechleri* Müll.Arg. of the present application which provide the desired medicinal benefits of *Croton lechleri* Müll.Arg. are: Alkaloids, Diterpenes, Lignins, Phenols, Phytosterols, Proanthocyanidins, Sterols and Tannins.

A hydrogel formulation needs to have a safety profile for use in topical applications where the composition has low systemic blood absorption (i.e. passage into the blood stream) and where the composition that is absorbed has a low partition coefficient as measured by Log P. The Log P represents the concentration of solute in the organic and aqueous partition. A low Log P means a higher partition or concentration in the aqueous solute. This is desirable from a safety standpoint. A higher Log P indicates the composition is more likely to absorbed and retained in the body via organs and tissues, while lower Log P indicates higher safety via the composition would be natural eliminated, not absorbed or retained that could lead to build up of toxic compounds.

AB-101 uses the unique composition of the entire latex of the *Croton lechleri* Arg. The novelty of this invention is identifying the pharmaceutical AB-101 composition that has all the performance properties listed above to treat a dermatological condition, and promote healing with the appropriate safety profile. This represents a complex multivariant solution that optimizes multiple performance properties where the solution is not obvious to one familiar with the art.

In the embodiments disclosed herein, the latex of *Croton lechleri*, preferably filtered latex of *Croton lechleri*, preferably filtered latex of *Croton lechleri* Müll.Arg, that is utilized is not fractionated, but does contain at least the concentration of certain components and performance standards of the reference standard as set forth in Tables 1a-e.

AB-101 is a novel first-in-class of a new class of broad spectrum topical antibiotics called Multi-Target Therapeutics (MTT). The AB-101 platform utilizes the latex from the *Croton lechleri* Müll.Arg tree that is native and ubiquitous to the Amazonian forest. The extract and therefore AB-101 Botanical Drug Substance (BDS) has multiple bioactive compounds.

Common dermatological skin conditions that need new and novel medical solutions include the treatment of skin and skin structure infections (SSSIs), also referred to as skin and soft tissue infections (SSTIs), or acute bacterial skin and skin structure infections (ABSSSIs). The pathogen involved has most frequently been a bacterial species and as such, these infections require treatment by antibiotics. These skin infections can be either be acute or chronic, primary or secondary.

Some of the common dermatological conditions but not limited to include Atopic Dermatitis (AD), also known as atopic eczema or eczema, Impetigo and infections associated with complication of Epidermolysis Bullosa (EB). These are examples where bacterial pathogens can be the primary source of the skin ailment or associated as a secondary complication. In all cases, a topical treatment to address the skin ailment of the bacterial pathogen is the focus of the composition for pharmaceutical grade of AB-101.

The need for more effective antibiotics is traced to the problem that current antibiotic treatments have developed bacterial resistance. This is a problem for the two most commonly used topical antibiotics; mupirocin and fusidic acid. Increased mupirocin use predisposes to mupirocin resistance, which is significantly associated with persistent MRSA carriage. Mupirocin resistance as high as 81% has been reported. (T. Poovelikunnel et al. Mupirocin resistance: clinical implications and potential alternatives for the eradication of MRSA. J Antimicrob Chemother 2015; 70: 2681-2692 doi:10.1093/jac/dkv169 Advance Access publication 3 Jul. 2015) Antibiotic resistance is a significant problem both in hospitals and the community. Topical antibiotics are widely used for dermatological problems and this may be leading to the emergence of resistant bacteria. (M Shah et al. High levels of fusidic acid-resistant *Staphylococcus aureus* in dermatology patients. Br J Dermatol. 2003 May; 148(5): 1018-20. doi: 10.1046/j.1365-2133.2003.05291.x.) Shah shows 50% of *S. aureus* isolates from dermatology patients were resistant to fusidic acid. This figure rose to 78% in patients with atopic eczema. Of patients with fusidic acid-resistant *S. aureus* isolates, 96% had used a fusidic acid-containing preparation within the previous 6 months. The level of fusidic acid resistance in *S. aureus* samples cultured from non-dermatology patients was only 9.6%, a level significantly below that for dermatology patients (P<0.001).

Eczema (infected and non-infected): The publication by Ogonowska, including the many scholars he cites, illuminates the role of the pathogen *Staphylococcus aureus* contributes to the exacerbating of eczema. (Ogonowska et al. Colonization with *Staphylococcus aureus* in Atopic Dermatitis Patients: Attempts to Reveal the Unknown. Frontiers in Microbiology. January 2021. Volume 11. Article 567090. doi: 10.3389/fmicb.2020.567090.eCollection 2020). Some of the key problems highlighted by Ogonowska for treating AD/Eczema include:

Chronic and relapsing inflammatory skin disorder. Nevertheless, it can persist or appear during puberty and adulthood. AD occurs commonly in 15-30% of children and 2-10% of adults worldwide.

Patients are massively colonized with *Staphylococcus aureus* (*S. aureus*) in lesional and non-lesional skin. A skin infection may become systemic if left untreated. Of interest, the incidence of multi-drug resistant *S. aureus* (MRSA) in AD patients is higher as compared to a healthy population, which makes treatment even more challenging.

High *S. aureus* colonization rate is observed in both groups, children and adults. Colonization rate increases with the severity of the AD, and it acts as an aggravating factor exacerbating inflammation.

Among *S. aureus* isolates, methicillin-resistant *S. aureus* (MRSA) constitutes an important and significant group that requires particular concern. MRSA is a group of strains that are resistant to multiple β-lactam antibiotics (cephalosporins, carbapenems, monobactams, and penicillins). This phenotype results in limited treatment options, including for skin infections. It has been demonstrated that among *S. aureus* strains colonizing AD patients, the percentage of MRSA is 4-13 times higher than in a healthy population.

Colonization with MRSA constitutes the best-known risk factor for developing infection and MRSA can be easily transferred via direct skin-to-skin contact in the public settings, e.g., gyms, thus spreading the bacteria further.

One of the main factors predisposing to the *S. aureus* colonization are changes in the composition of lipids and fatty acids in the skin. In the epidermis (especially in the stratum corneum) significantly lower level of ceramides and higher amount of cholesterol was observed. The reduction of skin lipids level could explain the role of these components in maintaining the hydration of the skin.

In order to restore the proper barrier function of the damaged skin, it is essential to maintain the disturbed hydration of the epidermis. To this end, moisturizers containing emollients and humectants have been shown to reduce itching, flares and even reduce the necessity of anti-inflammatory drugs.

Impetigo (infected and non-infected): Impetigo is the most common bacterial infection in children. This acute, highly contagious infection of the superficial layers of the epidermis is primarily caused by *Streptococcus pyogenes* or *Staphylococcus aureus*. Secondary skin infections of existing skin lesions (eg, cuts, abrasions, insect bites, chickenpox) can also occur. (Moulin F, Quinet B, Raymond J, Gillet Y, Cohen R. Managing children skin and soft tissue infections. *Arch Pediatr.* 2008 Oct. 15 Suppl 2:S62-7) These infections are inclusive of Methicillin-resistant *S aureus* (MRSA) (Moran G J, Amii R N, Abrahamian F M, Talan D A. Methicillin-resistant *Staphylococcus aureus* in community-acquired skin infections. *Emerg Infect Dis.* 2005 Jun. 11(6):928-30). Impetigo is classified as either nonbullous (impetigo contagiosa) (about 70% of cases) or bullous, as shown in the image below (Cole C, Gazewood J. Diagnosis and treatment of impetigo. *Am Fam Physician.* 2007 Mar. 15. 75(6):859-64).

While the topical antibiotics such as mupirocin and fusidic acid are commonly prescribed there is a growing concern that they are contributing to antimicrobial resistance Epidermolysis Bullosa: EB is a rare genetic connective tissue disorder that affects 1 out of every 20,000 births in the United States (approximately 200 children a year are born with EB). There are many genetic and symptomatic variations of EB, but all share the prominent symptom of extremely fragile skin that blisters and tears from minor friction or trauma. The list of complications and secondary illnesses can be long and requires multiple interventions from a range of medical specialists. EB affects all genders and racial and ethnic groups equally.

Patients with the genetic blistering disease epidermolysis bullosa (EB) often have chronic wounds that can become colonized by different bacteria, especially the opportunistic pathogen *Staphylococcus aureus*. We therefore determined the *S. aureus* colonization rates in EB patients from the Netherlands by collecting swabs from their anterior nares, throats and wounds. Within a period of ~2 years, more than 90% of the sampled chronic wounds of EB patients were found to be colonized by *S. aureus*. Molecular typing revealed that EB patients were not colonized by a single *S. aureus* type. Rather the *S. aureus* population structure in the sampled EB patients mirrored the local *S. aureus* population structure within the Netherlands. (Magdalena M. van der Kooi-Pola et al, Host-pathogen interactions in epidermolysis bullosa patients colonized with *Staphylococcus aureus*, J Med Microbiol. 2014 March; 304(2):195-203)

While EB is a more serious and yet a more limited dermatological skin disease than either Eczema or Impetigo, they have a commonality in the need to fight bacterial infections. Treatment with a topical antibiotic, specifically one that is very effective with *S. aureus*, MRSA *S. pyogenes* can be effective in helping to treat infections across all three of these life-threatening skin diseases.

Psoriasis is a skin disease that causes red, itchy scaly patches, most commonly on the knees, elbows, trunk and scalp. As defined by the Mayo Clinic, psoriasis is a common, long-term (chronic) disease with no cure. Most types of psoriasis go through cycles, flaring for a few weeks or months, then subsiding for a time or even going into remission. Psoriasis signs and symptoms can vary from person to person. Common signs and symptoms include: 1. Red patches of skin covered with thick, silvery scales, 2. small scaling spots (commonly seen in children), 3. dry, cracked skin that may bleed or itch, 4. Itching, burning or soreness, 5. thickened, pitted or ridged nails and 6. swollen and stiff joints. Psoriasis patches can range from a few spots of dandruff-like scaling to major eruptions that cover large areas. The most commonly affected areas are the lower back, elbows, knees, legs, soles of the feet, scalp, face and palms.

As reported by S. Lafi et. al. secondary bacterial invaders complicate psoriasis lesions. Such infections can progress rapidly and can be seriously life-threatening. Hassan studied the current prevalence of the secondary bacterial infections in psoriasis and also highlighted the emerging trend associated with antibacterial resistance. (Lafi, S., Hasan, A., Al-Alowssi, M. (2010). Secondary Bacterial Infections Complicating Psoriasis. Egyptian Academic Journal of Biological Sciences, G. Microbiology, 2(2), 37-42).

In another study conducted by Eva Marcus, it was shown that nearly half of the patients examined had colonization of the psoriasis plaques with pathogenic bacteria. Examinations of the bacterial flora in psoriasis concentrated on the proof of *Staphylococcus aureus* and found a prevalence of up to 64% in lesional skin of patients with plaque psoriasis. Corresponding to this, *Staphylococcus aureus* has also been found as the most prevalent bacterium in patients with superinfected pustular psoriasis. In this study 31% of the bacteria were gram-positive and 9% were gram-negative. (Marcus, E., Demmler, D., Rudolph, A., & Fischer, M. (2011). Bacterial colonization of psoriasis plaques. Is it relevant? Dermatology reports, 3(2)).

AB-101 is an important topical treatment to reduce and cure the symptoms of psoriasis. *Staphylococcus aureus* is the most common pathogen isolated in psoriasis lesions which AB-101 has been shown to be extremely effective. Further, with the rise of multi-drug resistance, especially with *S. aureus* the presence of MRSA will also be on the rise. Having gram-negative efficacy can also contribute to a positive role for AB-101. Having a new MDR topical treatment for secondary bacterial invaders to prevent the occurrence of a deadly systemic infection present AB-101 as an excellent antibiotic treatment for psoriasis.

Pathogen colonization is an important skin condition to be addressed as detailed by Sunhyo Ryu (S. Ryu, P. I. Song, C. H. Seo, H. Cheong and Y. Park, Colonization and Infection of the Skin by *S. aureus*: Immune System Evasion and the Response to Cationic Antimicrobial Peptides, Int. J. Mol. Sci. 2014, 15, 8753-8772). Colonizing pathogens primarily relate to *S. aureus* and MRSA and AB-101 is an effective and novel treatment for these pathogens.

Ryu details the causes, mechanism and risks associated with colonized *S. aureus* and MRSA. Specifically, *S. aureus* is a widespread cutaneous pathogen responsible for the great majority of bacterial skin infections in humans. The incidence of skin infections by *S. aureus* reflects in part the competition between host cutaneous immune defenses and *S. aureus* virulence factors. *S. aureus* can live as a commensal organism on the skin and in the nose and throat. Approximately 30% of healthy people are asymptomatically colonized by *S. aureus*, which permanently colonizes the anterior nares in 10%-20% of the population and intermittently colonizes 30%-50%; the rest of the population never becomes colonized. Importantly, this colonization is a known risk factor for infection, and *S. aureus* causes a range of infections, from minor skin infections to abscesses, endocarditis and sepsis, and is a leading cause of nosocomial infections, as colonized healthcare workers can transmit the pathogen to immunosuppressed patients. In addition, several cases of community-acquired methicillin-resistant *S. aureus* (CA-MRSA) infections have been recently reported. Notably, these reports describe severe and even lethal infections by highly virulent strains of *S. aureus* in immunocompetent individuals.

MRSA infections are caused by strains of *S. aureus* that have become resistant to the antibiotics commonly used to treat ordinary infections. Most MRSA infections occur in people who have been in hospitals or other health care settings, such as nursing homes and dialysis centers. When it occurs in these settings, it is known as health care-associated MRSA (HA-MRSA). HA-MRSA infections are typically associated with invasive procedures or devices, such as surgeries, intravenous tubing or artificial joints. However, another type of MRSA infection occurs in the wider community, among otherwise healthy individuals. This form, community-associated MRSA (CA-MRSA) is spread by skin-to-skin contact. It often begins as a painful skin boil and generally causes skin and soft tissue infections, but it is also capable of causing invasive disease such as endocarditis, necrotizing pneumonia and sepsis HA-MRSA, by contrast, is considered a nosocomial pathogen typically associated with invasive disease, such as bloodstream infections, pneumonia, surgical site infections and urinary tract infections.

AB-101 with its MTT is a novel and critical antibiotic to address colonizing *S. aureus* and MRSA as it is associated with a disorder caused by *S. aureus* and MRSA nasal or ear passage, as a wash prior to surgery to prevent SSTI or the occurrence of sepsis in any other applications for those familiar with the art associated with conditions that can prevent the spread and elimination of colonizing *S. aureus* and MRSA.

AB-101 is an effective treatment for wounds including superficial cut/scraps, abrasions and chronic infected conditions. Chronic infection and wounds include but not limited to diabetic ulcers, arterial ulcers, venous ulcers, mixed arterial and venous ulcers and decubitus ulcers. Those familiar of these infections and wounds and skilled in the art are well aware that they are infected by gram-positive pathogens associated with *Staphylococcus aureus* (*S. aureus*), methicillin-resistant *Staphylococcus aureus* (MRSA), *Streptococcus pyogenes* (*S. pyogenes*) and the gram-negative pathogen of *Pseudomonas aeruginosa* (*P. aeruginosa*). Further, chronic wounds are very complex and hard to heal. Killing the bacteria is a critical element to enabling the healing process. The fact that AB-101 has efficacy against both gram-positive and gram-negative pathogens provides unique efficacy for a drug compound, along with AB-101's MTT properties.

Taken in total, AB-101 is a novel first-in-class of a new class of broad spectrum topical antibiotics called Multi-Target Therapeutics (MTT). The extract AB-101 Botanical Drug Substance (BDS) has multiple bioactive compounds making it a very effective antibiotic ideally suited for treating topical skin infections. The summary of indications AB-101 is effective against along with the associated pathogens causing the SSTI and wound infections and detailed ailments are shown in Table A.

TABLE A

| Topical Indication* | Pathogen* |
|---|---|
| Impetigo | *S. aureus*, MRSA, MRSA resistant to mupirocin, *S. pyogenes* |
| Atopic dermatitis | *S. aureus*, MRSA, MRSA resistant to mupirocin |
| Epidermolysis bullosa | *S. aureus*, MRSA, MRSA resistant to mupirocin, *S. pyogenes* and *P. aeruginosa* |
| Psoriasis | *S. aureus*, MRSA, MRSA resistant to mupirocin, |

TABLE A-continued

| Topical Indication* | Pathogen* |
|---|---|
| Skin colonized with pathogens | *S. aureus*, MRSA, MRSA resistant to mupirocin |
| Wounds | *S. aureus*, MRSA, MRSA resistant to mupirocin, *S. pyogenes* and *P. aeruginosa* |

*Included and not limited to those skilled in the art.

AB-101 has demonstrated a unique safety profile that unexpectedly based on its physical properties enables maximizing drug delivery, while also increasing the safety profile. This unexpectant finding goes against the common understanding, to those familiar in the art. It is common convention to one familiar with the art the expectation to formulate a drug to be safe and effective, the dose needs to be as low as possible while delivering the desired efficacy. This is exactly opposite for AB-101. By maximizing the dose delivery, safety is also synergistically maximized as well. This combined with the fact that any lipophilic components of AB-101 would likely be absorbed by the skin leaving only hydrophilic components being available for bloodstream absorption. This would result in any AB-101 absorbed into the bloodstream to be naturally and readily eliminated through normal body functions. Systemic absorption would also be negligible, reducing any safety risks. This makes AB-101 a very potent and an extremely effective antibiotic designed to treat SSTI topical skin conditions.

Some embodiments herein are directed to a method of identifying a composition of latex of *Croton lechleri*, preferably a composition of filtered latex of *Croton lechleri*, preferably a composition of filtered latex of *Croton lechleri* Müll.Arg comprising: (a) determining the concentration of components of latex of *Croton lechleri*, preferably the concentration of components of filtered latex of *Croton lechleri*, preferably the concentration of components of filtered latex of *Croton lechleri* Müll.Arg; (b) comparing the concentrations of the components to the concentrations of the components of a reference standard; and (c) identifying a composition of latex of *Croton lechleri*, preferably a composition of filtered latex of *Croton lechleri*, preferably a composition of filtered latex of *Croton lechleri* Müll.Arg, wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard.

Some embodiments herein are directed to a method of identifying a composition of latex of *Croton lechleri*, preferably a composition of filtered latex of *Croton lechleri*, preferably a composition of filtered latex of *Croton lechleri* Müll.Arg for use in treating a dermatological condition in a subject comprising: (a) determining the concentration of components of latex of *Croton lechleri*, preferably the concentration of components of filtered latex of *Croton lechleri*, preferably the concentration of components of filtered latex of *Croton lechleri* Müll.Arg; (b) comparing the concentrations of the components to the concentrations of the components of a reference standard; and (c) identifying a composition of latex of *Croton lechleri*, preferably a composition of filtered latex of *Croton lechleri*, preferably a composition of filtered latex of *Croton lechleri* Müll.Arg for use in treating a dermatological condition in a subject, wherein the composition contains at least the concentration of components of latex of *Croton lechleri*, preferably the concentration of components of filtered latex of *Croton*

*lechleri*, preferably the concentration of components of filtered latex of *Croton lechleri* Müll.Arg of the reference standard.

Some embodiments herein are directed to a method of identifying a composition of latex of *Croton lechleri*, preferably a composition of filtered latex of *Croton lechleri*, preferably a composition of filtered latex of *Croton lechleri* Müll.Arg for use in treating or preventing or reducing the risk of a dermatological condition comprising: (a) determining the concentration of components of latex of *Croton lechleri*, preferably the concentration of components of filtered latex of *Croton lechleri*, preferably the concentration of components of filtered latex of *Croton lechleri* Müll.Arg; (b) comparing the concentrations of the components to the concentrations of the components of a reference standard; and (c) identifying a composition of latex of *Croton lechleri*, preferably a composition of filtered latex of *Croton lechleri*, preferably a composition of filtered latex of *Croton lechleri* Müll.Arg for use in treating or preventing or reducing the risk of a dermatological condition in a subject, wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard.

In certain embodiments, the specific dragon's blood tree of the present application is *Croton lechleri* Müll.Arg. of the Family: Euphorbiaceae. Dragon's blood is also referred to as Sangre de drago (Peru), Sangre de grado (Ecuador). Embodiments of the present invention are directed to hydrogel formulations of latex of *Croton lechleri*, preferably filtered latex of *Croton lechleri*, preferably filtered latex of *Croton lechleri* Müll.Arg and a pharmaceutically acceptable excipient. Such hydrogel formulations have been found to be useful in the successful treatment of dermatological conditions using the same. In some embodiments the hydrogel formulations are administered topically. In some embodiments the hydrogel formulations are administered nasally. Embodiments are directed to hydrogel formulations comprising latex of *Croton lechleri*, preferably filtered latex of *Croton lechleri*, preferably filtered latex of *Croton lechleri* Müll.Arg wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard, disclosed herein together with a pharmaceutically acceptable carrier, as well as methods of making and using the compounds and compositions. Certain embodiments are directed to methods for inhibiting dermatological conditions. Other embodiments are directed to methods for treating dermatological conditions in a patient in need of such treatment, comprising administering to said patient a therapeutically effective amount of a composition according to the present invention. Also provided is the use of certain extracts of *Croton lechleri* disclosed herein in the manufacture of a medicament for the treatment of dermatological conditions.

Hydrogel Formulations

Embodiments herein are directed to a hydrogel formulation comprising latex of *Croton lechleri*, preferably filtered latex of *Croton lechleri*, preferably filtered latex of *Croton lechleri* Müll.Arg., wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard.

The preferred treatment needs to be efficacious and has the ability to readily deliver broad spectrum antibiotic activity, inclusive of *Staphylococcus aureus*, MRSA and *Streptococcus pyogenes*. The antibiotic needs to release readily from the carrier, the carrier should help keep the antibiotic active ingredient on the skin, rather than enhancing skin penetration which could promote systemic absorption and lowering its safety profile. The amount of antibiotic should be at a substantial high level to achieve complete bacteria kill to minimize the initiation of antimicrobial resistance. The carrier should moisturize the afflicted area helping the skin return to its normal state. In the idea delivery system should also become a liquid bandage to help seal in moisture and protect the wounded or afflicted area. The AB-101 topical antibiotic delivery system has been developed to deliver these novel and unanticipated performance properties combined in one product to help promote the healing and resolution of these dermatological skin ailments.

The AB-101 topical antibiotic carrier system uses a hydrogel treatment vehicle and structure and can be incorporated but not limited to an ointment, gel, mousse, cream and spray format. The hydrogel containing AB-101 can be incorporated into a dressing, sponges, tapes, patches or bandages. It can be delivered via and not limited to a tube, pump, jar, manual/mechanical spray or aerosol packaging and delivery system. The hydrogel delivery system is designed for rapid release of the AB-101 pharmaceutical grade antibiotic, at maximum delivery dosage to ensure efficacy and safety. The hydrogel is an effective moisturizer due to its high-water content and the film forming properties of AB-101 combined with the hydrogel promotes the formation of a liquid bandage.

AB-101 can be used at a full strength or in an undiluted form as a topical antibiotic to treat skin conditions. In this form, AB-101 is thin and runny. The advantage of transforming and formulating AB-101 into a hydrogel provides unexpected and novel benefits associated with performance efficacy, improved safety profile, improved application, ease of dosage, promotion of protective liquid bandage properties, along with the known benefits of hydration.

Dosing of AB-101 to maximize efficacy is a critical requirement to ensure optimal performance. To avoid or at least minimize the promotion of antibiotic resistance, it is essential to eradicate all of the targeted bacteria. Specifically, antibiotic dosages are designed to eradicate entire populations of the pathogens. When antibiotics are not taken for the entire prescribed course, pathogenic bacteria can adapt to the presence of low dose antibiotics, and eventually form a population that is completely resistant to the antibiotic regardless of the dosage. This means that the design of the hydrogel vehicle needs to incorporate the maximum level AB-101 pharmaceutical grade as thermodynamically stable as possible. This requires formulation skill to those distinctively highly skilled in the art and requires intensive experimentation to identify the ideal formula.

The final pH of the hydrogel containing AB-101 may be within the range of 4.0 to 6.7. This range has both skin health benefits as well as antimicrobial benefits.

All hydrogels ingredients and incipient used with the AB-101 formulation need to meet the specification appropriate for either cosmetic grade or pharmaceutical grade carrier suitable for dermatological applications. To also ensure mildness, the AB-101 hydrogels do not use more than about 2 wt % of monohydroxy alcohols inclusive but not limited to methanol, ethanol, propanol, denatured alcohol and alkoxylated cetyl alcohol. AB-101 hydrogel formulation antibiotic activity is primarily dependent of the level of AB-101 and not at incipient level, where all formulations have a level of AB-101 ranging from 5% to 50%. AB-101 hydrogel formulation does not rely on cromoglicic acid or their salts as an active ingredient to treat dermatitis. Secondary antibiotic ingredients can also be included in the formulation as well as ingredients that can be helpful in improving skin health which may include and limited to vitamins, emollients, hyaluronic acid, propylene glycol, proteins and urea to help attract water to the skin and lanolin, mineral oil and petrolatum to lock in moisture.

*Croton lechleri*, Sangre de Drago or Dragons Blood have been used and incorporated in hydrogels. As in an example described by Vasquez studied the wound healing effect of a Sepigel based hydrogel on wound healing. The level of *Croton lechleri* used ranged for 0.5% to 2%. (Guillermo Jose Gallardo Vasquez, Bach. Laura Barboza Mejia, Healing effect of the gel made from the latex of *Croton lechleri* "Blood of Drago", Rev Cient Cienc Med 2015; 18 (1): 10-16). This gel is not suitable for use with eczema. The level of *Croton lechleri* is too low and the pH of these formulas are between are between 6.8 and 6.9. This gel is also formulated with ethyl alcohol which can decrease the mildness performance. Vasquez makes no reference to antibiotic activity. The level of *Croton lechleri* from an antibiotic standpoint would be seen as an incipient or non-efficacious level, that would not be effective in eradicating the bacteria infection and perhaps enabling antibiotic resistance. The pH level is too high and does not promote the ideal level for skin health, while actually promoting an environment that is favorable for *Staphylococcus aureus* and MRSA growth.

Bobrowski (U.S. Pat. No. 7,883,727) describes using an extract of *Croton lechleri*, CGO 110, as a treatment for emesis and itch. CGO 110 is depleted of the normal proanthocyanidins components to eliminate the red brownish color and is therefore structurally different from AB-101 via reduced proanthocyanidin levels. CGO 110 is formulated into an "*aloe barbadensis* gel for topical application for various inflamed, itching, and irritated dermatological applications." *Aloe barbadensis* gel is similar in nature to an aloe vera gel and is not considered a hydrogel (https://puracy-.com/blogs/ingredients/aloe-barbadensis, February 2021). The level of CGO 110, an extract of *croton lechleri* and is present in the *Aloe barbadensis* gel at less or than 2%. The topical gel described by Bobrowski should not be confused with a hydrogel designed to deliver AB-101.

Palacios Peláez et al (US 2019/0240193) formulates an aloe vera gel for skin treatment for atopic dermatitis which finds unexpected synergy between sodium cromoglycate formulations using alkoxylated cetyl alcohol as essential ingredients with low levels of *croton lechleri* and panthenol. The *croton lechleri* used is in the form of hydroglycolic solution (water and propylene glycol) where the *croton lechleri* is already diluted to 1% to 5% by weight. This solution is further diluted in Peláez's embodiment resulting in the *croton lechleri* being significantly below 2% of the total formula where the composition uses an aloe vera gel. The embodiments are dependent on the synergy of sodium cromoglycate which is not present in the AB-101 hydrogel composition.

The pharmaceutical AB-101 composition uses the whole *Croton lechleri* MÜll. Arg latex. The art is full of examples where the *Croton lechleri* Müll. Arg latex is fractionated, individual components are isolated or individual components are minimized or eliminated. This may be a result of the specific use. For the pharmaceutical grade of AB-101, the preference is to use the entire extract to leverage the synergy associated with all the active compounds.

Importantly, the variation of all the compounds vary greatly as indicated by the geography, environment, soil, elevation and age of the trees to name a few of the key variables. These variations are highlighted by Thiago Vaz Lopes, Dragon's blood (*Croton lechleri* MÜll. Arg; An Update on the Chemical Composition and Medical Applications of This Natural Plant Extract, Revista Brasileira de Higiene and Animal Health (v.7, n2) p. 167-192 (2013)).

The AB-101 novelty is based upon identifying the linkage between the specific compounds and their levels of concentration within AB-101 via a bioassay to in vitro efficacy and confirming via human use testing as an effective treatment for wound treating, bleeding treatment, and fighting infections. The utility of this novel discovery is the basis for developing a pharmaceutical drug and a medicinal product that will meet the FDA standards.

The FDA has established the requirement of having a bioassay that correlates the performance of the botanical raw material based on the chemical characterization of the composition and changes therein, to the efficacy against wound treating, bleeding treatment, and fighting infections.

The *Croton lechleri* MÜll. Arg latex is complex, difficult and not straightforward to define since its composition uses the full accompaniment of all of the bioactive materials comprising the *Croton lechleri* MÜll. Arg latex. Net, finding the critical active markers and performance and safety tests requires novel discovery.

The FDA requires the identification of the critical biomarkers or active constituents that drives the bioactivity. To that end, the critical biomarkers and their associated concentrations for AB-101 have never been published, defined or identified as associated with wound healing properties, antimicrobial activity and safety for treatment of wound treating, bleeding treatment, and fighting infections. Without this information, the FDA will not grant a drug status for medicinal use which is at the heart of becoming a pharmaceutical drug.

"Pharmaceutical Products" means any product, compound, medicine or therapeutic which is subject to regulation as a drug, medicine or controlled substance by a foreign equivalent of the United States Food and Drug Administration.

FDA guidance on botanicals states:
Because of the heterogeneous nature of a botanical drug and possible uncertainty about its active constituents, one of the critical issues for botanical drugs is ensuring that the therapeutic effect for marketed drug product batches is consistent. In general, therapeutic consistency can be supported by a "totality of the evidence" approach, including the following considerations:
  Botanical raw material control (e.g, agricultural practice and collection).
  Quality control by chemical test(s) (e.g., analytical tests such as spectroscopic and/or chromatographic methods that capture the active chemical constituents of a botanical drug substance) and manufacturing control (e.g., process validation).
  Biological assay (e.g. a biological assay that reflects the drug's known or intended mechanism of action) and clinical data (for details regarding use of clinical data in ensuring therapeutic consistency.

By using the whole *Croton lechleri* MÜll. Arg latex a unique synergy can be obtained across the entire composition that meets the specific bioassay performance targets. Table B shows 16 bioactives found in the pharmaceutical grade of AB-101. These bioactive compounds provide efficacy for: antimicrobial, antiviral, anti-inflammatory, cell proliferation to promote healing, anticancer, hemostatic, antioxidant and fibroblast stimulation to promote healing. By maintaining the *Croton lechleri* MÜll. Arg latex intact, a tremendous synergy is obtained across wound healing and preventing infections.

Table B shows bioactive compounds found in the whole *Croton lechleri* MÜll. Arg latex of AB-101 and their properties.

TABLE B

| Bioactive Chemical Components | Phytochemical Compound Class | Antimicrobial | Antiviral | Anti-inflammatory | Cell Proliferative (Wound Healing) | Anticancer | Hemostat | Antioxidant | Stimulating fibroblasts (Wound Healing) |
|---|---|---|---|---|---|---|---|---|---|
| 1,3,5-Trimethyoxybenzene | Flavonoid | X | | | | | | | |
| 2,4,6-Trimethoxyphenol | Phenol | X | X | | | X | | | |
| 3',4-O-dimethylcedrusin | Lignin | | | | | | | | X |
| 4-O-Dimethylcedrusin | Lignin | | | | X | | | | |
| Boldine, iso | Alkaloid | | | X | | X | | | |
| Catechin | Flavonoid | X | X | X | | | X | X | |
| Epicatechin | Flavonoid | | X | X | | | | X | |
| Epigallocatechin | Phenol | X | | | | | | X | |
| Flavan-3-ols | Flavonoids | X | X | | | | | | |
| Gallocatechin | Flavonoid | X | X | | X | | | X | |
| Magnoflorine | Alkaloid | X | X | X | | | | | |
| Proanthocyanidins | Polyphenols | X | X | X | X | X | | X | |
| Procyanidin | Flavonoids | X | X | X | X | | | | |
| Prodelphinidin | Tannins | X | | | | | | | |
| Sitosterol-Beta-Glucopyranoside | Phytosterol | X | X | X | | | | | |
| Taspine | Alkaloid | X | X | X | | X | | | |

Some embodiments herein are directed to a hydrogel formulation comprising latex of *Croton lechleri*, preferably filtered latex of *Croton lechleri*, preferably filtered latex of *Croton lechleri* Müll.Arg., wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard, of embodiments herein and a pharmaceutically acceptable excipient. Optionally, the hydrogel formulation hydrogel formulation may further comprise one or more other therapeutic ingredients. In embodiments, the hydrogel formulation comprises a therapeutically effective amount of the latex of *Croton lechleri*, preferably filtered latex of *Croton lechleri*, preferably filtered latex of *Croton lechleri* Müll.Arg., wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard. In embodiments, the hydrogel formulation is suitable for topical administration or is a topical hydrogel formulation. In some embodiments latex of *Croton lechleri*, preferably filtered latex of *Croton lechleri*, preferably filtered latex of *Croton lechleri* Müll.Arg. has a PDI of embodiments disclosed herein.

Embodiments herein are directed to a hydrogel formulation comprising:
latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard;
water;
one or more preservative-boosting humectants;
one or more chelating agents;
one or more dispersant/co-emulsifier agents;
one or more preservatives;
one or more emollients;
one or more deflocculants;
one or more thickening/stabilizing/emulsifying/texturizing agents; and
optionally one or more pH adjusters.

Embodiments herein are directed to a hydrogel formulation comprising latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard, propanediol, disodium edetate dihydrate, methylparaben, propylparaben, water, dimethicone, caprylic/capric triglyceride, and SEPINEO™ P 600 (acrylamide/sodium acryloyldimethyl taurate copolymer/isohexadecane/polysorbate 80).

Embodiments herein are directed to a hydrogel formulation comprising latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard, propanediol, disodium edetate dihydrate, PHOSAL® 50 PG (phosphatidylcholine, lysophosphatidylcholine, propylene glycol, sunflower seed oil glycerides, ethanol, soya fatty acids, ascorbyl palmitate, D,L-α-tocopherol), methylparaben, propylparaben, water, dimethicone, caprylic/capric triglyceride, SEPINEO™ P 600 (acrylamide/sodium acryloyldimethyl taurate copolymer/isohexadecane/polysorbate 80) sodium benzoate, potassium sorbate, and trolamine.

Embodiments herein are directed to a hydrogel formulation comprising latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard, propanediol, disodium edetate dihydrate, PHOSAL® 50 PG (phosphatidylcholine, lysophosphatidylcholine, propylene glycol, sunflower seed oil glycerides, ethanol, soya fatty acids, ascorbyl palmitate, D,L-α-tocopherol), methylparaben, propylparaben, water, dimethicone, caprylic/capric triglyceride, SEPINEO™ P 600 (acrylamide/sodium acryloyldimethyl taurate copolymer/isohexadecane/polysorbate 80), sodium benzoate, and potassium sorbate.

Embodiments herein are directed to a hydrogel formulation comprising latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard, propanediol, disodium edetate dihydrate, methylparaben, propylparaben, water, dimethicone, caprylic/capric triglyceride, SEPINEO™ P 600 (acrylamide/sodium acryloyldimethyl taurate copolymer/isohexadecane/polysorbate 80), wherein the *Croton lechleri* contains at least about 110 PPM of Gallocatechin, at least about 780 PPM of Epigallocatechin, at least about 1.6 PPM of Catechin at least about 2 PPM of Epicatechin, at least about 45 PPM Taspine, at least about 0.1 PPM of dimethylcedrusin, and wherein the *Croton lechleri* has a polydispersity index of about 0.5 to about 0.85.

Embodiments herein are directed to a hydrogel formulation comprising latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard, propanediol, disodium edetate dihydrate, PHOSAL® 50 PG (phosphatidylcholine, lysophosphatidylcholine, propylene glycol, sunflower seed oil glycerides, ethanol, soya fatty acids, ascorbyl palmitate, D,L-α-tocopherol), methylparaben, propylparaben, water, dimethicone, caprylic/capric triglyceride, SEPINEO™ P 600 (acrylamide/sodium acryloyldimethyl taurate copolymer/isohexadecane/polysorbate 80) sodium benzoate, potassium sorbate, trolamine, wherein the *Croton lechleri* contains at least about 110 PPM of Gallocatechin, at least about 780 PPM of Epigallocatechin, at least about 1.6 PPM of Catechin at least about 2 PPM of Epicatechin, at least about 45 PPM Taspine, at least about 0.1 PPM of dimethylcedrusin, and wherein the *Croton lechleri* has a polydispersity index of about 0.5 to about 0.85.

Embodiments herein are directed to a hydrogel formulation comprising latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard, propanediol, disodium edetate dihydrate, PHOSAL® 50 PG (phosphatidylcholine, lysophosphatidylcholine, propylene glycol, sunflower seed oil glycerides, ethanol, soya fatty acids, ascorbyl palmitate, D,L-α-tocopherol), methylparaben, propylparaben, water, dimethicone, caprylic/capric triglyceride, SEPINEO™ P 600 (acrylamide/sodium acryloyldimethyl taurate copolymer/isohexadecane/polysorbate 80), sodium benzoate, potassium sorbate, wherein the *Croton lechleri* contains at least about 110 PPM of Gallocatechin, at least about 780 PPM of Epigallocatechin, at least about 1.6 PPM of Catechin at least about 2 PPM of Epicatechin, at least about 45 PPM Taspine, at least about 0.1 PPM of dimethylcedrusin, and wherein the *Croton lechleri* has a polydispersity index of about 0.5 to about 0.85.

Embodiments herein are directed to a hydrogel formulation comprising latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard, glycerin, methylparaben, propylparaben, water, sodium phosphate dibasic heptahydrate, sodium phosphate monobasic, sodium hexametaphosphate, medium chain triglycerides, SEPINEO™ P 600 (acrylamide/sodium acryloyldimethyl taurate copolymer/isohexadecane/polysorbate 80), wherein the *Croton lechleri* contains at least about 110 PPM of Gallocatechin, at least about 780 PPM of Epigallocatechin, at least about 1.6 PPM of Catechin at least about 2 PPM of Epicatechin, at least about 45 PPM Taspine, at least about 0.1 PPM of dimethylcedrusin, and wherein the *Croton lechleri* has a polydispersity index of about 0.5 to about 0.85.

In some embodiments of the hydrogel formulation, the filtered latex of *Croton lechleri* is filtered latex of *Croton lechleri* Müll.Arg.

In certain embodiments, latex of *Croton lechleri*, preferably filtered latex of *Croton lechleri*, preferably filtered latex of *Croton lechleri* Müll.Arg. comprises one or more compounds selected from: gallocatechin, epigallocatechin, catechin, epicatechin, taspine, and dimethylcedrusin and combinations thereof.

Each of gallocatechin, epigallocatechin, catechin, epicatechin, taspine, and dimethylcedrusin may be present in the latex of *Croton lechleri*, preferably filtered latex of *Croton lechleri*, preferably filtered latex of *Croton lechleri* Müll.Arg. in at least the amounts found in Table 1a or any combination of such amounts.

Embodiments herein are directed to hydrogel formulations comprising latex of *Croton lechleri*, preferably filtered latex of *Croton lechleri*, preferably filtered latex of *Croton lechleri* Müll.Arg. and a pharmaceutically acceptable excipient. In certain embodiments, latex of *Croton lechleri*, preferably filtered latex of *Croton lechleri*, preferably filtered latex of *Croton lechleri* Müll.Arg. comprises one or more compounds selected from: gallocatechin, epigallocatechin, catechin, epicatechin, taspine, and dimethylcedrusin and combinations thereof. Each of gallocatechin, epigallocatechin, catechin, epicatechin, taspine and dimethylcedrusin may be present in the latex of *Croton lechleri*, preferably filtered latex of *Croton lechleri*, preferably filtered latex of *Croton lechleri* Müll.Arg. in at least the amounts found in Table 1a or any combination of such amounts.

As shown in Table B, there are a broad range of compounds present in AB-101. The primary bioactive reference standard for the pharmaceutical grade of AB-101 are the Gallocatechin, Epigallocatechin, Catechins, Epicatechin, Taspine and Dimethylcedrusin. Of particular importance is a secondary set of polyphenol bioactives composed of the gallate family including Catechin Gallate (CG), Epicatechin Gallate (ECG), Gallocatechin Gallate (GCG) and Epigallocatechin Gallate (EGCG). The gallate family bioactive profile of particular importance to AB-101 include the antimicrobial and antioxidants properties. These properties have been noted and indicated in Rahardiyan, Dino. (2018), Antibacterial potential of catechin of tea (*Camellia sinensis*) and its applications, Food Research. 3. 1-6, and Multifunctional Antioxidant Activities of Alkyl Gallates *The Open Bioactive Compounds Journal*, 2010, 3: 1-11 Isao Kubo, Noriyoshi Masuoka, Tae Joung Ha, Kuniyoshi Shimizu, Ken-ichi Nihei.

From a composition standpoint the primary and secondary bioactives compose between 80% to 99% of the concentration composition of the pharmaceutical grade of AB-101, where the remaining other compounds not characterized comprise the remaining whole of AB-101. Within the whole, the gallate bioactive family can contribute between 1% to 20% of the bioactive. For AB-101 Lot 01, the primary bioactive reference range is between 85% to 90%, the secondary reference range is between 3% to 4% and the total compounds not characterized in AB-101 ranges from 7% to 11%.

The contribution of the entire *Croton lechleri* Müll. Arg latex having a unique synergy across the entire composition that meets the specific bioassay performance targets resulting in a composition that has great natural polydispersity as measured by a Polydispersity Index Analysis. The primary reference standard is the main focus of the pharmaceutical grade of AB-101's bioactivity, where the secondary reference standard demonstrates the biodiversity, the polydispersity and synergy makeup within AB-101, which also contributes to AB-101 efficacy.

TABLE 1a

| Compound | Exemplary Amount present in the latex (PPM is in µg/g) |
|---|---|
| Gallocatechin | at least about 110 PPM |
| Epigallocatechin | at least about 780 PPM |
| Catechin | at least about 1.6 PPM |
| Epicatechin | at least about 2 PPM |

TABLE 1a-continued

| Compound | Exemplary Amount present in the latex (PPM is in µg/g) |
|---|---|
| Taspine | at least about 45 PPM |
| Dimethylcedrusin | at least about 0.1 PPM |

TABLE 1b

| Compound or compounds | Exemplary Amount present in the latex as a % of total Proanthocyanidins (PAC) |
|---|---|
| Gallocatechin and Epigallocatechin combined | at least about 60% |
| Epigallocatechin | at least about 45% |

TABLE 1c

Exemplary Antibiotic Activity

| Bacteria | Exemplary MIC | Exemplary MBC |
|---|---|---|
| Methicillin-susceptible *Staphylococcus aureus* (MSSA) | 50 µg/mL or less | 50 µg/mL or less |
| Methicillin-resistant *Staphylococcus aureus* (MRSA) | 50 µg/mL or less | 50 µg/mL or less |
| *Pseudomonas aeruginosa* | 50 µg/mL or less | 50 µg/mL or less |
| *Streptococcus pyongenes* | 50 µg/mL or less | 50 µg/mL or less |

TABLE 1d

Exemplary LogP for each of gallocatechin, epigallocatechin, catechin, epicatechin, and taspine

| IVPT: Skin Permeation Flux Calculation for ECG | at least about less than 500 µg/cm$^2$/hr |
|---|---|
| IVRT: API (Active Pharmacetuical Ingredient) Release Flux Calculation for ECG | at least about less than 2400 µg/cm$^2$/hr |
| ECG LogP: Partition Coefficient Calculation | at least about or less than 2.5 |

TABLE 1e

Exemplary Additional Properties

| Film Forming Properties | Present as observed on skin |
|---|---|

If the latex of *Croton lechleri*, preferably filtered latex of *Croton lechleri*, preferably filtered latex of *Croton lechleri* Müll.Arg. fails to contain the amounts of gallocatechin, epigallocatechin, catechin, epicatechin, taspine and dimethylcedrusin in at least the amounts set forth in Table 1a, it is not suitable for use in the hydrogel formulations and methods of use described herein.

In some embodiments, the gallocatechin present in the latex is in an amount of at least about 110 PPM, at least about 115 PPM, at least about 120 PPM, at least about 125 PPM, at least about 130 PPM, at least about 135 PPM, at least about 140 PPM, at least about 145 PPM, at least about 150 PPM, at least about 155 PPM, at least about 160 PPM, at least about 165 PPM, at least about 170 PPM, at least about 175 PPM, at least about 180 PPM, at least about 185

PPM, at least about 190 PPM, at least about 195 PPM, at least about 200 PPM, or a range between any two of these values.

In some embodiments, the epigallocatechin present in the latex is in an amount of at least about 780 PPM, at least about 790 PPM, at least about 800 PPM, at least about 810 PPM, at least about 820 PPM, at least about 830 PPM, at least about 840 PPM, at least about 850 PPM, at least about 860 PPM, at least about 870 PPM, at least about 880 PPM, at least about 890 PPM, at least about 900 PPM, at least about 910 PPM, at least about 920 PPM, at least about 930 PPM, at least about 940 PPM, at least about 950 PPM, at least about 960 PPM, at least about 970 PPM, at least about 980 PPM, at least about 990 PPM, at least about 1000 PPM, at least about 1010 PPM, at least about 1020 PPM, at least about 1030 PPM, at least about 1040 PPM, at least about 1050 PPM, at least about 1060 PPM, at least about 1070 PPM, at least about 1080 PPM, at least about 1090 PPM, at least about 1100 PPM, at least about 1110 PPM, at least about 1120 PPM, at least about 1130 PPM, at least about 1140 PPM, at least about 1150 PPM, at least about 1160 PPM, at least about 1170 PPM, at least about 1180 PPM, at least about 1190 PPM, at least about 1200 PPM, at least about 1210 PPM, at least about 1220 PPM, at least about 1230 PPM, at least about 1240 PPM, at least about 1250 PPM, at least about 1260 PPM, at least about 1270 PPM, at least about 1280 PPM, at least about 1290 PPM, at least about 1300 PPM, at least about 1310 PPM, at least about 1320 PPM, at least about 1330 PPM, at least about 1340 PPM, at least about 1350 PPM, at least about 1360 PPM, at least about 1370 PPM, at least about 1380 PPM, at least about 1390 PPM, at least about 1400 PPM, at least about 1410 PPM, at least about 1420 PPM, at least about 1430 PPM, at least about 1440 PPM, at least about 1450 PPM, at least about 1460 PPM, at least about 1470 PPM, at least about 1480 PPM, at least about 1490 PPM, at least about 1500 PPM, at least about 1510 PPM, at least about 1520 PPM, at least about 1530 PPM, at least about 1540 PPM, at least about 1550 PPM, at least about 1560 PPM, at least about 1570 PPM, at least about 1580 PPM, at least about 1590 PPM, at least about 1600 PPM, at least about 1610 PPM, at least about 1620 PPM, at least about 1630 PPM, at least about 1640 PPM, at least about 1650 PPM, at least about 1660 PPM, at least about 1670 PPM, at least about 1680 PPM, at least about 1690 PPM, at least about 1700 PPM, or a range between any two of these values.

In some embodiments, the catechin present in the latex is in an amount of at least about 1.6 PPM, at least about 1.7 PPM, at least about 1.8 PPM, at least about 1.9 PPM, at least about 2.0 PPM, at least about 2.1 PPM, at least about 2.2 PPM, at least about 2.3 PPM, at least about 2.4 PPM, at least about 2.5 PPM, at least about 2.6 PPM, at least about 2.7 PPM, at least about 2.8 PPM, at least about 2.9 PPM, at least about 3.0 PPM, at least about 3.1 PPM, at least about 3.2 PPM, at least about 3.3 PPM, at least about 3.4 PPM, at least about 3.5 PPM, at least about 3.6 PPM, at least about 3.7 PPM, at least about 3.8 PPM, at least about 3.9 PPM, at least about 4.0 PPM, at least about 4.1 PPM, at least about 4.2 PPM, at least about 4.3 PPM, at least about 4.4 PPM, at least about 4.5 PPM, at least about 4.6 PPM, at least about 4.7 PPM, at least about 4.8 PPM, at least about 4.9 PPM, at least about 5.0 PPM, at least about 5.1 PPM, at least about 5.2 PPM, at least about 5.3 PPM, at least about 5.4 PPM, at least about 5.5 PPM, at least about 5.6 PPM, at least about 5.7 PPM, at least about 5.8 PPM, at least about 5.9 PPM, at least about 6.0 PPM, at least about 6.1 PPM, at least about 6.2 PPM, at least about 6.3 PPM, at least about 6.4 PPM, at least about 6.5 PPM, at least about 6.6 PPM, at least about 6.7 PPM, at least about 6.8 PPM, at least about 6.9 PPM, at least about 7.0 PPM, at least about 7.1 PPM, at least about 7.2 PPM, at least about 7.3 PPM, at least about 7.4 PPM, at least about 7.5 PPM, at least about 7.6 PPM, at least about 7.7 PPM, at least about 7.8 PPM, at least about 7.9 PPM, at least about 8.0 PPM, at least about 8.1 PPM, at least about 8.2 PPM, at least about 8.3 PPM, at least about 8.4 PPM, at least about 8.5 PPM, at least about 8.6 PPM, at least about 8.7 PPM, at least about 8.8 PPM, at least about 8.9 PPM, at least about 9.0 PPM, at least about 9.1 PPM, at least about 9.2 PPM, at least about 9.3 PPM, at least about 9.4 PPM, at least about 9.5 PPM, at least about 9.6 PPM, at least about 9.7 PPM, at least about 9.8 PPM, at least about 9.9 PPM, at least about 10.0 PPM, at least about 10.1 PPM, at least about 10.2 PPM, at least about 10.3 PPM, at least about 10.4 PPM, at least about 10.5 PPM, at least about 10.6 PPM, at least about 10.7 PPM, at least about 10.8 PPM, at least about 10.9 PPM, at least about 11.0 PPM, or a range between any two of these values.

In some embodiments, the epicatechin present in the latex is in an amount of at least about 2.0 PPM, at least about 2.1 PPM, at least about 2.2 PPM, at least about 2.3 PPM, at least about 2.4 PPM, at least about 2.5 PPM, at least about 2.6 PPM, at least about 2.7 PPM, at least about 2.8 PPM, at least about 2.9 PPM, at least about 3.0 PPM, at least about 3.1 PPM, at least about 3.2 PPM, at least about 3.3 PPM, at least about 3.4 PPM, at least about 3.5 PPM, at least about 3.6 PPM, at least about 3.7 PPM, at least about 3.8 PPM, at least about 3.9 PPM, at least about 4.0 PPM, at least about 4.1 PPM, at least about 4.2 PPM, at least about 4.3 PPM, at least about 4.4 PPM, at least about 4.5 PPM, at least about 4.6 PPM, at least about 4.7 PPM, at least about 4.8 PPM, at least about 4.9 PPM, at least about 5.0 PPM, at least about 5.1 PPM, at least about 5.2 PPM, at least about 5.3 PPM, at least about 5.4 PPM, at least about 5.5 PPM, at least about 5.6 PPM, at least about 5.7 PPM, at least about 5.8 PPM, at least about 5.9 PPM, at least about 6.0 PPM, at least about 6.1 PPM, at least about 6.2 PPM, at least about 6.3 PPM, at least about 6.4 PPM, at least about 6.5 PPM, at least about 6.6 PPM, at least about 6.7 PPM, at least about 6.8 PPM, at least about 6.9 PPM, at least about 7.0 PPM, at least about 7.1 PPM, at least about 7.2 PPM, at least about 7.3 PPM, at least about 7.4 PPM, at least about 7.5 PPM, at least about 7.6 PPM, at least about 7.7 PPM, at least about 7.8 PPM, at least about 7.9 PPM, at least about 8.0 PPM, at least about 8.1 PPM, at least about 8.2 PPM, at least about 8.3 PPM, at least about 8.4 PPM, at least about 8.5 PPM, at least about 8.6 PPM, at least about 8.7 PPM, at least about 8.8 PPM, at least about 8.9 PPM, at least about 9.0 PPM, at least about 9.1 PPM, at least about 9.2 PPM, at least about 9.3 PPM, at least about 9.4 PPM, at least about 9.5 PPM, at least about 9.6 PPM, at least about 9.7 PPM, at least about 9.8 PPM, at least about 9.9 PPM, at least about 10.0 PPM, or a range between any two of these values.

In some embodiments, the taspine present in the latex is in an amount of at least about 45 PPM, at least about 46 PPM, at least about 47 PPM, at least about 48 PPM, at least about 49 PPM, at least about 50 PPM, at least about 51 PPM, at least about 52 PPM, at least about 53 PPM, at least about 54 PPM, at least about 55 PPM, at least about 56 PPM, at least about 57 PPM, at least about 58 PPM, at least about 59 PPM, at least about 60 PPM, at least about 61 PPM, at least about 62 PPM, at least about 63 PPM, at least about 64 PPM, at least about 65 PPM, or a range between any two of these values.

In some embodiments, the dimethylcedrusin present in the latex is in an amount of at least about 0.1 mg of dimethylcedrusin/kg of latex, at least about 0.11 PPM, at least about 0.12 PPM, at least about 0.13 PPM, at least about 0.14 PPM, at least about 0.15 PPM, at least about 0.16 PPM, at least about 0.17 PPM, at least about 0.18 PPM, at least about 0.18 PPM, at least about 0.19 PPM, at least about 0.20 PPM, at least about 0.21 PPM, at least about 0.22 PPM, at least about 0.23 PPM, at least about 0.24 PPM, at least about 0.25 PPM, at least about 0.26 PPM, at least about 0.27 PPM, at least about 0.28 PPM, at least about 0.29 PPM, at least about 0.30 PPM, at least about 0.31 PPM, at least about 0.32 PPM, at least about 0.33 PPM, at least about 0.34 PPM, at least about 0.35 PPM, at least about 0.36 PPM, at least about 0.37 PPM, at least about 0.38 PPM, at least about 0.39 PPM, about 0.40 PPM, at least about 0.41 PPM, at least about 0.42 PPM, at least about 0.43 PPM, at least about 0.44 PPM, at least about 0.45 PPM, at least about 0.46 PPM, at least about 0.47 PPM, at least about 0.48 PPM, at least about 0.49 PPM, at least about 0.5 PPM, at least about 0.6 PPM, at least about 0.7 PPM, at least about 0.8 PPM, at least about 0.9 PPM, at least about 1.0 PPM, at least about 1.1 PPM, at least about 1.2 PPM, at least about 1.3 PPM, at least about 1.4 PPM, at least about 1.5 PPM, at least about 1.6 PPM, at least about 1.7 PPM, at least about 1.8 PPM, at least about 1.9 PPM, at least about 2.0 PPM, at least about 2.1 PPM, at least about 2.2 PPM, at least about 2.3 PPM, at least about 2.4 PPM, at least about 2.5 PPM, at least about 2.6 PPM, at least about 2.7 PPM, at least about 2.8 PPM, at least about 2.9 PPM, at least about 3.0 PPM, at least about 3.1 PPM, at least about 3.2 PPM, at least about 3.3 PPM, at least about 3.4 PPM, at least about 3.5 PPM, at least about 3.6 PPM, at least about 3.7 PPM, at least about 3.8 PPM, at least about 3.9 PPM, at least about 4.0 PPM, at least about 4.1 PPM, at least about 4.2 PPM, at least about 4.3 PPM, at least about 4.4 PPM, at least about 4.5 PPM, at least about 4.6 PPM, at least about 4.7 PPM, at least about 4.8 PPM, at least about 4.9 PPM, at least about 5.0 PPM, at least about 5.1 PPM, at least about 5.2 PPM, at least about 5.3 PPM, at least about 5.4 PPM, at least about 5.5 PPM, at least about 5.6 PPM, at least about 5.7 PPM, at least about 5.8 PPM, at least about 5.9 PPM, at least about 6.0 PPM, at least about 6.1 PPM, at least about 6.2 PPM, at least about 6.3 PPM, at least about 6.4 PPM, at least about 6.5 PPM, at least about 6.6 PPM, at least about 6.7 PPM, at least about 6.8 PPM, at least about 6.9 PPM, at least about 7.0 PPM, at least about 7.1 PPM, at least about 7.2 PPM, at least about 7.3 PPM, at least about 7.4 PPM, at least about 7.5 PPM, at least about 7.6 PPM, at least about 7.7 PPM, at least about 7.8 PPM, at least about 7.9 PPM, at least about 8.0 PPM, at least about 8.1 PPM, at least about 8.2 PPM, at least about 8.3 PPM, at least about 8.4 PPM, at least about 8.5 PPM, at least about 8.6 PPM, at least about 8.7 PPM, at least about 8.8 PPM, at least about 8.9 PPM, at least about 9.0 PPM, at least about 9.1 PPM, at least about 9.2 PPM, at least about 9.3 PPM, at least about 9.4 PPM, at least about 9.5 PPM, at least about 9.6 PPM, at least about 9.7 PPM, at least about 9.8 PPM, at least about 9.9 PPM, at least about 10.0 PPM, or a range between any two of these values.

In some embodiments, the hydrogel formulation is suitable for topical administration (including, for example, dermal, oral mucosa, buccal, sublingual intraocular, and wound cavity).

In some embodiments of the hydrogel formulation, the latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard is in an amount of about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 55% to about 80%, about 60% to about 80%, about 65% to about 80%, about 70% to about 80%, about 75% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 75%, about 15% to about 70%, about 20% to about 65%, about 25% to about 60%, about 30% to about 55%, about 35% to about 55%, about 40% to about 50%, or a value within one of these ranges. Specific examples may include about 5%, about 10%, about 15%, about 20%, about 25%, about 30%, about 35%, about 36%, about 37%, about 38%, about 39%, about 40%, about 41%, about 42%, about 43%, about 44%, about 45%, about 46%, about 47%, about 48%, about 49%, about 50%, about 55%, about 60%, about 65%, about 70%, about 75%, about 80%, or a range between any two of these values. In certain embodiments of the hydrogel formulation the latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard is in an amount of about 40%. In certain embodiments of the hydrogel formulation the latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard is in an amount of about 50%. In certain embodiments of the hydrogel formulation the latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard is in an amount of about 43%. In certain embodiments of the hydrogel formulation the latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard is in an amount of about 45%. The forgoing percentages are relative to a composition made from AB-101 with exemplary amounts of the marker compounds present in the latex as disclosed in Table 1a. To illustrate, a pharmaceutical composition comprising 100% of AB-101 will contain at least about 110 PPM of gallocatechin, while a pharmaceutical composition comprising 200% of AB-101 will contain at least about 220 PPM of gallocatechin. The foregoing all represent weight percentages of embodiments of the hydrogel formulations.

In some embodiments of the hydrogel formulation, the one or more preservative-boosting humectants is selected from the group consisting of ZEMEA® USP, propanediol, and combinations thereof.

In some embodiments of the hydrogel formulation, the one or more preservative-boosting humectants is in an amount of about 1% to about 10%, about 2% to about 10%, about 3% to about 10%, about 4% to about 10%, about 5% to about 10%, about 6% to about 10%, about 7% to about 10%, about 8% to about 10%, about 9% to about 10%, about 1% to about 9%, about 1% to about 8%, about 1% to about 7%, about 1% to about 6%, about 1% to about 5%, about 1% to about 4%, about 1% to about 3%, about 1% to about 2%, about 2% to about 9%, about 3% to about 8%, about 4% to about 7%, about 5% to about 6%, or a value within one of these ranges. Specific examples may include about 1%, about 2%, about 3%, about 4%, about 5%, about 6%, about 7%, about 8%, about 9%, about 10%, or a range between any two of these values. In certain embodiments of the hydrogel formulation the one or more preservative-boosting humectants is in an amount of about 5%. In certain embodiments of the hydrogel formulation the one or more preservative-boosting humectants is in an amount of about 4%. The foregoing all represent weight percentages of embodiments of the hydrogel formulations.

In some embodiments of the hydrogel formulation, the one or more chelating agents is selected from the group consisting of disodium edetate dihydrate, disodium EDTA, and combinations thereof.

In some embodiments of the hydrogel formulation, the one or more chelating agents is in an amount of about 0.05% to about 0.5%, about 0.1% to about 0.5%, about 0.15% to about 0.5%, about 0.2% to about 0.5%, about 0.25% to about 0.5%, about 0.3% to about 0.5%, about 0.35% to about 0.5%, about 0.4% to about 0.5%, about 0.45% to about 0.5%, about 0.05% to about 0.45%, about 0.05% to about 0.4%, about 0.05% to about 0.35%, about 0.05% to about 0.3%, about 0.05% to about 0.25%, about 0.05% to about 0.2%, about 0.05% to about 0.15%, about 0.05% to about 0.1%, about 0.1% to about 0.45%, about 0.15% to about 0.4%, about 0.2% to about 0.35%, about 0.25% to about 0.30%, about 0.05% to about 0.25%, about 0.075% to about 0.225%, about 0.1% to about 0.2%, about 0.125% to about 0.175%, or a value within one of these ranges. Specific examples may include about 0.05%, about 0.1%, about 0.15%, about 0.2%, about 0.25%, about 0.3%, about 0.35%, about 0.4%, about 0.45%, about 0.5%, about 0.2%, about 0.225%, about 0.25%, about 0.275%, about 0.3%, or a range between any two of these values. In certain embodiments of the hydrogel formulation the one or more chelating agents is in an amount of about 0.15%. In certain embodiments of the hydrogel formulation the one or more chelating agents is in an amount of about 0.10%. The foregoing all represent weight percentages of embodiments of the hydrogel formulations.

In some embodiments of the hydrogel formulation, the one or more dispersant/co-emulsifier agents is selected from the group consisting of PHOSAL® 50 PG, phosphatidylcholine, lysophosphatidylcholine, propylene glycol, sunflower seed oil glycerides, ethanol, soya fatty acids, ascorbyl palmitate, D,L-α-tocopherol, and combinations thereof.

In some embodiments of the hydrogel formulation, the one or more dispersant/co-emulsifier agents is in an amount of about 0.5% to about 5%, about 1% to about 3%, 0.5% to about 2%, about 0.05% to about 0.2%, about 0.25% to about 1.25%, about 0.01% to about 0.1%, about 0.001% to about 0.01%, about 0.005% to about 0.02%, or a value within one of these ranges. Specific examples may include about 0.001%, about 0.004%, about 0.005%, about 0.01%, about 0.02%, about 0.03%, about 0.04%, about 0.05%, about 0.1%, about 0.4%, about 0.5%, about 0.6%, about 0.7%, about 0.8%, about 0.9%, about 1%, about 2%, about 3%, or a range between any two of these values. In certain embodiments of the hydrogel formulation the one or more dispersant/co-emulsifier agents is in an amount of about 2%. In certain embodiments of the hydrogel formulation the one or more dispersant/co-emulsifier agents is in an amount of about 1%. In certain embodiments of the hydrogel formulation the one or more dispersant/co-emulsifier agents is in an amount of about 0.824%. In certain embodiments of the hydrogel formulation the one or more dispersant/co-emulsifier agents is in an amount of about 0.676%. In certain embodiments of the hydrogel formulation the one or more dispersant/co-emulsifier agents is in an amount of about 0.12%. In certain embodiments of the hydrogel formulation the one or more dispersant/co-emulsifier agents is in an amount of about 0.05%. In certain embodiments of the hydrogel formulation the one or more dispersant/co-emulsifier agents is in an amount of about 0.03%. In certain embodiments of the hydrogel formulation the one or more dispersant/co-emulsifier agents is in an amount of about 0.01%. In certain embodiments of the hydrogel formulation the one or more dispersant/co-emulsifier agents is in an amount of about 0.004%. In certain embodiments of the hydrogel formulation the one or more dispersant/co-emulsifier agents is in an amount of about 0.8%. In certain embodiments of the hydrogel formulation the one or more dispersant/co-emulsifier agents is in an amount of about 0.7%. In certain embodiments of the hydrogel formulation the one or more dispersant/co-emulsifier agents is in an amount of about 0.1%. The foregoing all represent weight percentages of embodiments of the hydrogel formulations.

In some embodiments of the hydrogel formulation, the one or more preservatives is selected from the group consisting of methylparaben, propylparaben, sodium benzoate, potassium sorbate, and combinations thereof.

In some embodiments of the hydrogel formulation, the one or more preservatives is in an amount of about 0.005% to about 0.1%, about 0.1% to about 1%, about 0.05% to about 0.5%, or a value within one of these ranges. Specific examples may include about 0.005%, about 0.01%, about 0.02%, about 0.03%, about 0.04%, about 0.05%, about 0.1%, about 0.4%, about 0.45%, about 0.5%, about 0.6%, about 0.7%, about 0.8%, about 0.9%, about 1%, about 2%, about 3%, or a range between any two of these values. In certain embodiments of the hydrogel formulation the one or more preservatives is in an amount of about 0.45%. In certain embodiments of the hydrogel formulation the one or more preservatives is in an amount of about 0.4%. In certain embodiments of the hydrogel formulation the one or more preservatives is in an amount of about 0.1%. In certain embodiments of the hydrogel formulation the one or more preservatives is in an amount of about 0.02%. In certain embodiments of the hydrogel formulation the one or more preservatives is in an amount of about 0.5%. The foregoing all represent weight percentages of embodiments of the hydrogel formulations.

In some embodiments of the hydrogel formulation, the one or more emollients is selected from the group consisting of DOW CORNING® Q7 9120 (PHARMACEUTICAL GRADE), Dow Corning® 200 Fluid 350 cSt, LABRAFAC™ WL1349, dimethicone, medium-chain triglycerides, and combinations thereof.

In some embodiments of the hydrogel formulation, the one or more emollients is in an amount of about 0.5% to about 10%, about 1% to about 10%, about 1.5% to about 10%, about 2% to about 10%, about 2.5% to about 10%, about 3% to about 10%, about 3.5% to about 10%, about 4% to about 10%, about 4.5% to about 10%, about 5% to about 10%, about 5.5% to about 10%, about 6% to about 10%, about 6.5% to about 10%, about 7% to about 10%, about 7.5% to about 10%, about 8% to about 10%, about 8.5% to about 10%, about 9% to about 10%, about 9.5% to about 10%, about 0.5% to about 9.5%, about 0.5% to about 9%, about 0.5% to about 8.5%, about 0.5% to about 8%, about 0.5% to about 7.5%, about 0.5% to about 7%, about 0.5% to about 6.5%, about 0.5% to about 6%, about 0.5% to about 5.5%, about 0.5% to about 5%, about 0.5% to about 4.5%, about 0.5% to about 4%, about 0.5% to about 3.5%, about 0.5% to about 3%, about 0.5% to about 2.5%, about 0.5% to about 2%, about 0.5% to about 1.5%, about 0.5% to about 1%, about 1% to about 9.5%, about 1.5% to about 9%, about 2% to about 8.5%, about 0.5% to about 8%, about 3% to about 7.5%, about 3.5% to about 7%, about 4% to about 6.5%, about 4.5% to about 6%, about 5% to about 5.5%, about 1% to about 5%, about 1.5% to about 4.5%, about 2% to about 4%, about 2.5% to about 3.5%, or a value within one of these ranges. Specific examples may include about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, or a range between any two of these values. In certain embodiments of the hydrogel formulation the one or more emollients is in an amount of about 2%. In certain embodiments of the hydrogel formulation the one or more emollients is in an amount of about 2.5%. In certain embodiments of the hydrogel formulation the one or more emollients is in an amount of about 5%. In certain embodiments of the hydrogel formulation the one or more emollients is in an amount of about 7%. The foregoing all represent weight percentages of embodiments of the hydrogel formulations.

In some embodiments of the hydrogel formulation, the one or more thickening/stabilizing/emulsifying/texturizing agents is selected from the group consisting of SEPINEO™ P 600 (acrylamide/sodium acryloyldimethyl taurate copolymer/isohexadecane/polysorbate 80), acrylamide/sodium acryloyldimethyl taurate copolymer, isohexadecane, polysorbate 80, and combinations thereof.

In some embodiments of the hydrogel formulation, the one or more thickening/stabilizing/emulsifying/texturizing agents is in an amount of about 0.05% to about 10%, about 0.05% to about 5%, about 0.05% to about 1%, about 0.5% to about 3%, 0.5% to about 2%, 0.5% to about 1.5%, about 0.5% to about 1%, about 2% to about 6%, or a value within one of these ranges. Specific examples may include about 0.05%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 5.5%, about 6%, or a range between any two of these values. In certain embodiments of the hydrogel formulation the one or more thickening/stabilizing/emulsifying/texturizing agents is in an amount of about 4%. In certain embodiments of the hydrogel formulation the one or more thickening/stabilizing/emulsifying/texturizing agents is in an amount of about 1.4%. In certain embodiments of the hydrogel formulation the one or more thickening/stabilizing/emulsifying/texturizing agents is in an amount of about 1.6%. In certain embodiments of the hydrogel formulation the one or more thickening/stabilizing/emulsifying/texturizing agents is in an amount of about 0.8%. In certain embodiments of the hydrogel formulation the one or more thickening/stabilizing/emulsifying/texturizing agents is in an amount of about 1%. In certain embodiments of the hydrogel formulation the one or more thickening/stabilizing/emulsifying/texturizing agents is in an amount of about 0.2%. In certain embodiments of the hydrogel formulation the one or more thickening/stabilizing/emulsifying/texturizing agents is in an amount of about 0.4%. In certain embodiments of the hydrogel formulation the one or more thickening/stabilizing/emulsifying/texturizing agents is in an amount of about 1.3%. The foregoing all represent weight percentages of embodiments of the hydrogel formulations.

In some embodiments of the hydrogel formulation, the one or more pH adjusters is trolamine.

In some embodiments of the hydrogel formulation, the one or more pH adjusters is in an amount of about 0.05% to about 0.5%, about 0.1% to about 0.5%, about 0.15% to about 0.5%, about 0.2% to about 0.5%, about 0.25% to about 0.5%, about 0.3% to about 0.5%, about 0.35% to about 0.5%, about 0.4% to about 0.5%, about 0.45% to about 0.5%, about 0.05% to about 0.45%, about 0.05% to about 0.4%, about 0.05% to about 0.35%, about 0.05% to about 0.3%, about 0.05% to about 0.25%, about 0.05% to about 0.2%, about 0.05% to about 0.15%, about 0.05% to about 0.1%, about 0.1% to about 0.45%, about 0.15% to about 0.4%, about 0.2% to about 0.35%, about 0.25% to about 0.30%, about 0.05% to about 0.25%, about 0.075% to about 0.225%, about 0.1% to about 0.2%, about 0.125% to about 0.175%, or a value within one of these ranges. Specific examples may include about 0.05%, about 0.1%, about 0.15%, about 0.2%, about 0.25%, about 0.3%, about 0.35%, about 0.4%, about 0.45%, about 0.5%, about 0.2%, about 0.225%, about 0.25%, about 0.275%, about 0.3%, about 0.325%, about 0.35%, about 0.375%, about 0.4%, about 0.425%, about 0.45%, about 0.475%, about 0.5%, or a range between any two of these values. In certain embodiments of the hydrogel formulation the one or more pH adjusters is in an amount of about 0.26%. The foregoing all represent weight percentages of embodiments of the hydrogel formulations.

In some embodiments of the hydrogel formulation, the propanediol is in an amount of about 1% to about 10%, about 2% to about 10%, about 3% to about 10%, about 4% to about 10%, about 5% to about 10%, about 6% to about 10%, about 7% to about 10%, about 8% to about 10%, about 9% to about 10%, about 1% to about 9%, about 1% to about 8%, about 1% to about 7%, about 1% to about 6%, about 1% to about 5%, about 1% to about 4%, about 1% to about 3%, about 1% to about 2%, about 2% to about 9%, about 3% to about 8%, about 4% to about 7%, about 5% to about 6%, or a value within one of these ranges. Specific examples may include about 1%, about 2%, about 3%, about 4%, about 5%, about 6%, about 7%, about 8%, about 9%, about 10%, or a range between any two of these values. In certain embodiments of the hydrogel formulation the propanediol is in an amount of about 5%. In certain embodiments of the hydrogel formulation the propanediol is in an amount of about 4%. The foregoing all represent weight percentages of embodiments of the hydrogel formulations.

In some embodiments of the hydrogel formulation, the disodium edetate dihydrate is in an amount of about 0.05% to about 0.5%, about 0.1% to about 0.5%, about 0.15% to about 0.5%, about 0.2% to about 0.5%, about 0.25% to about 0.5%, about 0.3% to about 0.5%, about 0.35% to about 0.5%, about 0.4% to about 0.5%, about 0.45% to about 0.5%, about 0.05% to about 0.45%, about 0.05% to about 0.4%, about 0.05% to about 0.35%, about 0.05% to about 0.3%, about 0.05% to about 0.25%, about 0.05% to about 0.2%, about 0.05% to about 0.15%, about 0.05% to about 0.1%, about 0.1% to about 0.45%, about 0.15% to about 0.4%, about 0.2% to about 0.35%, about 0.25% to about 0.30%, about 0.05% to about 0.25%, about 0.075% to about 0.225%, about 0.1% to about 0.2%, about 0.125% to about 0.175%, or a value within one of these ranges. Specific examples may include about 0.05%, about 0.1%, about 0.15%, about 0.2%, about 0.25%, about 0.3%, about 0.35%, about 0.4%, about 0.45%, about 0.5%, about 0.2%, about 0.225%, about 0.25%, about 0.275%, about 0.3%, or a range between any two of these values. In certain embodiments of the hydrogel formulation the disodium edetate dihydrate is in an amount of about 0.15%. In certain embodiments of the hydrogel formulation the disodium edetate dihydrate is in an amount of about 0.10%. The foregoing all represent weight percentages of embodiments of the hydrogel formulations.

In some embodiments of the hydrogel formulation, the PHOSAL® 50 PG (phosphatidylcholine, lysophosphatidylcholine, propylene glycol, sunflower seed oil glycerides, ethanol, soya fatty acids, ascorbyl palmitate, D,L-α-tocopherol) is in an amount of about 0.5% to about 5%, about 1% to about 3%, 0.5% to about 2%, about 0.05% to about 0.2%, about 0.25% to about 1.25%, about 0.01% to about 0.1%, about 0.001% to about 0.01%, about 0.005% to about 0.02%, or a value within one of these ranges. Specific examples may include about 0.001%, about 0.004%, about 0.005%, about 0.01%, about 0.02%, about 0.03%, about 0.04%, about 0.05%, about 0.1%, about 0.4%, about 0.5%, about 0.6%, about 0.7%, about 0.8%, about 0.9%, about 1%, about 2%, about 3%, or a range between any two of these values. In certain embodiments of the hydrogel formulation the PHOSAL® 50 PG (phosphatidylcholine, lysophosphatidylcholine, propylene glycol, sunflower seed oil glycerides, ethanol, soya fatty acids, ascorbyl palmitate, D,L-α-tocopherol) is in an amount of about 2%. The foregoing all represent weight percentages of embodiments of the hydrogel formulations.

In some embodiments of the hydrogel formulation, the methylparaben is in an amount of about 0.05% to about 0.5%, about 0.1% to about 0.5%, about 0.15% to about 0.5%, about 0.2% to about 0.5%, about 0.25% to about 0.5%, about 0.3% to about 0.5%, about 0.35% to about 0.5%, about 0.4% to about 0.5%, about 0.45% to about 0.5%, about 0.05% to about 0.45%, about 0.05% to about 0.4%, about 0.05% to about 0.35%, about 0.05% to about 0.3%, about 0.05% to about 0.25%, about 0.05% to about 0.2%, about 0.05% to about 0.15%, about 0.05% to about 0.1%, about 0.1% to about 0.45%, about 0.15% to about 0.4%, about 0.2% to about 0.35%, about 0.25% to about 0.30%, about 0.05% to about 0.25%, about 0.075% to about 0.225%, about 0.1% to about 0.2%, about 0.125% to about 0.175%, or a value within one of these ranges. Specific examples may include about 0.05%, about 0.1%, about 0.15%, about 0.2%, about 0.25%, about 0.3%, about 0.35%, about 0.4%, about 0.45%, about 0.5%, about 0.2%, about 0.225%, about 0.25%, about 0.275%, about 0.3%, or a range between any two of these values. In certain embodiments of the hydrogel formulation the methylparaben is in an amount of about 0.15%. In certain embodiments of the hydrogel formulation the methylparaben is in an amount of about 0.1%. The foregoing all represent weight percentages of embodiments of the hydrogel formulations.

In some embodiments of the hydrogel formulation, the propylparaben is in an amount of about 0.005% to about 0.05%, about 0.01% to about 0.05%, about 0.015% to about 0.05%, about 0.02% to about 0.05%, about 0.025% to about 0.05%, about 0.03% to about 0.05%, about 0.035% to about 0.05%, about 0.04% to about 0.05%, about 0.045% to about 0.05%, about 0.005% to about 0.045%, about 0.005% to about 0.04%, about 0.005% to about 0.035%, about 0.005% to about 0.03%, about 0.005% to about 0.025%, about 0.005% to about 0.02%, about 0.005% to about 0.015%, about 0.005% to about 0.01%, about 0.01% to about 0.045%, about 0.02% to about 0.04%, about 0.025% to about 0.035%, about 0.02% to about 0.04%, about 0.015% to about 0.045%, or a value within one of these ranges. Specific examples may include about 0.005%, about 0.01%, about 0.015%, about 0.02%, about 0.025%, about 0.03%, about 0.035%, about 0.04%, about 0.045%, about 0.05%, or a range between any two of these values. In certain embodiments of the hydrogel formulation the propylparaben is in an amount of about 0.02%. The foregoing all represent weight percentages of embodiments of the hydrogel formulations.

In some embodiments of the hydrogel formulation, the sodium benzoate is in an amount of about 0.005% to about 0.1%, about 0.1% to about 1%, about 0.05% to about 0.5%, or a value within one of these ranges. Specific examples may include about 0.005%, about 0.01%, about 0.02%, about 0.03%, about 0.04%, about 0.05%, about 0.1%, about 0.4%, about 0.45%, about 0.5%, about 0.6%, about 0.7%, about 0.8%, about 0.9%, about 1%, about 2%, about 3%, or a range between any two of these values. In certain embodiments of the hydrogel formulation the sodium benzoate is in an amount of about 0.40%. In certain embodiments of the hydrogel formulation the sodium benzoate is in an amount of about 0.45%. The foregoing all represent weight percentages of embodiments of the hydrogel formulations.

In some embodiments of the hydrogel formulation, the potassium sorbate is in an amount of about 0.005% to about 0.1%, about 0.1% to about 1%, about 0.05% to about 0.5%, or a value within one of these ranges. Specific examples may include about 0.005%, about 0.01%, about 0.02%, about 0.03%, about 0.04%, about 0.05%, about 0.1%, about 0.4%, about 0.45%, about 0.5%, about 0.6%, about 0.7%, about 0.8%, about 0.9%, about 1%, about 2%, about 3%, or a range between any two of these values. In certain embodiments of the hydrogel formulation the potassium sorbate is in an amount of about 0.45%. The foregoing all represent weight percentages of embodiments of the hydrogel formulations.

In some embodiments of the hydrogel formulation, the water is in an amount of about 20% to about 80%, about 25% to about 80%, about 30% to about 80%, about 35% to about 80%, about 40% to about 80%, about 45% to about 80%, about 50% to about 80%, about 55% to about 80%, about 60% to about 80%, about 65% to about 80%, about 70% to about 80%, about 75% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 25% to about 75%, about 30% to about 70%, about 35% to about 65%, about 40% to about 60%, about 45% to about 55%, or a value within one of these ranges. Specific examples may include about 20%, about 25%, about 30%, about 35%, about 40%, about 45%, about 50%, about 55%, about 60%, about 65%, about 60%, about 75%, about 80%, or a range between any two of these values. In certain embodiments of the hydrogel formulation the water is in an amount of about 43.38%. In certain embodiments of the hydrogel formulation the water is in an amount of about 33.38%. In certain embodiments of the hydrogel formulation the water is in an amount of about 40.38%. In certain embodiments of the hydrogel formulation the water is in an amount of about 38.38%. In certain embodiments of the hydrogel formulation the water is in an amount of about 40.7%. In certain embodiments of the hydrogel formulation the water is in an amount of about 39%. The foregoing all represent weight percentages of embodiments of the hydrogel formulations.

In some embodiments of the hydrogel formulation, the dimethicone is in an amount of about 0.5% to about 10%, about 1% to about 10%, about 1.5% to about 10%, about 2% to about 10%, about 2.5% to about 10%, about 3% to about 10%, about 3.5% to about 10%, about 4% to about 10%, about 4.5% to about 10%, about 5% to about 10%, about 5.5% to about 10%, about 6% to about 10%, about 6.5% to about 10%, about 7% to about 10%, about 7.5% to about 10%, about 8% to about 10%, about 8.5% to about 10%, about 9% to about 10%, about 9.5% to about 10%, about 0.5% to about 9.5%, about 0.5% to about 9%, about 0.5% to about 8.5%, about 0.5% to about 8%, about 0.5% to about 7.5%, about 0.5% to about 7%, about 0.5% to about 6.5%, about 0.5% to about 6%, about 0.5% to about 5.5%, about 0.5% to about 5%, about 0.5% to about 4.5%, about 0.5% to about 4%, about 0.5% to about 3.5%, about 0.5% to about 3%, about 0.5% to about 2.5%, about 0.5% to about 2%, about 0.5% to about 1.5%, about 0.5% to about 1%, about 1% to about 9.5%, about 1.5% to about 9%, about 2% to about 8.5%, about 0.5% to about 8%, about 3% to about 7.5%, about 3.5% to about 7%, about 4% to about 6.5%, about 4.5% to about 6%, about 5% to about 5.5%, about 1% to about 5%, about 1.5% to about 4.5%, about 2% to about 4%, about 2.5% to about 3.5%, or a value within one of these ranges. Specific examples may include about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, or a range between any two of these values. In certain embodiments of the hydrogel formulation the dimethicone is in an amount of about 2%. In certain embodiments of the hydrogel formulation the dimethicone is in an amount of about 2.5%. In certain embodiments of the hydrogel formulation the dimethicone is in an amount of about 3%. The foregoing all represent weight percentages of embodiments of the hydrogel formulations.

In some embodiments of the hydrogel formulation, the dimethicone has a viscosity of about 175 cSt to about 525 cSt, about 200 cSt to about 525 cSt, about 225 cSt to about 525 cSt, about 250 cSt to about 525 cSt, about 275 cSt to about 525 cSt, about 300 cSt to about 525 cSt, about 325 cSt to about 525 cSt, about 350 cSt to about 525 cSt, about 375 cSt to about 525 cSt, about 400 cSt to about 525 cSt, about 425 cSt to about 525 cSt, about 450 cSt to about 525 cSt, about 475 cSt to about 525 cSt, about 500 cSt to about 525 cSt, about 175 cSt to about 500 cSt, about 175 cSt to about 475 cSt, about 175 cSt to about 450 cSt, about 175 cSt to about 425 cSt, about 175 cSt to about 400 cSt, about 175 cSt to about 375 cSt, about 175 cSt to about 350 cSt, about 175 cSt to about 325 cSt, about 175 cSt to about 300 cSt, about 175 cSt to about 275 cSt, about 175 cSt to about 250 cSt, about 175 cSt to about 225 cSt, about 175 cSt to about 200 cSt, about 200 cSt to about 500 cSt, about 225 cSt to about 475 cSt, about 250 cSt to about 450 cSt, about 275 cSt to about 425 cSt, about 300 cSt to about 400 cSt, about 325 cSt to about 375 cSt, or a value within one of these ranges. Specific examples may include about 175 cSt, about 200 cSt, about 225 cSt, about 250 cSt, about 275 cSt, about 300 cSt, about 325 cSt, about 350 cSt, about 375 cSt, about 400 cSt, about 425 cSt, about 450 cSt, about 475 cSt, about 500 cSt, about 525 cSt, or a range between any two of these values. In certain embodiments of the hydrogel formulation the dimethicone has a viscosity of about 350 cSt.

In some embodiments of the hydrogel formulation, the caprylic/capric triglyceride is in an amount of about 1% to about 10%, about 2% to about 10%, about 3% to about 10%, about 4% to about 10%, about 5% to about 10%, about 6% to about 10%, about 7% to about 10%, about 8% to about 10%, about 9% to about 10%, about 1% to about 9%, about 1% to about 8%, about 1% to about 7%, about 1% to about 6%, about 1% to about 5%, about 1% to about 4%, about 1% to about 3%, about 1% to about 2%, about 2% to about 9%, about 3% to about 8%, about 4% to about 7%, about 5% to about 6%, or a value within one of these ranges. Specific examples may include about 1%, about 2%, about 3%, about 4%, about 5%, about 6%, about 7%, about 8%, about 9%, about 10%, or a range between any two of these values. In certain embodiments of the hydrogel formulation the caprylic/capric triglyceride is in an amount of about 5%. In certain embodiments of the hydrogel formulation the caprylic/capric triglyceride is in an amount of about 7%. The foregoing all represent weight percentages of embodiments of the hydrogel formulations.

In some embodiments of the hydrogel formulation, the SEPINEO™ P 600 (acrylamide/sodium acryloyldimethyl taurate copolymer/isohexadecane/polysorbate 80) is in an amount of about 0.5% to about 10%, about 1% to about 10%, about 1.5% to about 10%, about 2% to about 10%, about 2.5% to about 10%, about 3% to about 10%, about 3.5% to about 10%, about 4% to about 10%, about 4.5% to about 10%, about 5% to about 10%, about 5.5% to about 10%, about 6% to about 10%, about 6.5% to about 10%, about 7% to about 10%, about 7.5% to about 10%, about 8% to about 10%, about 8.5% to about 10%, about 9% to about 10%, about 9.5% to about 10%, about 0.5% to about 9.5%, about 0.5% to about 9%, about 0.5% to about 8.5%, about 0.5% to about 8%, about 0.5% to about 7.5%, about 0.5% to about 7%, about 0.5% to about 6.5%, about 0.5% to about 6%, about 0.5% to about 5.5%, about 0.5% to about 5%, about 0.5% to about 4.5%, about 0.5% to about 4%, about 0.5% to about 3.5%, about 0.5% to about 3%, about 0.5% to about 2.5%, about 0.5% to about 2%, about 0.5% to about 1.5%, about 0.5% to about 1%, about 1% to about 9.5%, about 1.5% to about 9%, about 2% to about 8.5%, about 0.5% to about 8%, about 3% to about 7.5%, about 3.5% to about 7%, about 4% to about 6.5%, about 4.5% to about 6%, about 5% to about 5.5%, about 1% to about 5%, about 1.5% to about 4.5%, about 2% to about 4%, about 2.5% to about 3.5%, or a value within one of these ranges. Specific examples may include about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, or a range between any two of these values. In certain embodiments of the hydrogel formulation the SEPINEO™ P 600 (acrylamide/sodium acryloyldimethyl taurate copolymer/isohexadecane/polysorbate 80) is in an amount of about 3.3%. In certain embodiments of the hydrogel formulation the SEPINEO™ P 600 (acrylamide/sodium acryloyldimethyl taurate copolymer/isohexadecane/ polysorbate 80) is in an amount of about 4.0%. The foregoing all represent weight percentages of embodiments of the hydrogel formulations.

In some embodiments of the hydrogel formulation, the trolamine is in an amount of about 0.05% to about 0.5%, about 0.1% to about 0.5%, about 0.15% to about 0.5%, about 0.2% to about 0.5%, about 0.25% to about 0.5%, about 0.3% to about 0.5%, about 0.35% to about 0.5%, about 0.4% to about 0.5%, about 0.45% to about 0.5%, about 0.05% to about 0.45%, about 0.05% to about 0.4%, about 0.05% to about 0.35%, about 0.05% to about 0.3%, about 0.05% to about 0.25%, about 0.05% to about 0.2%, about 0.05% to about 0.15%, about 0.05% to about 0.1%, about 0.1% to about 0.45%, about 0.15% to about 0.4%, about 0.2% to about 0.35%, about 0.25% to about 0.30%, about 0.05% to about 0.25%, about 0.075% to about 0.225%, about 0.1% to about 0.2%, about 0.125% to about 0.175%, or a value within one of these ranges. Specific examples may include about 0.05%, about 0.1%, about 0.15%, about 0.2%, about 0.25%, about 0.3%, about 0.35%, about 0.4%, about 0.45%, about 0.5%, about 0.2%, about 0.225%, about 0.25%, about 0.275%, about 0.3%, about 0.325%, about 0.35%, about 0.375%, about 0.4%, about 0.425%, about 0.45%, about 0.475%, about 0.5%, or a range between any two of these values. In certain embodiments of the hydrogel formulation the trolamine is in an amount of about 0.26%. The foregoing all represent weight percentages of embodiments of the hydrogel formulations.

In some embodiments of the hydrogel formulation, the hydrogel formulation has a pH of about 3.0 to about 7.0, about 3.5 to about 7.0, about 4.0 to about 7.0, about 4.5 to about 7.0, about 5.0 to about 7.0, about 5.5 to about 7.0, about 6.0 to about 7.0, about 6.5 to about 7.0, about 3.0 to about 6.5, about 3.0 to about 6.0, about 3.0 to about 5.5, about 3.0 to about 5, about 3.0 to about 4.5, about 3.0 to about 4, about 3.0 to about 3.5, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, or a range between any two of these values. In certain embodiments of the hydrogel formulation, the hydrogel formulation has a pH of about 4.0 to about 6.7. In certain embodiments of the hydrogel formulation, the hydrogel formulation has a pH of about 3.0 to about 4.0. In certain embodiments of the hydrogel formulation the hydrogel formulation has a pH of about 5.5 to about 6.5.

In some embodiments, the hydrogel formulation does not contain more than about 2 wt % monohydroxyalcohol.

In some embodiments, the hydrogel formulation does not contain sodium cromoglycate.

In some embodiments of the hydrogel formulation, the glycerin is in an amount of about 1% to about 5%, about 1.5% to about 5%, about 2% to about 5%, about 2.5% to about 5%, about 3% to about 5%, about 3.5% to about 5%, about 4% to about 5%, about 4.5% to about 5%, about 1% to about 4.5%, about 1% to about 4%, about 1% to about 3.5%, about 1% to about 3%, about 1% to about 2.5%, about 1% to about 2%, about 1% to about 1.5%, about 1.5% to about 4.5%, about 2% to about 4%, about 2.5% to about 3.5%, or a value within one of these ranges. Specific examples may include about 1%, about 1.5%, about 2%, about 2.5%, about 3%, about 3.5%, about 4%, about 4.5%, about 5%, or a range between any two of these values. In certain embodiments of the hydrogel formulation the glycerin is in an amount of about 3%. The foregoing all represent weight percentages of embodiments of the hydrogel formulations.

In some embodiments of the hydrogel formulation, the sodium phosphate dibasic heptahydrate is in an amount of about 1% to about 3%, about 1.5% to about 3%, about 2% to about 3%, about 2.5% to about 3%, about 1% to about 2.5%, about 1% to about 2%, about 1% to about 1.5%, about 1.5% to about 2.5%, or a value within one of these ranges. Specific examples may include about 1%, about 1.5%, about 2%, about 2.5%, about 3%, or a range between any two of these values. In certain embodiments of the hydrogel formulation the sodium phosphate dibasic heptahydrate is in an amount of about 2%. The foregoing all represent weight percentages of embodiments of the hydrogel formulations.

In some embodiments of the hydrogel formulation, the sodium phosphate monobasic is in an amount of about 0.1% to about 0.4%, about 0.15% to about 0.4%, about 0.2% to about 0.4%, about 0.25% to about 0.4%, about 0.3% to about 0.4%, about 0.35% to about 0.4%, about 0.1% to about 0.35%, about 0.1% to about 0.3%, about 0.1% to about 0.25%, about 0.1% to about 0.2%, about 0.1% to about 0.15%, about 0.15% to about 0.35%, about 0.2% to about 0.3%, or a value within one of these ranges. Specific examples may include about 0.1%, about 0.15%, about 0.2%, about 0.25%, about 0.3%, about 0.35%, about 0.4%, or a range between any two of these values. In certain embodiments of the hydrogel formulation the sodium phosphate monobasic is in an amount of about 0.26%. The foregoing all represent weight percentages of embodiments of the hydrogel formulations.

In some embodiments of the hydrogel formulation, the sodium hexametaphosphate is in an amount of about 0.005% to about 0.02%, about 0.01% to about 0.02%, about 0.015% to about 0.02%, about 0.005% to about 0.015%, about 0.005% to about 0.01%, about 0.01% to about 0.015%, or a value within one of these ranges. Specific examples may include about 0.005%, about 0.01%, about 0.015%, about 0.02%, or a range between any two of these values. In certain embodiments of the hydrogel formulation the sodium hexametaphosphate is in an amount of about 0.01%. The foregoing all represent weight percentages of embodiments of the hydrogel formulations.

In some embodiments of the hydrogel formulation, the medium chain triglycerides are in an amount of about 1% to about 6%, about 1.5% to about 6%, about 2% to about 6%, about 2.5% to about 6%, about 3% to about 6%, about 3.5% to about 6%, about 4% to about 6%, about 4.5% to about 6%, about 5% to about 6%, about 5.5% to about 6%, about 1% to about 5.5%, about 1% to about 5%, about 1% to about 4.5%, about 1% to about 4%, about 1% to about 3.5%, about 1% to about 3%, about 1% to about 2.5%, about 1% to about 2%, about 1% to about 1.5%, about 1.5% to about 4.5%, about 2% to about 4%, about 2.5% to about 3.5%, or a value within one of these ranges. Specific examples may include about 1%, about 1.5%, about 2%, about 2.5%, about 3%, about 3.5%, about 4%, about 4.5%, about 5%, about 5.5%, about 6%, or a range between any two of these values. In certain embodiments of the hydrogel formulation the medium chain triglycerides are in an amount of about 4%. The foregoing all represent weight percentages of embodiments of the hydrogel formulations.

Polydispersity Index (PDI) is used to measure the breadth of the molecular weight distribution of AB-101. PDI is used to indicate distribution of polymer chain molecular weights in a given polymer, as the PDI value increases the heterogeneity in cross-linking, network formation, chain length, branching, hyper branching is increased and will have a more random arrangement. PDI is an important measure to characterize the unique compositional nature of AB-101 or other *Croton lechleri* derived compositions. In any of the embodiments disclosed herein, the latex of *Croton lechleri*, preferably filtered latex of *Croton lechleri*, preferably filtered latex of *Croton lechleri* Müll.Arg has a PDI of about 0.5 to about 0.85, about 0.55 to about 0.85, about 0.6 to about 0.85, about 0.65 to about 0.85, about 0.7 to about 0.85, about 0.75 to about 0.85, about 0.8 to about 0.85, about 0.5 to about 0.8, about 0.5 to about 0.75, about 0.5 to about 0.7, about 0.5 to about 0.65, about 0.5 to about 0.6, about 0.5 to about 0.55, or a value within one of these ranges. Specific examples may include about 0.5, about 0.55, about 0.6, about 0.65, about 0.7, about 0.75, about 0.8, about 0.85, or a range between any two of these values. In some embodiments, the latex of *Croton lechleri*, preferably filtered latex of *Croton lechleri*, preferably filtered latex of *Croton lechleri* Müll.Arg has a PDI of about 0.81.

In some embodiments, the hydrogel formulation is as described in Table C:

TABLE C

| Ingredient Name | INCI Name/Technical Name | wt % of Component | wt % of Drug Product Formula | wt % of Drug Product Formula | Function | CAS # |
|---|---|---|---|---|---|---|
| ZEMEA ® USP | Propanediol | 100.0% | 5.00% | 5.00% | Preservative-boosting humectant | |
| EDETATE DISODIUM USP DEHYDRATE | Disodium EDTA | 100.0% | 0.10% | 0.10% | Chelating agent | 6381926 |
| PHOSAL ® 50 PG | Phosphatidylcholine | n.l.t. 50.0% | 2.00% | 1.00% | Dispersant/ Co-emulsifier | 8002435 |
| | Lysophosphatidylcholine | n.m.t. 6.0% | | 0.12% | | |
| | Propylene Glycol | 33.8%-41.2% | | 0.676%-0.824% | | 57556 |
| | Sunflower Seed Oil Glycerides | | | | | |
| | Ethanol | 1.5%-2.5% | | 0.03%-0.05% | | |
| | Soya Fatty Acids | | | | | |
| | Ascorbyl Palmitate | n.m.t. 0.2% | | 0.004% | | |
| | D,L-α-tocopherol | n.m.t. 0.3% | | 0.01% | | 137666 |
| METHYLPARABEN NF | Methyl paraben | 100.0% | 0.10% | 0.10% | Preservative | 99763 |
| PROPYLPARABEN NF | Propyl paraben | 100.0% | 0.02% | 0.02% | Preservative | 94133 |
| Filtered latex of *Croton lechleri* (AB-101 pharmaceutical grade) | *Croton Lechleri* | 100.0% | 40.00% | 40.00% | | |
| PURIFIED WATER | Water | 100.0% | 40.70% | 40.70% | | |
| DOW CORNING ® Q7 9120 (PHARMACEUTICAL GRADE) | Dimethicone 350 | 100.0% | 2.00% | 2.00% | Skin Protectant/ Emollient | 9006659 |
| LABRAFAC ™ WL1349 | Medium-Chain Triglycerides | 100.0% | 5.00% | 5.00% | Emollient | 438544491 |
| SEPINEO ™ P600 | Acrylamide/Sodium Aryyloyldimethyltaurate Copolymer | 35-40% | 4.00% | 1.40%-1.60% | Thickening/ Stabilizing/ Emulsifying/ Texturizing | 38193-60-1 |
| | Isohexadecane | 20-25% | | 0.80%-1.00% | | 93685-80-4 |
| | Polysorbate 80 | 5-10% | | 0.20%-0.40% | | |
| | Other | 25%-40% | | 1.00%-1.60% | | 9005-65-6 |
| SODIUM BENZOATE NF | Sodium benzoate | 100.0% | 0.40% | 0.40% | Preservative | 532321 |
| POTASSIUM SORBATE NF | Potassium sorbate | 100.0% | 0.45% | 0.45% | Preservative | 24634615 |
| TROLAMINE NF | Trolamine | 100.0% | 0.26% | 0.26% | pH Adjuster | 102716 |

In some embodiments, the hydrogel formulation is as described in Table D:

TABLE D

| Ingredient Name | INCI Name/Technical Name | wt % of Component | wt % of Drug Product Formula | wt % of Drug Product Formula | Function | CAS # |
|---|---|---|---|---|---|---|
| ZEMEA ® USP | Propanediol | 100.0% | 4.0028% | 4.0028% | Preservative-boosting humectant | |
| EDETATE DISODIUM USP DEHYDRATE | Disodium EDTA | 100.0% | 0.1008% | 0.1008% | Chelating agent | 6381926 |

TABLE D-continued

| Ingredient Name | INCI Name/Technical Name | wt % of Component | wt % of Drug Product Formula | wt % of Drug Product Formula | Function | CAS # |
|---|---|---|---|---|---|---|
| PHOSAL ® 50 PG | Phosphatidylcholine | n.l.t. 50.0% | 2.0034% | 1.0017% | Dispersant/ Co-emulsifier | 8002435 |
| | Lysophosphatidylcholine | n.m.t. 6.0% | | 0.120204% | | |
| | Propylene Glycol | 33.8%-41.2% | | 0.6771492%-0.8254008% | | 57556 |
| | Sunflower Seed Oil Glycerides | | | | | |
| | Ethanol | 1.5%-2.5% | | 0.030051%-0.050085% | | |
| | Soya Fatty Acids | | | | | |
| | Ascorbyl Palmitate | n.m.t. 0.2% | | 0.0040068% | | |
| | D,L-α-tocopherol | n.m.t. 0.3% | | 0.010017% | | 137666 |
| METHYLPARABEN NF | Methyl paraben | 100.0% | 0.10045% | 0.10045% | Preservative | 99763 |
| PROPYLPARABEN NF | Propyl paraben | 100.0% | 0.02025% | 0.02025% | Preservative | 94133 |
| Filtered latex of *Croton lechleri* (AB-101 pharmaceutical grade) | *Croton Lechleri* | 100.0% | 40.02025% | 40.02025% | | |
| PURIFIED WATER | Water | 100.0% | 39.3353% | 39.3353% | | |
| DOW CORNING ® Q7 9120 (PHARMACEUTICAL GRADE) | Dimethicone 350 | 100.0% | 2.5038% | 2.5038% | Skin Protectant/ Emollient | 9006659 |
| LABRAFAC ™ WL1349 | Medium-Chain Triglycerides | 100.0% | 7.0049% | 7.0049% | Emollient | 438544491 |
| SEPINEO ™ P 600 | Acrylamide/Sodium Acryloyldimethyltaurate Copolymer | 35-40% | 4.0071% | 1.402485%-1.60284% | Thickening/ Stabilizing/ Emulsifying/ Texturizing | 38193-60-1 |
| | Isohexadecane | 20-25% | | 0.80142%-1.001775% | | 93685-80-4 |
| | Polysorbate 80 | 5-10% | | 0.200355%-0.40071% | | |
| | Other | 25%-40% | | 1.001775%-1.60284% | | 9005-65-6 |
| SODIUM BENZOATE NF | Sodium benzoate | 100.0% | 0.4503% | 0.4503% | Preservative | 532321 |
| POTASSIUM SORBATE NF | Potassium solbate | 100.0% | 0.4506% | 0.4506% | Preservative | 24634615 |

In some embodiments, the hydrogel formulation is as described in Table E:

TABLE E

| Ingredient Name | INCI Name/Technical Name | wt % of Component | wt % of Drug Product Formula | wt % of Drug Product Formula | Function | CAS # |
|---|---|---|---|---|---|---|
| ZEMEA ® USP | Propanediol | 100.0% | 3%-5% | 3%-5% | Preservative-boosting humectant | |
| EDETATE DISODIUM USP DIHYDRATE | Disodium EDTA | 100.0% | 0.05%-0.2% | 0.05%-0.2% | Chelating agent | 6381926 |
| PHOSAL ® 50 PG | Phosphatidylcholine | n.l.t. 50.0% | 1%-3% | 0.5%-1.5% | Dispersant/ Co-emulsifier | 8002435 |
| | Lysophosphatidylcholine | n.m.t. 6.0% | | 0.06%-0.18% | | |
| | Propylene Glycol | 33.8%-41.2% | | 0.338%-1.236% | | 57556 |
| | Sunflower Seed Oil Glycerides | | | | | |
| | Ethanol | 1.5%-2.5% | | 0.015%-0.0.075% | | |
| | Soya Fatty Acids | | | | | |
| | Ascorbyl Palmitate | n.m.t. 0.2% | | 0.002%-0.006% | | |
| | D,L-α-tocopherol | n.m.t. 0.3% | | 0.005%-0.015% | | 137666 |
| METHYLPARABEN NF | Methyl paraben | 100.0% | 0.05%-0.15% | 0.05%-0.15% | Preservative | 99763 |
| PROPYLPARABEN NF | Propyl paraben | 100.0% | 0.01%-0.03% | 0.01%-0.03% | Preservative | 94133 |
| Filtered latex of *Croton lechleri* (AB-101 pharmaceutical grade) | *Croton Lechleri* | 100.0% | 20%-60% | 20%-60% | | |

TABLE E-continued

| Ingredient Name | INCI Name/Technical Name | wt % of Component | wt % of Drug Product Formula | wt % of Drug Product Formula | Function | CAS # |
|---|---|---|---|---|---|---|
| PURIFIED WATER | Water | 100.0% | 30%-65% | 30%-65% | | 9006659 |
| DOW CORNING ® Q7 9120 (PHARMACEUTICAL GRADE) | Dimethicone 350 | 100.0% | 1%-3% | 1%-3% | Skin Protectant/ Emollient | |
| LABRAFAC ™ WL1349 | Medium-Chain Triglycerides | 100.0% | 2.5%-10% | 2.5%-10% | Emollient | 438544491 |
| SEPINEO ™ P 600 | Acrylamide/Sodium Acryloyldimethyltaurate Copolymer | 35-40% | | 1.05%-2% | Thickening/ Stabilizing/ Emulsifying/ Texturizing | 38193-60-1 |
| | Isohexadecane | 20-25% | 3%-5% | 0.6%-1.25% | | 93685-80-4 |
| | Polysorbate 80 | 5-10% | | 0.15%-0.5% | | |
| | Other | 25%-40% | | 0.75%-2% | | 9005-65-6 |
| SODIUM BENZOATE NF | Sodium benzoate | 100.0% | 0.2%-0.7% | 0.2%-0.7% | Preservative | 532321 |
| POTASSIUM SORBATE NF | Potassium sorbate | 100.0% | 0.2%-0.7% | 0.2%-0.7% | Preservative | 24634615 |
| TROLAMINE NF | Trolamine | 100.0% | 0%-0.4% | 0%-0.4% | pH Adjuster | 102716 |

In some embodiments, the hydrogel formulation is as described in Table F:

TABLE F

| Ingredient Name | INCI Name/Technical Name | wt % of Component | wt % of Drug Product Formula | wt % of Drug Product Formula | Function | CAS # |
|---|---|---|---|---|---|---|
| Glycerin USP (Natural) | Glycerin | 100.0% | 3% | 3% | | |
| METHYLPARABEN NF | Methyl paraben | 100.0% | 0.2% | 0.2% | Preservative | 99763 |
| PROPYLPARABEN NF | Propyl paraben | 100.0% | 0.02% | 0.02% | Preservative | 94133 |
| PURIFIED WATER | Water | 100.0% | 46.51% | 46.51% | | |
| Sodium Phosphate Dibasic USP Heptahydrate | Sodium Phosphate Dibasic Heptahydrate | 100.0% | 2% | 2% | Deflocculant | |
| Sodium Phosphate Monobasic USP Anhydrous | Sodium Phosphate Monobasic | 100.0% | 0.26% | 0.26% | Deflocculant | |
| Glass H, Long Chain Powder FCC | Sodium Hexametaphosphate | 100.0% | 0.01% | 0.01% | Deflocculant | |
| LABRAFAC ™ WL1349 | Medium-Chain Triglycerides | 100.0% | 4% | 4% | Emollient | 438544491 |
| SEPINEO ™ P 600 | Acrylamide/Sodium Acryloyldimethyltaurate Copolymer | 35-40% | 4% | 1.05%-2% | Thickening/ Stabilizing/ Emulsifying/ Texturizing | 38193-60-1 |
| | Isohexadecane | 20-25% | | 0.6%-1.25% | | 93685-80-4 |
| | Polysorbate 80 | 5-10% | | 0.15%-0.5% | | |
| | Other | 25%-40% | | 0.75%-2% | | 9005-65-6 |
| Filtered latex of *Croton lechleri* (AB-101 pharmaceutical grade) | *Croton Lechleri* | 100.0% | 40% | 40% | | |

The hydrogel formulation of AB-101 as described and claimed herein is a plant sourced material that meets the criteria of being consistently reproducible between batch to batch and reliably delivers the desired health benefits via topical application that may be used in a hydrogel formulation. It can be used to treat a dermatological condition. Plant sourced materials face the challenge that changes in environmental weather, climate, rainfall, time of harvest (via season, time of day or month), changes in geography, longitude location, latitude location, altitude, changes in soil condition, harvesting protocols and many additional conditions can alter the characteristics of the plant that could impact quality. This can impact the plant's bioactivity resulting in inconsistency in achieving desired performance outcome. This creates a challenge in defining a pharmaceutical grade of dragon's blood to deliver consistent and reproducible therapeutic benefits. This is further compounded by the wide variety of the different species called dragon's blood. For example, phytochemical and anti-staphylococcal biofilm assessment of *Dracaena draco* L. Spp. *draco* resin, referred as dragon's blood, is "inactive in the maximum tested concentration of 1000 mcg/ml against free living staphylococci." In contrast, AB-101 (latex of *Croton lechleri*, preferably filtered latex of *Croton lechleri*, preferably filtered latex of *Croton lechleri* Müll.Arg. with the appropriate levels of gallocatechin, epigallocatechin, catechin, epicatechin, taspine, and dimethylcedrusin) is effective against *Staphylococcus* specifically methicillin-susceptible *Staphylococcus aureus* (MS SA) or the shorten nomenclature staph bacteria and in particular methicillin-resistant *Staphylococcus aureus* (MRSA) and in particular Mupirocin resistant MRSA. The generic name of the *Croton lechleri* resin, ie, dragon's blood, or Sangre de grado, creates confusion in defining a plant-derived pharmaceutical and demonstrates that not all *Croton lechleri* plants are the same, nor do they provide similar benefits.

The benefits of AB-101, filtered or unfiltered latex of *Croton lechleri*, preferably filtered latex of *Croton lechleri*, preferably filtered latex of *Croton lechleri* Müll.Arg., is its ability to deliver consistent results for treating the pathogens between batch to batch in spite of all the confounding conditions. The challenge in using the whole latex is to identify the compounds that deliver performance based on the many bio-active compounds comprising the latex. Even within the same species, grown in a similar location, there are variations in chemical content and bioactivity of the whole latex that unexpectedly varies in its ability to fight and kill pathogens.

Methodology that can identify the whole latex is effective by having an assay that determines when a batch meets the predetermined performance criteria. Having a unique analytical and microbiological assay enables the ability to identify which batch of filtered or unfiltered latex of *Croton lechleri*, preferably filtered latex of *Croton lechleri*, preferably filtered latex of *Croton lechleri* Müll.Arg, has the combination of components that will consistently deliver the desired outcome.

AB-101 botanical raw material (BRM) is a complex botanical product that is a latex of *Croton lechleri*, preferably filtered latex of *Croton lechleri*, preferably filtered latex of *Croton lechleri* Müll.Arg. that contains certain marker compounds (catechin, gallocatechin, epicatechin, epigallocatechin, taspine, and dimethylcedrusin) in specified amounts (see Table 1a). Utilization of liquid chromatography with tandem mass spectrometry (LC-MS/MS) can be used to characterize the existence and levels of such marker compounds for batch to batch consistency and repeatable performance of AB-101. Marker compounds in AB-101 BRM include the proanthocyanidins: catechin, gallocatechin, epicatechin, and epigallocatechin, the alkaloid taspine, and the lignin dimethylcedrusin.

The published and accepted taxonomic classification of *Croton lechleri* is the following (van Ee & Berry, 2011, Riina et al, 2009, The Plant List, 2012, The Angiosperm Phylogeny Group, 2009):

Division: Streptophyta
  Class: Equisetopsida
    Subclass: Magnoliidae
      Order: Malpighiales
        Family: Euphorbiaceae
          Genus: *Croton*
            Subgenus *Adenophylli*
              Section: Cyclostigma
                Subsection: Cyclostigma
                  Species: *Croton lechleri* Müll.Arg.

Biodiversity of botanicals plays a major role in constituent chemical compound characterization. Chemical compounds utilized for as important batch to batch consistency of AB-101 need to 1) demonstrate antimicrobial or cicatrizant properties, 2) be present in AB-101, and 3) be detectable using analytical techniques. Using these criteria, the analytical efforts focused on 3 classes of compounds: polyphenols (proanthocyanidins) alkaloids (taspine) and lignin (dimethylcedrusin). Within the proanthocyanidin class, 4 specific compounds were focused on: catechin, epicatechin, gallocatechin, and epigallocatechin. The compound of importance within the alkaloid class is taspine. Finally, the compound of importance within the lignin class is dimethylcedrusin. Each of these compounds fulfills the three required elements detailed above. The following are the chemical structures of the 6 compounds utilized as important markers for batch to batch consistency of AB-101.

Proanthocyanidins

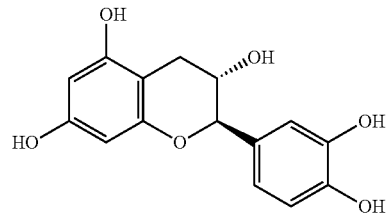

(+) catechin

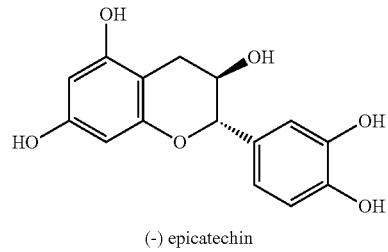

(-) epicatechin

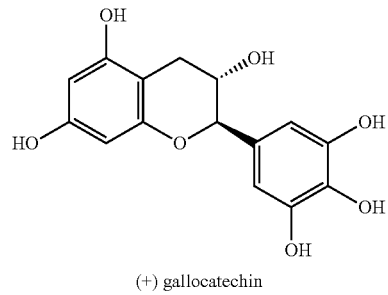

(+) gallocatechin

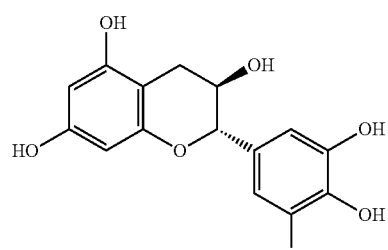

(-) epigallocatechin

Alkaloid

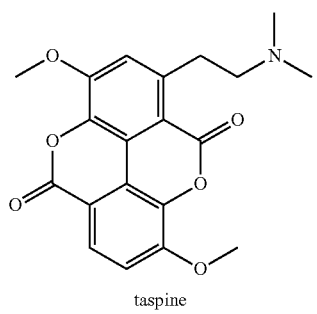

taspine

Lignin

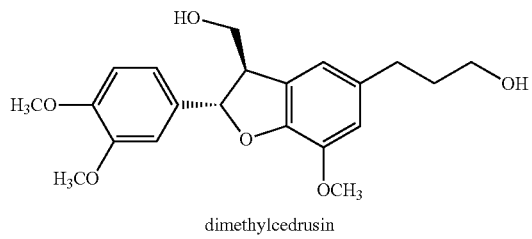

dimethylcedrusin

For characterization studies, AB-101 extract was lyophilized and the lyophilized powder was subjected to three different extraction methods.

Method 1—Ultrasonic polyphenol extraction. The lyophilized AB-101 extract was dissolved into methanol. The resultant emulsion was then subjected to sonication for 10 minutes followed by centrifugation to remove particulates for 5 minutes. The supernatant was then subjected to LC-MS/MS analysis.

Method 2—Soxhlet extraction. The lyophilized AB-101 extract was subjected to a Soxhlet extraction with 80% ethanol. The ethanol was removed via a rotary evaporator. The resultant material was then subjected re-suspended in ethanol then subjected to LC-MS/MS analysis.

Method 3—Polyphenol extraction. The lyophilized AB-101 extract was incubated with methanol overnight at room temperature and in the dark. The supernatant was then filtered using Whatman filters, dried, and then re-suspended in methanol. The resultant material was then subjected to LC-MS/MS analysis.

Figure 6:
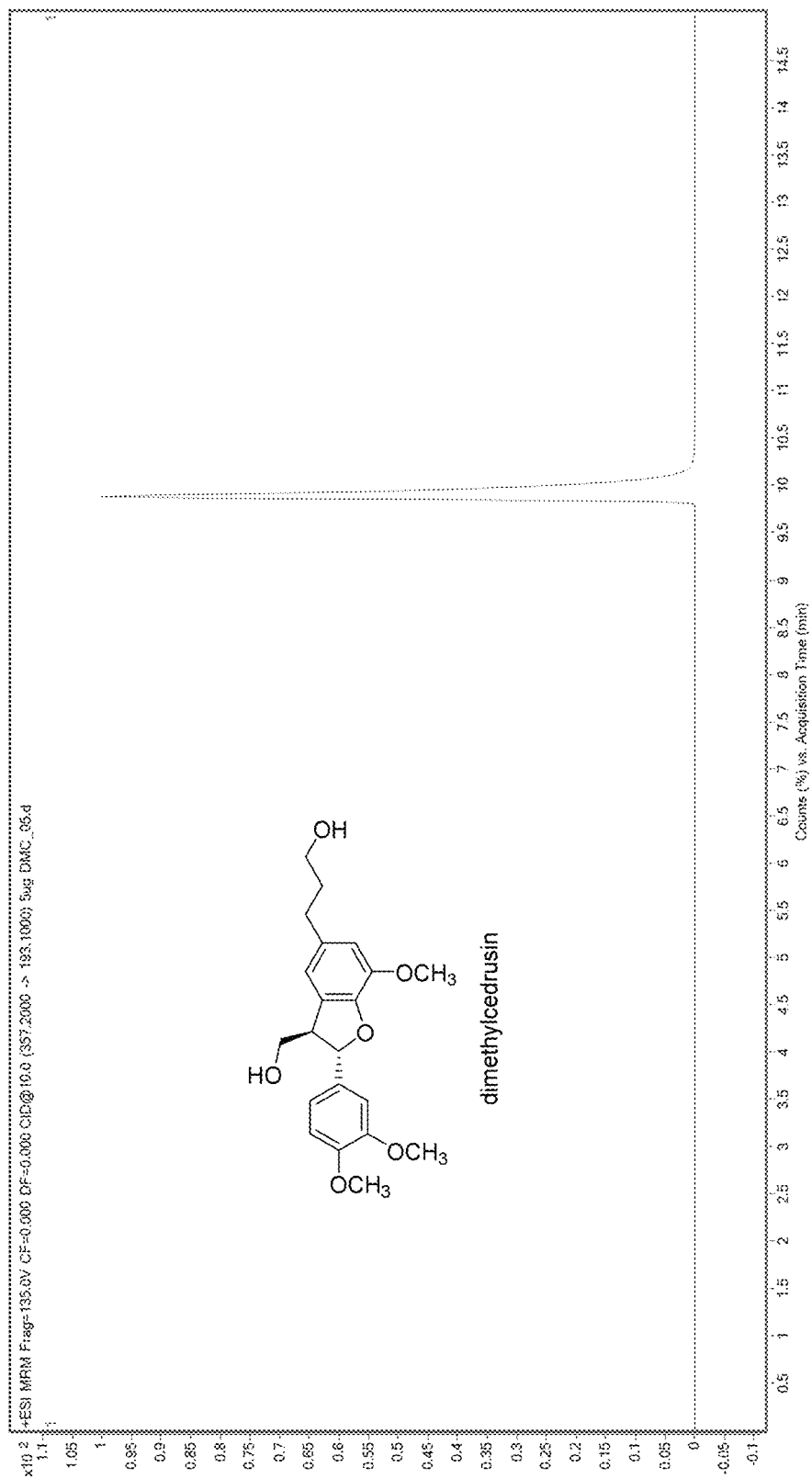
FIG. 6 depicts a representative Total Ion Chromatogram of dimethylcedrusin.

FIG. 1 depicts a representative Total Ion Chromatogram as well as additional Multiple Reaction Monitoring spectra that identify the important marker compounds in an AB-101 extract. While FIG. 6 depicts a representative Total Ion Chromatogram of dimethylcedrusin. The compounds are detectable using any of the three extraction methods.

Figure 2A:
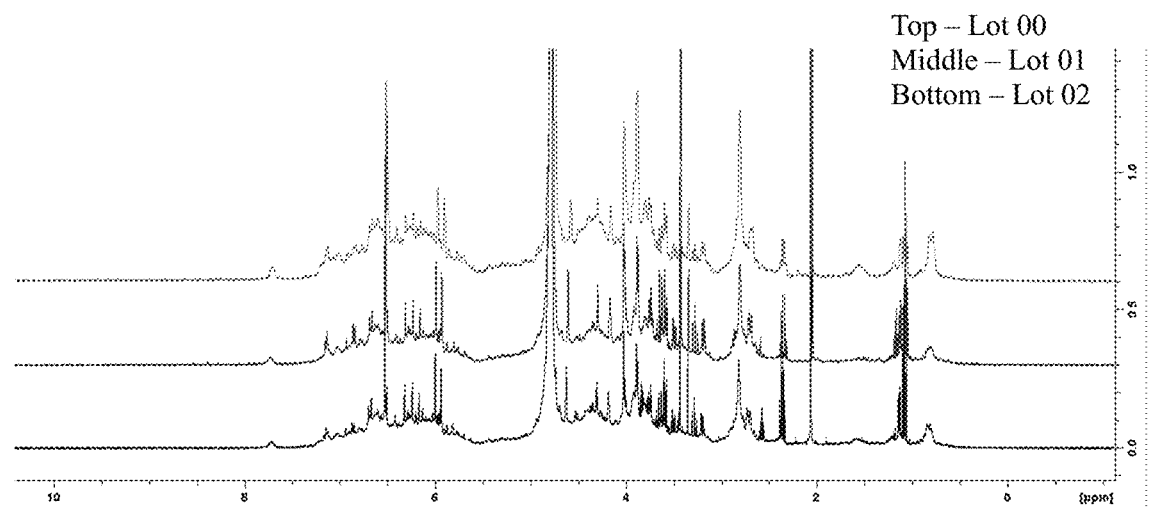
FIG. 2A depicts the NMR spectra of 3 lots of AB-101 in $D_2O$—the top spectra is for Lot 00, the middle spectra is for Lot 01, and the bottom spectra is for Lot 02.
Figure 2B:
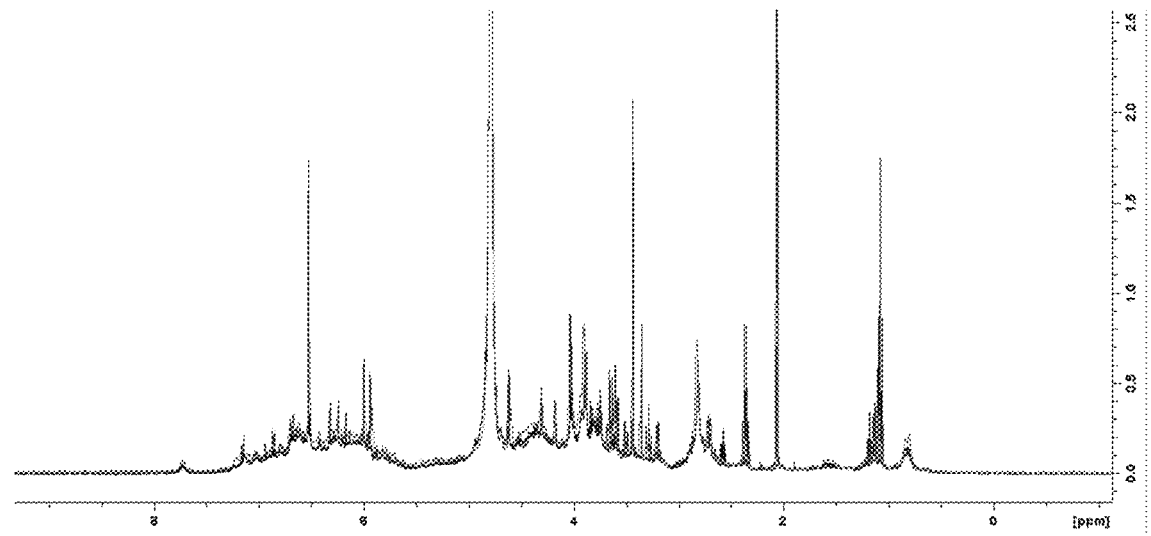
FIG. 2B depicts the overlay of the NMR spectra of Lots 00, 01, and 02 of AB-101 in $D_2O$.
Figure 3A:
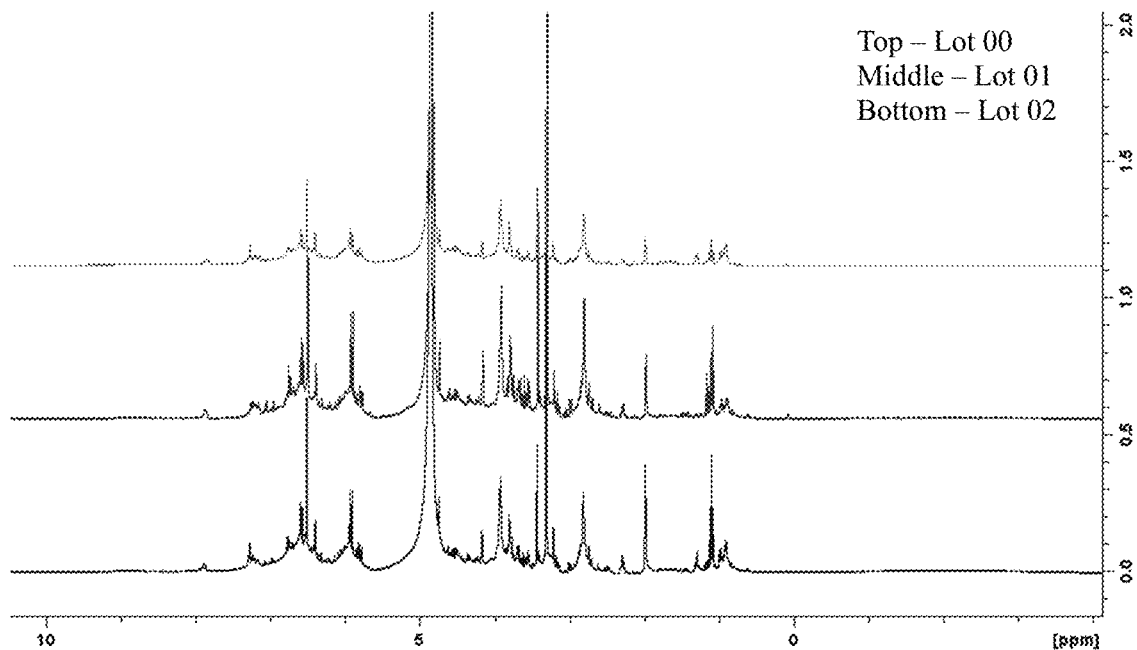
FIG. 3A depicts the Nuclear Magnetic Resonance (NMR) spectra of 3 lots of AB-101 in $d_4$-Methanol—the top spectra is for Lot 00, the middle spectra is for Lot 01, and the bottom spectra is for Lot 02.
Figure 3B:
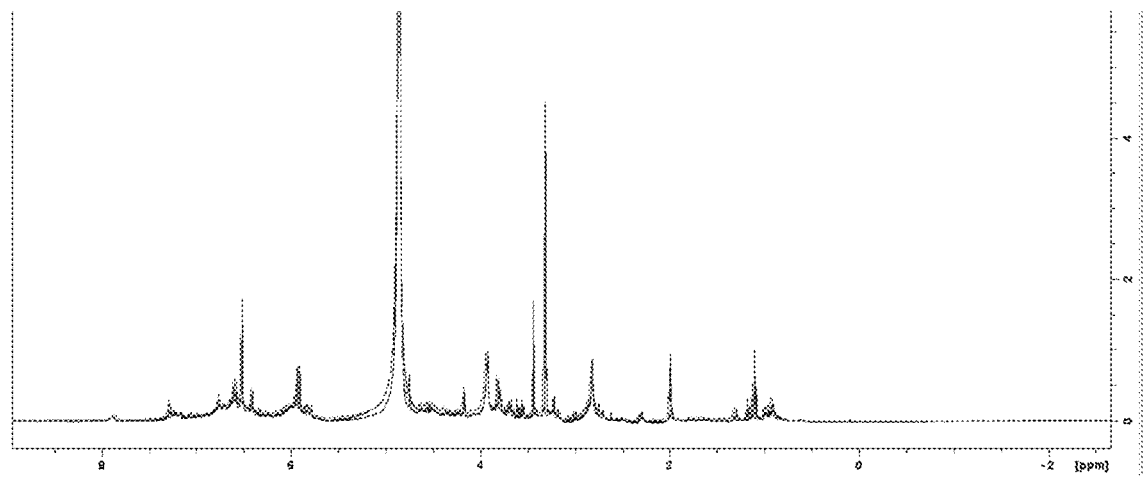
FIG. 3B depicts the overlay of the NMR spectra of Lots 00, 01, and 02 of AB-101 in $d_4$-Methanol.

Biodiversity contributes to vast amounts of variability. In order to capture this variability, an NMR method utilizing a "spectral fingerprint" was used with an overlapping a reference standard. These fingerprinting captures most components within AB-101 and would be quantifiable using Nuclear Magnetic Resonance (NMR). Examples of NMR spectra using three different AB-101 lots (Lots 00, 01, and 02 respectively) and two different deuterated solvents ($D_2O$ and $d_4$-Methanol respectively) are shown in FIGS. 2A and 3A with overlays of each solvents spectra being shown in FIGS. 2B and 3B and demonstrated no significant variability.

Figure 4A:
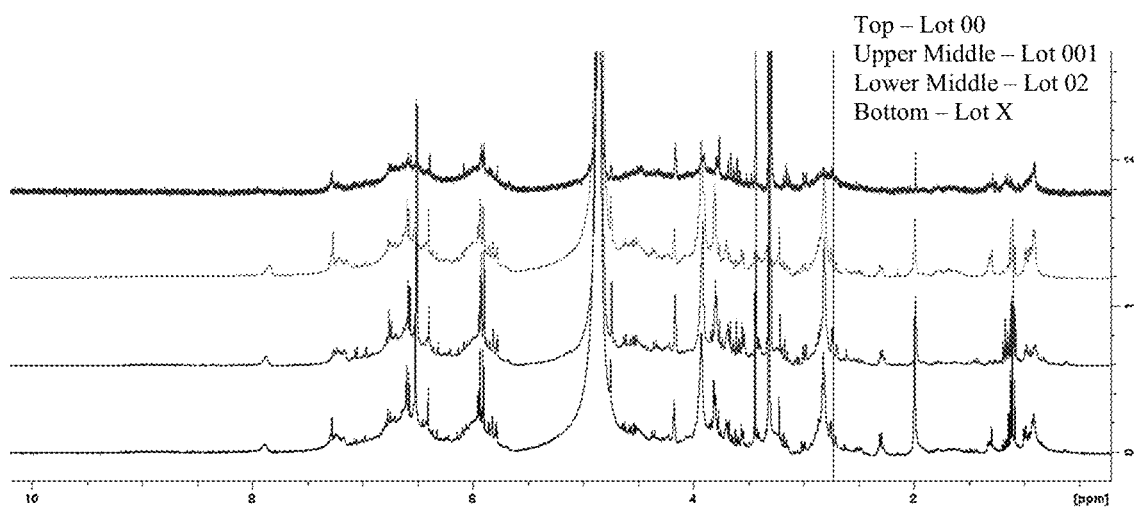
FIG. 4A depicts the NMR spectra of 4 lots of AB-101 in $d_4$-Methanol—the top spectra is for Lot 00, the upper middle spectra is for Lot 01, the lower middle is for Lot 02, and the bottom spectra is for Lot X.
Figure 4B:
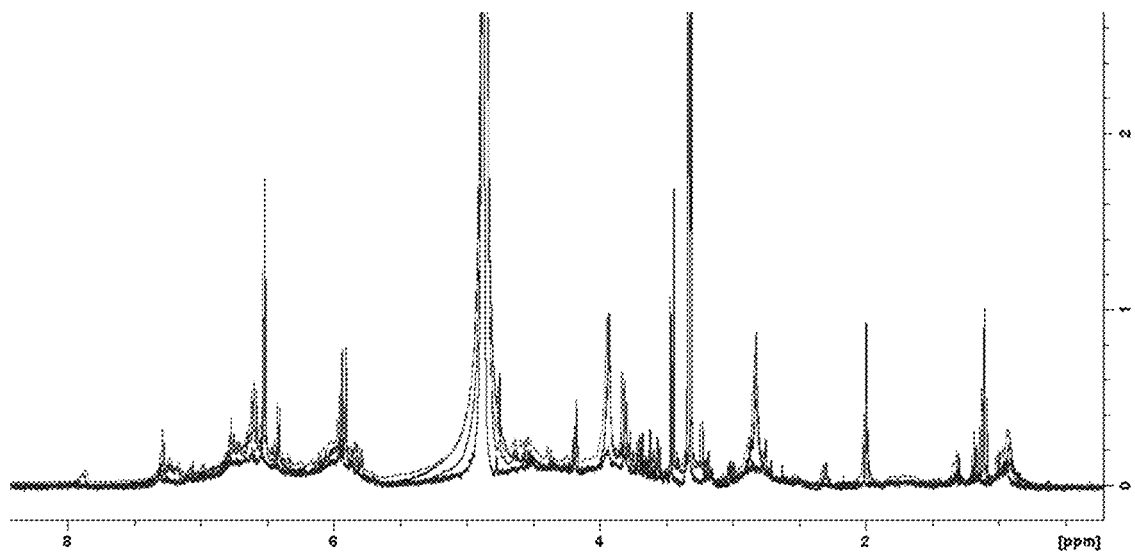
FIG. 4B depicts the overlay of the NMR spectra of Lots 00, 01, 02, and X of AB-101 in $d_4$-Methanol.
Figure 5:
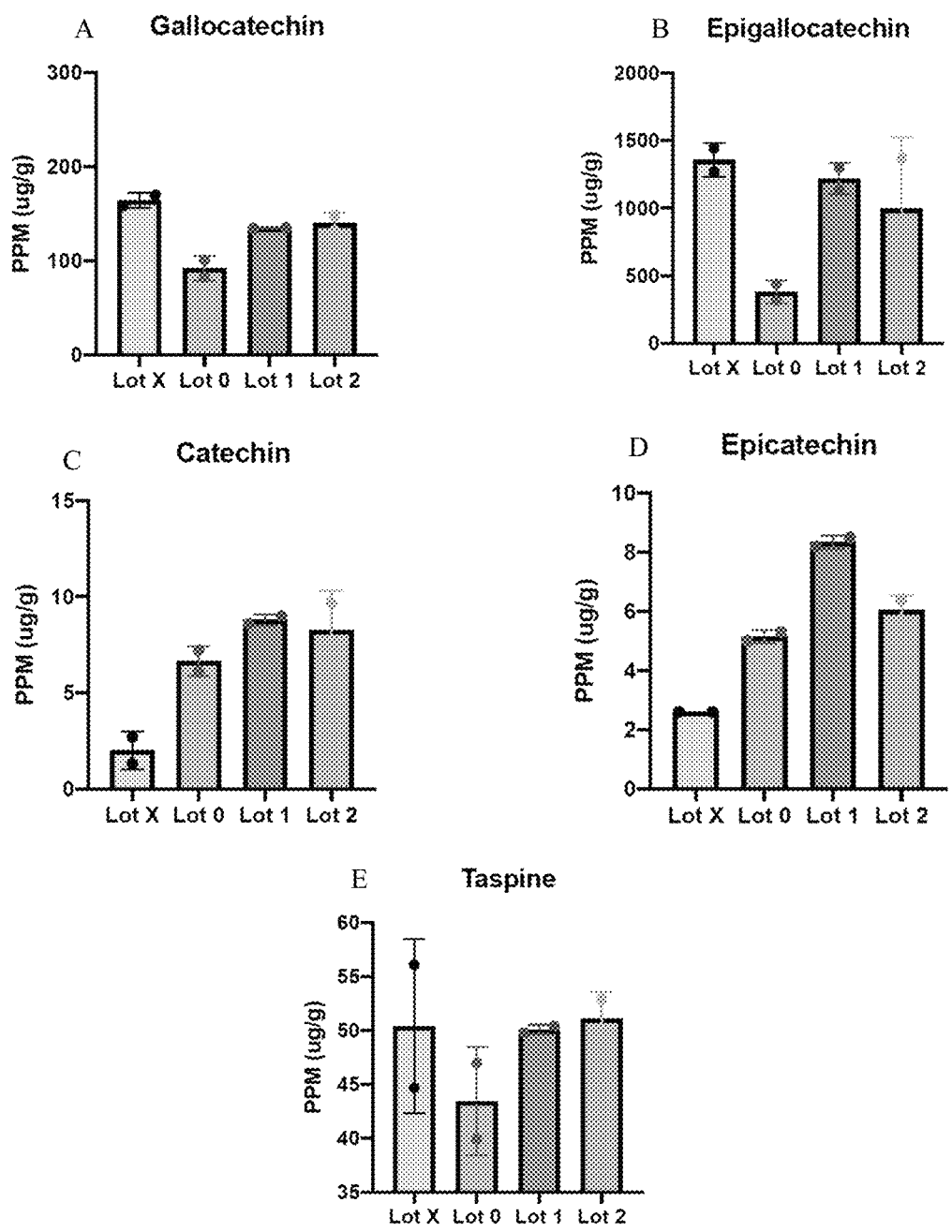
FIG. 5 depicts bar graphs comparing the AB-101 lot analysis results for A) gallocatechin B) epigallocatechin C) catechin D) epicatechin and E) taspine.

In another NMR analysis using the $d_4$-Methanol as the solvent, 4 distinct lots of AB-101 (Lots 00, 01, 02, and X respectively) are compared. NMR spectra of each lot are shown in FIG. 4A with overlays of each lots spectra being shown in FIG. 4B. While the fingerprint of the 4 lots looks similar, there are important differences. This is shown by comparing the concentration level in ppm based on LC-MS/MS Quantification and qualitative NMR "fingerprinting" on the marker compounds of catechin, epicatechin, gallocatechin, epigallocatechin, taspine, and dimethylcedrusin. The results are shown in Table 2 and indicate that lots 1 and 2 are more similar and lots X and 0 have the largest differences.

TABLE 2

| | AB-101 Lots Characterization PPM (µg/g) | | | |
|---|---|---|---|---|
| Lot | X | 00 | 01 | 02 |
| Gallocatechin (GC) | 164.2 | 91.9 | 135.0 | 139.9 |
| Epigallocatechin (EGC) | 1357.6 | 380.7 | 1219.5 | 996.3 |
| Catechin (C) | 2.0 | 6.7 | 8.8 | 8.2 |
| Epicatechin (EC) | 2.6 | 5.2 | 8.3 | 6.1 |
| Taspine (T) | 50.4 | 43.4 | 50.1 | 51.1 |
| Dimethylcedrusin | 0.1 | 0.1 | 0.1 | 0.1 |

FIG. 5A-E depicts bar graphs comparing the AB-101 lot analysis results for each of the 5 marker compounds.

Lot 00 is an example of a lot that is not suitable for use in the hydrogel formulation hydrogel formulations and the methods of use described herein. Lots X, 01 and 02 are exmaples of lots that are suitable for use in the hydrogel formulations and the methods of use described herein.

Zheng-Ping Chen publication (Studies on the Anti-Tumour, Anti-Bacterial and Wound-Healing Properties of Dragon's Blood, Planta Med. 60 (1994)) demonstrates the non-obviousness of identifying the optimum properties of pharmaceutical grade AB-101. Chen uses a bioassay used to measure the incorporation rate of H-thymidine into the DNA of the cells in the presence of the test sample. This bioassay provides a measure of the wound healing property of the "sap." Chen uses the *Croton lechleri* MÜll. Arg latex from Ecuador. This assay indicated that the dried sap and MeOH Extract would have an incorporation rate of 68+/-12 and 88+/-5. According to Chen the dried sap and MeOH was found to be very inhibitory to wound healing properties. One familiar in the art would not assume that a *Croton lechleri* MÜll. Arg latex extract as a whole would be effective in wound healing properties. Further, Chen states that the Ecuador sap contained only traces of taspine. Chen wanted to completely minimize or eliminate taspine due to the concern of being cytotoxin. Chen evaluated specific compound through extraction. Specifically, in the case of gallocatechin and epigalocatechin were rated as slightly stimulating to cell proliferation, while Catechin and Epicatechin showed little effect. Further Chen states that taspine and dimethylcedrusin showed little healing effects in the Ecuadorian sap.

The pharmaceutical grade of AB-101 identified a unique composition to maximize the healing properties while maintaining the film forming, low Log P and antibiotic activity. While Chen would not use the whole *Croton lechleri* MÜll. Arg latex containing taspine or dimethylcedrusin, AB-101 pharmaceutical grade maintained using the entire *Croton lechleri* Müll. Arg latex in the composition for medicinal benefits associated with a topical wound healing benefits. Taspine has antibiotic, antiviral and anti-inflammatory properties. Dimethylcedrusin has unique fibroblast stimulating properties to promote healing. Taspine was targeted at least about 45 PPM and dimethylcedrusin was targeted to have a detectable presence be at least about 0.1 PPM. gallocatechin and epigallocatechin were optimized to have a combined total composition of at least about 60% of the total 4 catechins where epigallocatechin was to have a composition at least about 45% of the total 4 catechins.

In some embodiments the latex of *Croton lechleri*, preferably filtered latex of *Croton lechleri*, preferably filtered latex of *Croton lechleri* Müll.Arg. has a minimum bactericidal concentration (MBC) of about 6.25 (% vol./vol.), about 12.5 (% vol./vol.), about 25 (% vol./vol.), about 50 (% vol./vol.), or a range between any two of these values. In some embodiments the latex of *Croton lechleri*, preferably filtered latex of *Croton lechleri*, preferably filtered latex of *Croton lechleri* Müll.Arg. has a MBC of about 6.25 (% vol./vol.) to about 50 (% vol./vol.).

Some embodiments herein are directed to a hydrogel formulation that further comprises one or more other therapeutic ingredients. In embodiments, the hydrogel formulation comprises a therapeutically effective amount of the latex of *Croton lechleri*, preferably filtered latex of *Croton lechleri*, preferably filtered latex of *Croton lechleri* Müll.Arg. In embodiments, the hydrogel formulation is suitable for topical administration or is a topical hydrogel formulation.

The excipient(s) must be "acceptable" in the sense of being compatible with the other ingredients of the formulation and not deleterious to the recipient thereof. The excipient(s) will utilize a low number of known, well-characterized excipient ingredients that will not impart irritation or sensitization when used topically or in wounds or reduce the efficacy of AB-101. Proper formulation of the hydrogel formulation is dependent upon the route of administration chosen. Any of the well-known techniques and excipients may be used as suitable and as understood in the art. The hydrogel formulations disclosed herein may be manufactured in any manner known in the art.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose, including eutectic solvents, eutectic-based ionic liquids, or ionic liquids. The hydrogel formulations can additionally include: lubricating agents such as talc, magnesium stearate, and mineral oil; wetting agents; emulsifying and suspending agents; preserving agents such as methyl- and propylhydroxy-benzoates.

The compositions include those suitable for topical (including, for example, dermal, oral mucosa, buccal, sublingual, intraocular, and wound cavity) administration although the most suitable route may depend upon for example the condition and disorder of the recipient. The compositions may conveniently be presented in unit dosage form and may be prepared by any of the methods well known in the art of pharmacy. Typically, these methods include the step of bringing into association latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard disclosed herein ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired composition.

The hydrogel formulations disclosed herein may be administered topically, that is by non-systemic administration. This includes the application of a compound disclosed herein externally to the surface of the skin and/or to the wound cavity and to achieve therapeutically effective amounts in the skin, such as the epidermis, dermis, and/or wound cavity. In embodiments, topical administration or a topical hydrogel formulation does not result in systemic administration or systemic exposure of the *Croton lechleri* to the patient.

Preferred unit dosage pharmaceutical compositions are those containing an effective dose, as herein below recited, or an appropriate fraction thereof, of the active ingredient.

The hydrogel formulations can be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active hydrogel formulations comprising latex of *Croton lechleri*, preferably filtered latex of *Croton lechleri*, preferably filtered latex of *Croton lechleri* Müll.Arg., wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard, can be effective over a wide dosage range and can be generally administered in a therapeutically effective amount. It will be understood, however, that the amount of the hydrogel formulations comprising latex of *Croton lechleri*, preferably filtered latex of *Croton lechleri*, preferably filtered latex of *Croton lechleri* Müll.Arg., wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard, actually administered will usually be determined by a physician, according to the relevant circumstances, including the condition to be treated, the chosen route of administration, the actual compound administered, the age, weight, and response of the individual patient, the severity of the patient's symptoms, and the like.

The pharmaceutically acceptable excipient may be selected from one or more cream bases, one or more emulsifying agents, one or more preservatives, one or more humectants, one or more diluents, and latex of *Croton lechleri*, preferably filtered latex of *Croton lechleri*, preferably filtered latex of *Croton lechleri* Müll.Arg.

In some embodiments, the therapeutically effective amount can vary according to, for example, the particular use for which the treatment is made, the manner of administration of the compound, the health and condition of the patient, and the judgment of the prescribing physician. The proportion or concentration of latex of *Croton lechleri*, preferably filtered latex of *Croton lechleri*, preferably filtered latex of *Croton lechleri* Müll.Arg., wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard, in a hydrogel formulation can vary depending upon a number of factors including dosage, chemical characteristics (e.g., hydrophobicity), and the route of administration. For example, the compounds can be provided in an aqueous physiological buffer solution containing about 0.1 to about 10% w/v of the compound for parenteral administration. Some typical dose ranges for the compounds are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, composition of the excipient, and its route of administration. Effective doses can be extrapolated from dose-response curves derived from in vitro or animal model test systems.

The amount of composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications.

Methods of Preparing a Hydrogel Formulation

The present invention relates to a method of preparing a hydrogel formulation comprising the steps of:

1) Preparing phase A by combining propanediol, methylparaben, and propylparaben to form phase A followed by mixing and heating phase A at a first temperature of about 40° C. to about 70° C. until the phase A is clear, once clear the heating is removed;
2) Preparing phase B by combining disodium edetate dihydrate, water, sodium benzoate, and potassium sorbate to form phase B followed by mixing and heating phase B at a second temperature of about 40° C. to about 70° C. until phase B is clear, once clear the heating is removed;
3) Add phase B to phase A to form phase C and stir at a first stir rate of about 500 rpm to about 1000 rpm;
4) Add PHOSAL® 50 PG (phosphatidylcholine, lysophosphatidylcholine, propylene glycol, sunflower seed oil glycerides, ethanol, soya fatty acids, ascorbyl palmitate, D,L-α-tocopherol) to stirring phase C to form phase D, stir at a second stir rate of about 500 rpm to about 1000 rpm, for example, for about 3 minutes;
5) Prepare phase E by combining caprylic/capric triglyceride and SEPINEO™ P 600 (acrylamide/sodium acryloyldimethyl taurate copolymer/isohexadecane/polysorbate 80) then mixing until homogenous;
6) Add phase E to phase D to form phase F, stir at a third stir rate of about 500 rpm to about 1000 rpm, for example, for about 3 minutes;
7) Allow phase F to cool to a third temperature of less than about 45° C.;
8) Add latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard to phase F to form phase G, stir at a fourth stir rate of about 500 rpm to about 1000 rpm, for example, for about 5 minutes;
9) Add dimethicone to phase G and stir at a fifth stir rate of about 500 rpm to about 1000 rpm for about 2 minutes to form the hydrogel formulation.

In some embodiments of the method of preparing the hydrogel formulation, the resultant hydrogel formulation comprises propanediol in an amount of about 1% to about 10%, about 2% to about 10%, about 3% to about 10%, about 4% to about 10%, about 5% to about 10%, about 6% to about 10%, about 7% to about 10%, about 8% to about 10%, about 9% to about 10%, about 1% to about 9%, about 1% to about 8%, about 1% to about 7%, about 1% to about 6%, about 1% to about 5%, about 1% to about 4%, about 1% to about 3%, about 1% to about 2%, about 2% to about 9%, about 3% to about 8%, about 4% to about 7%, about 5% to about 6%, or a value within one of these ranges. Specific examples may include about 1%, about 2%, about 3%, about 4%, about 5%, about 6%, about 7%, about 8%, about 9%, about 10%, or a range between any two of these values. In certain embodiments of the method of preparing the hydrogel formulation, the resultant hydrogel formulation comprises propanediol in an amount of about 5%. In certain embodiments of the method of preparing the hydrogel formulation, the resultant hydrogel formulation comprises propanediol in an amount of about 4%. The foregoing all represent weight percentages of embodiments of the resultant hydrogel formulation.

In some embodiments of the method of preparing the hydrogel formulation, the resultant hydrogel formulation comprises methylparaben in an amount of about 0.05% to about 0.5%, about 0.1% to about 0.5%, about 0.15% to about 0.5%, about 0.2% to about 0.5%, about 0.25% to about 0.5%, about 0.3% to about 0.5%, about 0.35% to about 0.5%, about 0.4% to about 0.5%, about 0.45% to about 0.5%, about 0.05% to about 0.45%, about 0.05% to about 0.4%, about 0.05% to about 0.35%, about 0.05% to about 0.3%, about 0.05% to about 0.25%, about 0.05% to about 0.2%, about 0.05% to about 0.15%, about 0.05% to about 0.1%, about 0.1% to about 0.45%, about 0.15% to about 0.4%, about 0.2% to about 0.35%, about 0.25% to about 0.30%, about 0.05% to about 0.25%, about 0.075% to about 0.225%, about 0.1% to about 0.2%, about 0.125% to about 0.175%, or a value within one of these ranges. Specific examples may include about 0.05%, about 0.1%, about 0.15%, about 0.2%, about 0.25%, about 0.3%, about 0.35%, about 0.4%, about 0.45%, about 0.5%, about 0.2%, about 0.225%, about 0.25%, about 0.275%, about 0.3%, or a range between any two of these values. In certain embodiments of the method of preparing the hydrogel formulation, the resultant hydrogel formulation comprises methylparaben in an amount of about 0.15%. In certain embodiments of the method of preparing the hydrogel formulation, the resultant hydrogel formulation comprises methylparaben in an amount of about 0.1%. The foregoing all represent weight percentages of embodiments of the resultant hydrogel formulation.

In some embodiments of the method of preparing the hydrogel formulation, the resultant hydrogel formulation comprises propylparaben in an amount of about 0.005% to about 0.05%, about 0.01% to about 0.05%, about 0.015% to about 0.05%, about 0.02% to about 0.05%, about 0.025% to about 0.05%, about 0.03% to about 0.05%, about 0.035% to about 0.05%, about 0.04% to about 0.05%, about 0.045% to about 0.05%, about 0.005% to about 0.045%, about 0.005% to about 0.04%, about 0.005% to about 0.035%, about 0.005% to about 0.03%, about 0.005% to about 0.025%, about 0.005% to about 0.02%, about 0.005% to about 0.015%, about 0.005% to about 0.01%, about 0.01% to about 0.045%, about 0.02% to about 0.04%, about 0.025% to about 0.035%, about 0.02% to about 0.04%, about 0.015% to about 0.045%, or a value within one of these ranges. Specific examples may include about 0.005%, about 0.01%, about 0.015%, about 0.02%, about 0.025%, about 0.03%, about 0.035%, about 0.04%, about 0.045%, about 0.05%, or a range between any two of these values. In certain embodiments of the method of preparing the hydrogel formulation, the resultant hydrogel formulation comprises propylparaben in an amount of about 0.02%. The foregoing all represent weight percentages of embodiments of the resultant hydrogel formulation.

In some embodiments of the method of preparing the hydrogel formulation, the first temperature is about 40° C. to about 70° C., about 45° C. to about 65° C., about 50° C. to about 60° C., or a value within one of these ranges. In certain embodiments of the method of preparing the hydrogel formulation, the first temperature is about 55° C.

In some embodiments of the method of preparing the hydrogel formulation, the resultant hydrogel formulation comprises disodium edetate dihydrate in an amount of about 0.05% to about 0.5%, about 0.1% to about 0.5%, about 0.15% to about 0.5%, about 0.2% to about 0.5%, about 0.25% to about 0.5%, about 0.3% to about 0.5%, about 0.35% to about 0.5%, about 0.4% to about 0.5%, about 0.45% to about 0.5%, about 0.05% to about 0.45%, about 0.05% to about 0.4%, about 0.05% to about 0.35%, about 0.05% to about 0.3%, about 0.05% to about 0.25%, about 0.05% to about 0.2%, about 0.05% to about 0.15%, about 0.05% to about 0.1%, about 0.1% to about 0.45%, about 0.15% to about 0.4%, about 0.2% to about 0.35%, about 0.25% to about 0.30%, about 0.05% to about 0.25%, about 0.075% to about 0.225%, about 0.1% to about 0.2%, about 0.125% to about 0.175%, or a value within one of these ranges. Specific examples may include about 0.05%, about 0.1%, about 0.15%, about 0.2%, about 0.25%, about 0.3%, about 0.35%, about 0.4%, about 0.45%, about 0.5%, about 0.2%, about 0.225%, about 0.25%, about 0.275%, about 0.3%, or a range between any two of these values. In certain embodiments of the method of preparing the hydrogel formulation, the resultant hydrogel formulation comprises disodium edetate dihydrate in an amount of about 0.15%. In certain embodiments of the method of preparing the hydrogel formulation, the resultant hydrogel formulation comprises disodium edetate dihydrate in an amount of about 0.10%. The foregoing all represent weight percentages of embodiments of the resultant hydrogel formulation.

In some embodiments of the method of preparing the hydrogel formulation, the resultant hydrogel formulation comprises water in an amount of about 20% to about 80%, about 25% to about 80%, about 30% to about 80%, about 35% to about 80%, about 40% to about 80%, about 45% to about 80%, about 50% to about 80%, about 55% to about 80%, about 60% to about 80%, about 65% to about 80%, about 70% to about 80%, about 75% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 25% to about 75%, about 30% to about 70%, about 35% to about 65%, about 40% to about 60%, about 45% to about 55%, or a value within one of these ranges. Specific examples may include about 20%, about 25%, about 30%, about 35%, about 40%, about 45%, about 50%, about 55%, about 60%, about 65%, about 60%, about 75%, about 80%, or a range between any two of these values. In certain embodiments of the method of preparing the hydrogel formulation, the resultant hydrogel formulation comprises water in an amount of about 43.38%. In certain embodiments of the method of preparing the hydrogel formulation, the resultant hydrogel formulation comprises water in an amount of about 33.38%. In certain embodiments of the method of preparing the hydrogel formulation, the resultant hydrogel formulation comprises water in an amount of about 40.38%. In certain embodiments of the method of preparing the hydrogel formulation, the resultant hydrogel formulation comprises water in an amount of about 38.38%. In certain embodiments of the method of preparing the hydrogel formulation, the resultant hydrogel formulation comprises water in an amount of about 40.7%. In certain embodiments of the method of preparing the hydrogel formulation, the resultant hydrogel formulation comprises water in an amount of about 39%. The foregoing all represent weight percentages of embodiments of the resultant hydrogel formulation.

In some embodiments of the method of preparing the hydrogel formulation, the resultant hydrogel formulation comprises sodium benzoate in an amount of about 0.005% to about 0.1%, about 0.1% to about 1%, about 0.05% to about 0.5%, or a value within one of these ranges. Specific examples may include about 0.005%, about 0.01%, about 0.02%, about 0.03%, about 0.04%, about 0.05%, about 0.1%, about 0.4%, about 0.45%, about 0.5%, about 0.6%, about 0.7%, about 0.8%, about 0.9%, about 1%, about 2%, about 3%, or a range between any two of these values. In certain embodiments of the method of preparing the hydrogel formulation, the resultant hydrogel formulation comprises sodium benzoate in an amount of about 0.40%. In certain embodiments of the method of preparing the hydrogel formulation, the resultant hydrogel formulation comprises sodium benzoate in an amount of about 0.45%. The foregoing all represent weight percentages of embodiments of the resultant hydrogel formulation.

In some embodiments of the method of preparing the hydrogel formulation, the resultant hydrogel formulation comprises potassium sorbate in an amount of about 0.005% to about 0.1%, about 0.1% to about 1%, about 0.05% to about 0.5%, or a value within one of these ranges. Specific examples may include about 0.005%, about 0.01%, about 0.02%, about 0.03%, about 0.04%, about 0.05%, about 0.1%, about 0.4%, about 0.45%, about 0.5%, about 0.6%, about 0.7%, about 0.8%, about 0.9%, about 1%, about 2%, about 3%, or a range between any two of these values. In certain embodiments of the method of preparing the hydrogel formulation, the resultant hydrogel formulation comprises potassium sorbate in an amount of about 0.45%. The foregoing all represent weight percentages of embodiments of the resultant hydrogel formulation.

In some embodiments of the method of preparing the hydrogel formulation, the second temperature is about 40° C. to about 70° C., about 45° C. to about 65° C., about 50° C. to about 60° C., or a value within one of these ranges. In certain embodiments of the method of preparing the hydrogel formulation, the second temperature is about 55° C.

In some embodiments of the method of preparing the hydrogel formulation, the first stir rate is about 500 rpm to about 1000 rpm, about 500 rpm to about 900 rpm, about 500 rpm to about 800 rpm, about 500 rpm to about 700 rpm, about 500 rpm to about 600 rpm, about 600 rpm to about 700 rpm, about 600 rpm to about 800 rpm, about 600 rpm to about 900 rpm, about 600 rpm to about 1000 rpm, or a value within one of these ranges. In certain embodiments of the method of preparing the hydrogel formulation, the first stir rate is about 600 rpm.

In some embodiments of the method of preparing the hydrogel formulation, the resultant hydrogel formulation comprises PHOSAL® 50 PG (phosphatidylcholine, lysophosphatidylcholine, propylene glycol, sunflower seed oil glycerides, ethanol, soya fatty acids, ascorbyl palmitate, D,L-α-tocopherol) in an amount of about 0.5% to about 5%, about 1% to about 3%, 0.5% to about 2%, about 0.05% to about 0.2%, about 0.25% to about 1.25%, about 0.01% to about 0.1%, about 0.001% to about 0.01%, about 0.005% to about 0.02%, or a value within one of these ranges. Specific examples may include about 0.001%, about 0.004%, about 0.005%, about 0.01%, about 0.02%, about 0.03%, about 0.04%, about 0.05%, about 0.1%, about 0.4%, about 0.5%, about 0.6%, about 0.7%, about 0.8%, about 0.9%, about 1%, about 2%, about 3%, or a range between any two of these values. In certain embodiments of the method of preparing the hydrogel formulation, the resultant hydrogel formulation comprises PHOSAL® 50 PG (phosphatidylcholine, lysophosphatidylcholine, propylene glycol, sunflower seed oil glycerides, ethanol, soya fatty acids, ascorbyl palmitate, D,L-α-tocopherol) in an amount of about 2%. The foregoing all represent weight percentages of embodiments of the resultant hydrogel formulation.

In some embodiments of the method of preparing the hydrogel formulation, the second stir rate is about 500 rpm to about 1000 rpm, about 500 rpm to about 900 rpm, about 500 rpm to about 800 rpm, about 500 rpm to about 700 rpm, about 500 rpm to about 600 rpm, about 600 rpm to about 700 rpm, about 600 rpm to about 800 rpm, about 600 rpm to about 900 rpm, about 600 rpm to about 1000 rpm, or a value within one of these ranges. In certain embodiments of the method of preparing the hydrogel formulation, the second stir rate is about 600 rpm.

In some embodiments of the method of preparing the hydrogel formulation, the resultant hydrogel formulation comprises caprylic/capric triglyceride in an amount of about 1% to about 10%, about 2% to about 10%, about 3% to about 10%, about 4% to about 10%, about 5% to about 10%, about 6% to about 10%, about 7% to about 10%, about 8% to about 10%, about 9% to about 10%, about 1% to about 9%, about 1% to about 8%, about 1% to about 7%, about 1% to about 6%, about 1% to about 5%, about 1% to about 4%, about 1% to about 3%, about 1% to about 2%, about 2% to about 9%, about 3% to about 8%, about 4% to about 7%, about 5% to about 6%, or a value within one of these ranges. Specific examples may include about 1%, about 2%, about 3%, about 4%, about 5%, about 6%, about 7%, about 8%, about 9%, about 10%, or a range between any two of these values. In certain embodiments of the method of preparing the hydrogel formulation, the resultant hydrogel formulation comprises caprylic/capric triglyceride in an amount of about 5%. In certain embodiments of the method of preparing the hydrogel formulation, the resultant hydrogel formulation comprises caprylic/capric triglyceride in an amount of about 7%. The foregoing all represent weight percentages of embodiments of the resultant hydrogel formulation.

In some embodiments of the method of preparing the hydrogel formulation, the resultant hydrogel formulation comprises SEPINEO™ P 600 (acrylamide/sodium acryloyldimethyl taurate copolymer/isohexadecane/polysorbate 80) in an amount of about 0.5% to about 10%, about 1% to about 10%, about 1.5% to about 10%, about 2% to about 10%, about 2.5% to about 10%, about 3% to about 10%, about 3.5% to about 10%, about 4% to about 10%, about 4.5% to about 10%, about 5% to about 10%, about 5.5% to about 10%, about 6% to about 10%, about 6.5% to about 10%, about 7% to about 10%, about 7.5% to about 10%, about 8% to about 10%, about 8.5% to about 10%, about 9% to about 10%, about 9.5% to about 10%, about 0.5% to about 9.5%, about 0.5% to about 9%, about 0.5% to about 8.5%, about 0.5% to about 8%, about 0.5% to about 7.5%, about 0.5% to about 7%, about 0.5% to about 6.5%, about 0.5% to about 6%, about 0.5% to about 5.5%, about 0.5% to about 5%, about 0.5% to about 4.5%, about 0.5% to about 4%, about 0.5% to about 3.5%, about 0.5% to about 3%, about 0.5% to about 2.5%, about 0.5% to about 2%, about 0.5% to about 1.5%, about 0.5% to about 1%, about 1% to about 9.5%, about 1.5% to about 9%, about 2% to about 8.5%, about 0.5% to about 8%, about 3% to about 7.5%, about 3.5% to about 7%, about 4% to about 6.5%, about 4.5% to about 6%, about 5% to about 5.5%, about 1% to about 5%, about 1.5% to about 4.5%, about 2% to about 4%, about 2.5% to about 3.5%, or a value within one of these ranges. Specific examples may include about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, or a range between any two of these values. In certain embodiments of the method of preparing the hydrogel formulation, the resultant hydrogel formulation comprises SEPINEO™ P 600 (acrylamide/sodium acryloyldimethyl taurate copolymer/isohexadecane/polysorbate 80) in an amount of about 3.3%. In certain embodiments of the method of preparing the hydrogel formulation, the resultant hydrogel formulation comprises SEPINEO™ P 600 (acrylamide/sodium acryloyldimethyl taurate copolymer/isohexadecane/polysorbate 80) in an amount of about 4.0%. The foregoing all represent weight percentages of embodiments of the resultant hydrogel formulation.

In some embodiments of the method of preparing the hydrogel formulation, the third stir rate is about 500 rpm to about 1000 rpm, about 500 rpm to about 900 rpm, about 500 rpm to about 800 rpm, about 500 rpm to about 700 rpm, about 600 rpm to about 700 rpm, about 600 rpm to about 800 rpm, about 600 rpm to about 900 rpm, about 600 rpm to about 1000 rpm, or a value within one of these ranges. In certain embodiments of the method of preparing the hydrogel formulation, the third stir rate is about 700 rpm to about 1000 rpm. In certain embodiments of the method of preparing the hydrogel formulation, the third stir rate is about 700 rpm.

In some embodiments of the method of preparing the hydrogel formulation, the third temperature is less than about 25° C., less than about 30° C., less than about 35° C., less than about 40° C., less than about 45° C., or a value within one of these ranges. In certain embodiments of the method of preparing the hydrogel formulation, the third temperature is less than about 25° C. In certain embodiments of the method of preparing the hydrogel formulation, the third temperature is less than about 30° C. In certain embodiments of the method of preparing the hydrogel formulation, the third temperature is less than about 35° C. In certain embodiments of the method of preparing the hydrogel formulation, the third temperature is less than about 40° C. In certain embodiments of the method of preparing the hydrogel formulation, the third temperature is less than about 45° C. In certain embodiments of the method of preparing the hydrogel formulation, the third temperature is about 20° C.

In some embodiments of the method of preparing the hydrogel formulation, the resultant hydrogel formulation comprises latex of *Croton lechleri*, preferably filtered latex of *Croton lechleri*, preferably filtered latex of *Croton*

*lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard in an amount of about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 55% to about 80%, about 60% to about 80%, about 65% to about 80%, about 70% to about 80%, about 75% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 75%, about 15% to about 70%, about 20% to about 65%, about 25% to about 60%, about 30% to about 55%, about 35% to about 55%, about 40% to about 50%, or a value within one of these ranges. Specific examples may include about 5%, about 10%, about 15%, about 20%, about 25%, about 30%, about 35%, about 36%, about 37%, about 38%, about 39%, about 40%, about 41%, about 42%, about 43%, about 44%, about 45%, about 46%, about 47%, about 48%, about 49%, about 50%, about 55%, about 60%, about 65%, about 70%, about 75%, about 80%, or a range between any two of these values. In certain embodiments of the method of preparing the hydrogel formulation, the resultant hydrogel formulation comprises latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard in an amount of about 40%. In certain embodiments of the method of preparing the hydrogel formulation, the resultant hydrogel formulation comprises latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard in an amount of about 50%. In certain embodiments of the method of preparing the hydrogel formulation, the resultant hydrogel formulation comprises latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard in an amount of about 43%. In certain embodiments of the method of preparing the hydrogel formulation, the resultant hydrogel formulation comprises latex of *Croton lechleri*, preferably filtered latex of *Croton lechleri*, preferably filtered latex of *Croton lechleri* Müll.Arg. wherein the composition contains at least the concentration of components of latex of *Croton lechleri*, preferably the concentration of components of filtered latex of *Croton lechleri*, preferably the concentration of components of filtered latex of *Croton lechleri* Müll.Arg of the reference standard in an amount of about 45%. The forgoing percentages are relative to a composition made from AB-101 with exemplary amounts of the marker compounds present in the latex as disclosed in Table 1a. To illustrate, a pharmaceutical composition comprising 100% of AB-101 will contain at least about 110 PPM of gallocatechin, while a pharmaceutical composition comprising 200% of AB-101 will contain at least about 220 PPM of gallocatechin. The foregoing all represent weight percentages of embodiments of the resultant hydrogel formulation.

In some embodiments of the method of preparing the hydrogel formulation, the fourth stir rate is about 500 rpm to about 1000 rpm, about 500 rpm to about 900 rpm, about 500 rpm to about 800 rpm, about 500 rpm to about 700 rpm, about 600 rpm to about 700 rpm, about 600 rpm to about 800 rpm, about 600 rpm to about 900 rpm, about 600 rpm to about 1000 rpm, or a value within one of these ranges. In certain embodiments of the method of preparing the hydrogel formulation, the fourth stir rate is about 700 rpm.

In some embodiments of the method of preparing the hydrogel formulation, the resultant hydrogel formulation comprises dimethicone in an amount of about 0.5% to about 10%, about 1% to about 10%, about 1.5% to about 10%, about 2% to about 10%, about 2.5% to about 10%, about 3% to about 10%, about 3.5% to about 10%, about 4% to about 10%, about 4.5% to about 10%, about 5% to about 10%, about 5.5% to about 10%, about 6% to about 10%, about 6.5% to about 10%, about 7% to about 10%, about 7.5% to about 10%, about 8% to about 10%, about 8.5% to about 10%, about 9% to about 10%, about 9.5% to about 10%, about 0.5% to about 9.5%, about 0.5% to about 9%, about 0.5% to about 8.5%, about 0.5% to about 8%, about 0.5% to about 7.5%, about 0.5% to about 7%, about 0.5% to about 6.5%, about 0.5% to about 6%, about 0.5% to about 5.5%, about 0.5% to about 5%, about 0.5% to about 4.5%, about 0.5% to about 4%, about 0.5% to about 3.5%, about 0.5% to about 3%, about 0.5% to about 2.5%, about 0.5% to about 2%, about 0.5% to about 1.5%, about 0.5% to about 1%, about 1% to about 9.5%, about 1.5% to about 9%, about 2% to about 8.5%, about 0.5% to about 8%, about 3% to about 7.5%, about 3.5% to about 7%, about 4% to about 6.5%, about 4.5% to about 6%, about 5% to about 5.5%, about 1% to about 5%, about 1.5% to about 4.5%, about 2% to about 4%, about 2.5% to about 3.5%, or a value within one of these ranges. Specific examples may include about 0.5%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, or a range between any two of these values. In certain embodiments of the method of preparing the hydrogel formulation, the resultant hydrogel formulation comprises dimethicone in an amount of about 2%. In certain embodiments of the method of preparing the hydrogel formulation, the resultant hydrogel formulation comprises dimethicone in an amount of about 2.5%. In certain embodiments of the method of preparing the hydrogel formulation, the resultant hydrogel formulation comprises dimethicone in an amount of about 3%. The foregoing all represent weight percentages of embodiments of the resultant hydrogel formulation.

In some embodiments of the method of preparing the hydrogel formulation, the dimethicone has a viscosity of about 175 cSt to about 525 cSt, about 200 cSt to about 525 cSt, about 225 cSt to about 525 cSt, about 250 cSt to about 525 cSt, about 275 cSt to about 525 cSt, about 300 cSt to about 525 cSt, about 325 cSt to about 525 cSt, about 350 cSt to about 525 cSt, about 375 cSt to about 525 cSt, about 400 cSt to about 525 cSt, about 425 cSt to about 525 cSt, about 450 cSt to about 525 cSt, about 475 cSt to about 525 cSt, about 500 cSt to about 525 cSt, about 175 cSt to about 500 cSt, about 175 cSt to about 475 cSt, about 175 cSt to about 450 cSt, about 175 cSt to about 425 cSt, about 175 cSt to about 400 cSt, about 175 cSt to about 375 cSt, about 175 cSt to about 350 cSt, about 175 cSt to about 325 cSt, about 175 cSt to about 300 cSt, about 175 cSt to about 275 cSt, about 175 cSt to about 250 cSt, about 175 cSt to about 225 cSt, about 175 cSt to about 200 cSt, about 200 cSt to about 500 cSt, about 225 cSt to about 475 cSt, about 250 cSt to about 450 cSt, about 275 cSt to about 425 cSt, about 300 cSt to about 400 cSt, about 325 cSt to about 375 cSt, or a value within one of these ranges. Specific examples may include about 175 cSt, about 200 cSt, about 225 cSt, about 250 cSt, about 275 cSt, about 300 cSt, about 325 cSt, about 350 cSt, about 375 cSt, about 400 cSt, about 425 cSt, about 450 cSt, about 475 cSt, about 500 cSt, about 525 cSt, or a range between any two of these values. In certain embodiments of the method of preparing the hydrogel formulation, the dimethicone has a viscosity of about 350 cSt.

In some embodiments of the method of preparing the hydrogel formulation, the fifth stir rate is about 500 rpm to about 1000 rpm, about 500 rpm to about 900 rpm, about 600 rpm to about 1000 rpm, about 700 rpm to about 1000 rpm, about 800 rpm to about 1000 rpm, about 900 rpm to about 1000 rpm, or a value within one of these ranges. In certain embodiments of the method of preparing the hydrogel formulation, the fifth stir rate is about 900 rpm.

In some embodiments of the method of preparing the hydrogel formulation, the resultant hydrogel formulation has a pH of about 3.0 to about 7.0, about 3.5 to about 7.0, about 4.0 to about 7.0, about 4.5 to about 7.0, about 5.0 to about 7.0, about 5.5 to about 7.0, about 6.0 to about 7.0, about 6.5 to about 7.0, about 3.0 to about 6.5, about 3.0 to about 6.0, about 3.0 to about 5.5, about 3.0 to about 5, about 3.0 to about 4.5, about 3.0 to about 4, about 3.0 to about 3.5, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, or a range between any two of these values. In certain embodiments of the method of preparing the hydrogel formulation, the resultant hydrogel formulation has a pH of about 4.0 to about 6.7. In certain embodiments of the method of preparing the hydrogel formulation, the resultant hydrogel formulation has a pH of about 3.0 to about 4.0. In certain embodiments of the method of preparing the hydrogel formulation, the resultant hydrogel formulation has a pH of about 5.5 to about 6.5.

Methods of Use

The present invention relates to a method of treatment of a dermatological condition in a subject, comprising topically administering to the subject a therapeutically effective amount of the hydrogel formulation disclosed herein.

The present invention also relates to a method of treatment of a dermatological condition in a subject, comprising topically administering to the subject a therapeutically effective amount of the hydrogel formulation disclosed herein wherein the therapeutically effective amount contains at least the concentration of components of latex of *Croton lechleri*, preferably the concentration of components of filtered latex of *Croton lechleri*, preferably the concentration of components of filtered latex of *Croton lechleri* Müll.Arg of the reference standard as disclosed herein.

The present invention also relates to methods of treatment of a dermatological condition in a subject comprising the topical administration of a therapeutically effective amount of the hydrogel formulation disclosed herein wherein the latex of *Croton lechleri*, preferably filtered latex of *Croton lechleri*, preferably filtered latex of *Croton lechleri* Müll.Arg. of the hydrogel formulation shall comprise one or more compounds selected from: gallocatechin, epigallocatechin, catechin, epicatechin, taspine, and dimethycedrusin, and combinations thereof. Each of gallocatechin, epigallocatechin, catechin, epicatechin, taspine, and dimethylcedrusin may be present in the latex of *Croton lechleri*, preferably filtered latex of *Croton lechleri*, preferably filtered latex of *Croton lechleri* Müll.Arg. in the amounts found in Table 1a or paragraphs [0134]-[0139], or any combination of such amounts. In some embodiments latex of *Croton lechleri*, preferably filtered latex of *Croton lechleri*, preferably filtered latex of *Croton lechleri* Müll.Arg. has a PDI of embodiments disclosed herein.

Also provided herein is the hydrogel formulation as disclosed herein for use as a medicament. In some embodiments latex of *Croton lechleri*, preferably filtered latex of *Croton lechleri*, preferably filtered latex of *Croton lechleri* Müll.Arg. has a PDI of embodiments disclosed herein.

Also provided herein is the hydrogel formulation as disclosed herein for use as a medicament for the treatment of a dermatological condition.

Also provided is the use of the hydrogel formulation as disclosed herein as a medicament for the treatment of a dermatological condition.

Also provided is the hydrogel formulation as disclosed herein wherein the latex of *Croton lechleri*, preferably filtered latex of *Croton lechleri*, preferably filtered latex of *Croton lechleri* Müll.Arg. of the hydrogel formulation contains the concentration of components of latex of *Croton lechleri*, preferably the concentration of components of filtered latex of *Croton lechleri*, preferably the concentration of components of filtered latex of *Croton lechleri* Müll.Arg of the reference standard, as disclosed herein for use in the manufacture of a medicament for the treatment of a dermatological condition. In some embodiments latex of *Croton lechleri*, preferably filtered latex of *Croton lechleri*, preferably filtered latex of *Croton lechleri* Müll.Arg. has a PDI of embodiments disclosed herein.

Also provided is the use of the hydrogel formulation as disclosed herein wherein the latex of *Croton lechleri*, preferably filtered latex of *Croton lechleri*, preferably filtered latex of *Croton lechleri* Müll.Arg. of the hydrogel formulation contains the concentration of components of latex of *Croton lechleri*, preferably the concentration of components of filtered latex of *Croton lechleri*, preferably the concentration of components of filtered latex of *Croton lechleri* Müll.Arg of the reference standard, as disclosed herein for the treatment of a dermatological condition. In some embodiments latex of *Croton lechleri*, preferably filtered latex of *Croton lechleri*, preferably filtered latex of *Croton lechleri* Müll.Arg. has a PDI of embodiments disclosed herein.

Also provided herein is a method of treating a dermatological condition in a subject in need thereof comprising topically administering to the subject a therapeutically effective amount of the the hydrogel formulation as disclosed herein wherein the latex of *Croton lechleri*, preferably filtered latex of *Croton lechleri*, preferably filtered latex of *Croton lechleri* Müll.Arg. of the hydrogel formulation contains the concentration of components of latex of *Croton lechleri*, preferably the concentration of components of filtered latex of *Croton lechleri*, preferably the concentration of components of filtered latex of *Croton lechleri* Müll.Arg of the reference standard, as disclosed herein. In some embodiments latex of *Croton lechleri*, preferably filtered latex of *Croton lechleri*, preferably filtered latex of *Croton lechleri* Müll.Arg. has a PDI of embodiments disclosed herein.

Also provided herein is a method for achieving a therapeutic effect in a patient comprising the administration of a therapeutically effective amount of the hydrogel formulation as disclosed herein wherein the latex of *Croton lechleri*, preferably filtered latex of *Croton lechleri*, preferably filtered latex of *Croton lechleri* Müll.Arg. of the hydrogel formulation contains the concentration of components of latex of *Croton lechleri*, preferably the concentration of components of filtered latex of *Croton lechleri*, preferably the concentration of components of filtered latex of *Croton lechleri* Müll.Arg of the reference standard. In some embodiments latex of *Croton lechleri*, preferably filtered latex of *Croton lechleri*, preferably filtered latex of *Croton lechleri* Müll.Arg. has a PDI of embodiments disclosed herein.

In some embodiments, the dermatological condition is selected from the group consisting of atopic dermatitis, epidermolysis bullosa, impetigo, psoriasis, wounds, skin colonized with a pathogen, atopic dermatitis in a patient with a *Staphylococcus aureus* infection, atopic dermatitis in a patient with a methicillin-resistant *Staphylococcus aureus* (MRSA) infection, atopic dermatitis in a patient with a mupirocin resistant MRSA infection, epidermolysis bullosa in a patient with a *Staphylococcus aureus* infection, epidermolysis bullosa in a patient with a methicillin-resistant *Staphylococcus aureus* (MRSA) infection, epidermolysis bullosa in a patient with a mupirocin resistant MRSA infection, epidermolysis bullosa is in a patient with a *Streptococcus pyogenes* infection, epidermolysis bullosa is in a patient with a *Pseudomonas aeruginosa* infection, impetigo in a patient with a *Staphylococcus aureus* infection, impetigo in a patient with a methicillin-resistant *Staphylococcus aureus* (MRSA) infection, impetigo in a patient with a mupirocin resistant MRSA infection, impetigo is in a patient with a *Streptococcus pyogenes* infection, psoriasis in a patient with a *Staphylococcus aureus* infection, psoriasis in a patient with a methicillin-resistant *Staphylococcus aureus* (MRSA) infection, psoriasis in a patient with a mupirocin resistant MRSA infection, wounds in a patient with a *Staphylococcus aureus* infection, wounds in a patient with a methicillin-resistant *Staphylococcus aureus* (MRSA) infection, wounds in a patient with a mupirocin resistant MRSA infection, wounds is in a patient with a *Streptococcus pyogenes* infection, wounds is in a patient with a *Pseudomonas aeruginosa* infection, and combinations thereof.

In some embodiments, the dermatological condition is atopic dermatitis.

In some embodiments, the dermatological condition is epidermolysis bullosa.

In some embodiments, the dermatological condition is impetigo.

In some embodiments, the dermatological condition is psoriasis.

In some embodiments, the dermatological condition is wounds.

In some embodiments, the dermatological condition is skin colonized with a pathogen.

In some embodiments, the pathogen is selected from the group consistion of *Staphylococcus aureus*, methicillin-resistant *Staphylococcus aureus* (MRSA), mupirocin-resistant MRSA, and combinations thereof.

In some embodiments, the pathogen is *Staphylococcus aureus*.

In some embodiments, the pathogen is methicillin-resistant *Staphylococcus aureus* (MRSA).

In some embodiments, the pathogen is mupirocin-resistant MRSA.

In some embodiments, the dermatological condition is atopic dermatitis in a patient with a *Staphylococcus aureus* infection.

In some embodiments, the dermatological condition is atopic dermatitis in a patient with a methicillin-resistant *Staphylococcus aureus* (MRSA) infection.

In some embodiments, the dermatological condition is atopic dermatitis in a patient with a mupirocin resistant MRSA infection.

In some embodiments, the dermatological condition is epidermolysis bullosa in a patient with a *Staphylococcus aureus* infection.

In some embodiments, the dermatological condition is epidermolysis bullosa in a patient with a methicillin-resistant *Staphylococcus aureus* (MRSA) infection.

In some embodiments, the dermatological condition is epidermolysis bullosa in a patient with a mupirocin resistant MRSA infection.

In some embodiments, the dermatological condition is epidermolysis bullosa is in a patient with a *Streptococcus pyogenes* infection.

In some embodiments, the dermatological condition is epidermolysis bullosa is in a patient with a *Pseudomonas aeruginosa* infection.

In some embodiments, the dermatological condition is impetigo in a patient with a *Staphylococcus aureus* infection.

In some embodiments, the dermatological condition is impetigo in a patient with a methicillin-resistant *Staphylococcus aureus* (MRSA) infection.

In some embodiments, the dermatological condition is impetigo in a patient with a mupirocin resistant MRSA infection.

In some embodiments, the dermatological condition is impetigo is in a patient with a *Streptococcus pyogenes* infection.

In some embodiments, the dermatological condition is psoriasis in a patient with a *Staphylococcus aureus* infection.

In some embodiments, the dermatological condition is psoriasis in a patient with a methicillin-resistant *Staphylococcus aureus* (MRSA) infection.

In some embodiments, the dermatological condition is psoriasis in a patient with a mupirocin resistant MRSA infection.

In some embodiments, the dermatological condition is wounds in a patient with a *Staphylococcus aureus* infection.

In some embodiments, the dermatological condition is wounds in a patient with a methicillin-resistant *Staphylococcus aureus* (MRSA) infection.

In some embodiments, the dermatological condition is wounds in a patient with a mupirocin resistant MRSA infection.

In some embodiments, the dermatological condition is wounds is in a patient with a *Streptococcus pyogenes* infection.

In some embodiments, the dermatological condition is wounds is in a patient with a *Pseudomonas aeruginosa* infection.

Also provided herein is a method of preventing a dermatological condition in a subject in need thereof comprising contacting the skin of the subject with the hydrogel formulation as disclosed herein wherein the latex of *Croton lechleri*, preferably filtered latex of *Croton lechleri*, preferably filtered latex of *Croton lechleri* Müll.Arg. of the hydrogel formulation contains the concentration of components of latex of *Croton lechleri*, preferably the concentration of components of filtered latex of *Croton lechleri*, preferably the concentration of components of filtered latex of *Croton lechleri* Müll.Arg of the reference standard, as disclosed herein. In some embodiments latex of *Croton lechleri*, preferably filtered latex of *Croton lechleri*, preferably filtered latex of *Croton lechleri* Müll.Arg. has a PDI of embodiments disclosed herein.

Also provided herein is a method of maintaining overall skin health in a subject in need thereof comprising contacting the skin of the subject with the hydrogel formulation as disclosed herein wherein the latex of *Croton lechleri*, preferably filtered latex of *Croton lechleri*, preferably filtered latex of *Croton lechleri* Müll.Arg. of the hydrogel formulation contains the concentration of components of latex of *Croton lechleri*, preferably the concentration of components of filtered latex of *Croton lechleri*, preferably the concentration of components of filtered latex of *Croton lechleri* Müll.Arg of the reference standard, as disclosed herein. In some embodiments latex of *Croton lechleri*, preferably filtered latex of *Croton lechleri*, preferably filtered latex of *Croton lechleri* Müll.Arg. has a PDI of embodiments disclosed herein.

The hydrogel formulations may be administered in various modes, e.g. topical (including, for example, dermal, oral mucosa, buccal, sublingual and intraocular). Also, the route of administration may vary depending on the condition and its severity.

The hydrogel formulations may be administered in various modes, e.g. topical (including, for example, dermal, oral mucosa, buccal, sublingual, intraocular, and wound cavity). The specific dose level for any particular patient will depend upon a variety of factors including the activity of the specific compound employed, the age, body weight, general health, sex, diet, time of administration, route of administration, rate of excretion, drug combination, the precise disorder being treated, and the severity of the indication or condition being treated. Also, the route of administration may vary depending on the condition and its severity.

Hydrogel formulations of the present invention may be administered once per day, twice per day, thrice per day, 4 times per day, 5 times per day, 6 times per day, 7 times per day, 8 times per day, 9 times per day, 10 times per day, or a range between of these values. In some embodiments, the hydrogel formulation is administered once per day. In some embodiments, the hydrogel formulation is administered twice per day. In some embodiments, the hydrogel formulation is administered thrice per day. In some embodiments, the hydrogel formulation is administered thrice per day. In some embodiments, the hydrogel formulation is administered one to three times per day. In some embodiments, the hydrogel formulation is administered until the dermatological condition is resolved, gone, or treated.

Hydrogel formulations of the present invention may be administered continuously, every 15 minutes 30 min., 1 hour(s) (hr.), 1½ hr., 2 hr., 2½ hr., 3 hr., 4 hr., 6 hr., 8 hr., 12 hr., 24 hr., 36 hr., 48 hr., 3 days, 4 days, 5 days, 6, days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or a range between of these values. In some embodiments, the administration lasts 24 weeks. In particular embodiments, the administration lasts 2 weeks. In particular embodiments, the administration lasts 4 weeks. In some embodiments, the administration lasts until the dermatological condition is resolved, gone, or treated.

Treatment of a dermatological condition may last 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or a range between of these values. In some embodiments, the treatment lasts 2 weeks. In some embodiments, the treatment lasts until the dermatological condition is resolved, gone, or treated.

Treatment of the dermatological condition may continue until complete resolution of the target lesion.

Treatment of the dermatological condition may continue at the discretion of the prescribing physician.

In certain embodiments, the hydrogel formulations of the present invention may be topically applied directly to the dermatological condition.

In certain embodiments, the hydrogel formulations of the present invention may be topically applied directly to the lesion that results from a dermatological condition.

In certain embodiments, dosage is the appropriate amount of the hydrogel formulation of the present invention to cover the targeted area of the dermatological condition. With the hydrogel formulation applied to each dermatological condition, once, twice, or more daily. Multiple dabs may be applied to a crop of lesions. The hydrogel formulation is gently rubbed (about 15 seconds) over the dermatological condition until the hydrogel formulation forms a thin layer.

In certain embodiments, the hydrogel formulations of the present invention is first applied to a bandage (e.g., gauze), which is then applied to the dermatological condition. The treated bandage is applied to each lesion. If the bandage is separated from the lesion or if the dressing has been worn for 24 hours, a new, treated bandage may be applied. A new dressing is generally, but not always, applied every day and may be applied up to once per week or longer period of time. In one embodiment, the composition is administered until the symptoms (e.g., skin lesions) disappear, become less pronounced, or problematic side effects occur.

In some embodiments, the hydrogel formulation has a minimum inhibitory concentration (MIC) of at least about 0.01%, at least about 0.05%, at least about 0.1%, at least about 0.25%, at least about 0.5%, at least about 0.75%, at least about 1%, at least about 3%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100%.

Example Section—Ab-101 Hydrogel Formulation and Performance

For a pharmaceutical drug to be effective, it must be readily released from the hydrogel carrier, and the hydrogel carrier should not increase the permeation or penetration of the bioactive ingredient into the skin. Minimizing skin penetration maximizes the amount of AB-101 that remains on the afflicted area of the skin to resolve the skin ailment. The AB-101 drug substance (the CPL) should have low partitioning potential to minimize systemic absorption and maximize the safety for using AB-101.

A series of hydrogel formulas containing increasing levels of pharmaceutical grade AB-101 was formulated as shown in Table 3a with the pH of each formulation shown in Table 3b. The hydrogel formulation used Dow Corning 200® fluid, 350 CST dimethicone, caprylic/capric triglycerides and SEPINEO™ P 600 copolymer to form the gel and AB-101 dosing range included 20%, 30%, 40% and 50% addition levels where purified water in the formulation was decreased as the level of AB-101 was increased. The AB-101 used in the formulation was mechanically filtered and not fractionated, maintaining the proanthocyanidins and taspine composition detailed in the AB-101 fingerprint.

TABLE 3a

Hydrogel Formulation Using Pharmaceutical Grade AB-101

| Component | AB-101 20% Hydrogel Material wt % | AB-101 30% Hydrogel Material wt % | AB-101 40% Hydrogel Material wt % | AB-101 50% Hydrogel Material wt % |
|---|---|---|---|---|
| Propanediol | 5.00% | 5.00% | 5.00% | 5.00% |
| Disodium edetate dihydrate | 0.15% | 0.15% | 0.15% | 0.15% |
| Methylparaben | 0.15% | 0.15% | 0.15% | 0.15% |
| Propylparaben | 0.02% | 0.02% | 0.02% | 0.02% |
| Filtered latex of *Croton lechleri* (AB-101 pharmaceutical grade) | 20.00% | 30.00% | 40.00% | 50.00% |
| Water | 63.38% | 53.38% | 43.38% | 33.38% |
| Dow Corning ® 200 Fluid 350 cSt (dimethicone 350 cSt) | 3.00% | 3.00% | 3.00% | 3.00% |
| caprylic/capric triglyceride | 5.00% | 5.00% | 5.00% | 5.00% |
| SEPINEO ™ P 600 (acrylamide/ sodium acryloyldimethyl taurate copolymer/ isohexadecane/ polysorbate 80) | 3.30% | 3.30% | 3.30% | 3.30% |
| Total | 100.00% | 100.00% | 100.00% | 100.00% |

TABLE 3B

| Hydrogel Formulation pH | | | | |
|---|---|---|---|---|
| AB-101 20% Hydrogel | AB-101 30% Hydrogel | AB-101 40% Hydrogel | AB-101 50% Hydrogel | AB-101 100% |
| pH 3.9 | 3.86 | 3.85 | 3.8 | 3.5 |

Example 1—AB-101 Release Studies from the Carrier: In Vitro Franz Diffusion Cell The Franz diffusion cell in vitro drug release testing (IVRT) utilized here is an accepted, industry-standard method for determining the release of a topically applied drug from its carrier (USP Chapter 1724, USP 36/NF31, 2013, Ueda et al, 2009; Li & Rahn, 1993). This testing used Versapore® membranes (Pall Corporation SKU 66394) which have been shown to be effective at demonstrating in vivo release of a drug from its carrier (Thakker K D, Chern W H. 2003. Development and validation of in vitro release tests for semisolid dosage forms-case study. Dissolution Technologies. May; 10(2):10-6). To determine the carrier release flux (the amount of permeant or test material crossing a membrane per unit of area per unit of time) of AB-101's PAC's (catechin, epicatechin, gallocatechin, epigallocatechin) and taspine, an existing analytical LC-MS/MS method was used to quantify the amount of each PAC and taspine that diffused through the membrane, ie, the flux.

TABLE 4

AB-101 Franz Diffusion Cell In vitro Drug Release Testing with LC-MS/MS Flux Calculations

| AB-101 Test Material | AB-101 Batch # | C (μg/ml) | EC (μg/ml) | GC (μg/ml) | EGC (μg/ml) | T (μg/ml) |
|---|---|---|---|---|---|---|
| AB-101, 100%, Liquid-Baseline | Avg. 0, 1, 2 | 712.5 | 509.3 | 1,382.7 | 10,579.4 | 4,399.8 |
| AB-101, 100%, Liquid | 1 | 169.2 | 143.8 | 251.1 | 2,454.3 | 723.2 |
| AB-101, 20%, Hydrogel | 1 | 31.3 | 30.0 | 46.9 | 471.0 | 136.6 |
| AB-101, 30%, Hydrogel | 1 | 40.7 | 40.2 | 78.5 | 727.5 | 211.0 |
| AB-101, 40%, Hydrogel | 1 | 68.9 | 57.0 | 114.1 | 983.1 | 273.1 |
| AB-101, 50%, Hydrogel | 1 | 88.1 | 68.7 | 130.0 | 1,430.6 | 381.0 |

Example 2—AB-101 Skin Permeation Studies: In Vitro Franz Diffusion Cell

The Franz diffusion cell in vitro drug permeation testing (IVPT) utilized here is an accepted, industry-standard method for determining the skin penetration of topically applied products (USP Chapter 1724, USP 36/NF31, 2013 and Ueda et al, 2009; Li & Rahn, 1993). Further this testing used Strat-M membranes (Millipore Sigma SKU SKBM02560) which have been shown to be predictive of in vivo skin permeation results (Flaten G E, Palac Z, Engesland A, Filipović-Grčič J, Vanić, Škalko-Basnet N. 2015. In vitro skin models as a tool in optimization of drug formulation. *Eur J Pharm Sci.* 75:10-24. To determine the transdermal flux (the amount of permeant or test material crossing a membrane per unit of area per unit of time) of AB-101's PAC's (catechin, epicatechin, gallocatechin, epigallocatechin) and taspine, an existing analytical LC-MS/MS method was used to quantify the amount of each PAC and taspine that diffused through the membrane, i.e. the flux.

The Franz diffusion cell in-vitro drug permeation test data (Table 5) demonstrated low flux or low diffusion of the AB-101 PAC's and taspine compared to the total amount of these compounds in AB-101, 100%, liquid. Low flux or low diffusion of the AB-101 PAC's and taspine was demonstrated for all AB-101 forms tested; for AB-101, 100%, liquid and each of the four AB-101 hydrogel formulations tested (AB-101 at 20%, 30%, 40% and 50% concentrations in the hydrogel delivery material). These Franz diffusion cell in-vitro drug permeation results predict low in vivo penetration of AB-101 into the skin.

TABLE 5

AB-101 Franz Diffusion Cell Skin Permeation Testing with LC-MS/MS Flux Calculations

| AB-101 Test Material | AB-101 Batch # | C (µg/ml) | EC (µg/ml) | GC (µg/ml) | EGC (µg/ml) | T (µg/ml) |
|---|---|---|---|---|---|---|
| AB-101, 100%, Liquid-Baseline | Avg. 0, 1, 2 | 712.5 | 509.3 | 1,382.7 | 10,579.4 | 4,399.8 |
| AB-101, 100%, Liquid | 1 | 8.82 | 9.11 | 18.25 | 503.51 | 10.01 |
| AB-101, 20%, Hydrogel | 1 | 0.80 | 0.78 | 0.65 | 11.46 | 2.19 |
| AB-101, 30%, Hydrogel | 1 | 0.44 | 0.48 | 0.36 | 5.82 | 1.75 |
| AB-101, 40%, Hydrogel | 1 | 0.21 | 0.27 | 0.18 | 1.86 | 1.99 |
| AB-101, 50%, Hydrogel | 1 | 0.00 | 0.00 | 0.00 | 0.00 | 1.93 |

The results indicate that the AB-101 PAC's and taspine demonstrate low flux or diffusion across intact synthetic membranes predicting low permeation in human skin and therefore low transdermal levels of AB-101.

Table 5 shows novel and unexpected results that enhances both efficacy and safety of the hydrogel containing AB-101. As the amount of AB-101 is increased, the permeation of AB-101 transdermal flux actually decreases. This is unexpected. The conventional expectation is that as the dose of AB-101 increases, the permeation would also increase. This is evidence where 100% AB-101 dose level has the highest transdermal flux or highest permeation level. In fact, at the highest dosage level, 50%, the permeation level for the PAC was at the lowest level and had negligible permeation. The inverse relationship between high dosing and lower transdermal flux for the alkaloid Taspine also holds true, where the permeation was reduced by 81% as AB-101 dosing increased to 50%.

The hydrogel completely transforms the efficacy of AB-101. This has tremendous performance advantage. Lower permeation means a significantly higher amount of AB-101 is available to treat the skin ailment enhancing efficacy while maximizes AB-101 delivery. This minimizes the potential to initiate antimicrobial resistance by maximizing the pathogen irradiation, specifically MRSA as shown in the time kill kinetic assay. The time kill kinetic assay demonstrated maximum pathogen kill was achieved at the 50% dosing level. Beyond the safety benefit associated with minimizing the potential to initiate antibacterial resistance, safety is further enhanced at higher levels of AB-101 due to the low transdermal flux indicating AB-101 will be maintained on the skin rather than absorbed systemically.

Example 3—AB-101 Partitioning Studies—In Vitro Log P

Log P is an assessment of a compound's lipophilicity, indicating how readily a mixture can partition between aqueous and organic phases. The in vitro Log P testing utilized here is an accepted, industry-standard method for evaluating the lipophilicity of compounds, and in this case of compounds topically applied to the skin (Pollastri M P. 2010. Overview on the Rule of Five. Current protocols in pharmacology. June; 49(1):9-12). When a topical drug possesses poor lipophilicity, with Log P rating of −1 to 2 (Table 6), when it is applied to the skin the topical drug will not penetrate or disperse easily into the skin (Tshepelevitsh S, Kadam S A, Darnell A, Bobacka J, Rüütel A, Haljasorg T, Leito I. 2020. Log P Determination for Highly Lipophilic Hydrogen Bonding Anion Receptor Molecules. Analytica Chimica Acta. July 30). For high systemic levels, a topical drug must be permeable enough, which is defined as lipophilic enough to partition into the lipid bilayer of the skin, but, not so lipophilic that once it is in the skin bilayer it will stay sequestered there (Weng Z, Wang K, Li H, Shi Q. 2015. A comprehensive study of the association between drug hepatotoxicity and daily dose, liver metabolism, and lipophilicity using 975 oral medications. Oncotarget. July 10; 6(19):17031). Lipophilicity plays a major role in determining where drugs are distributed within the body after absorption into tissues and, as a consequence, in how rapidly they are metabolized and excreted (Lipinski C A. 2000. Drug-like properties and the causes of poor solubility and poor permeability. Journal of pharmacological and toxicological methods. July 1; 44(1):235-49).

TABLE 6

LogP Rating Scale and Values

| LogP: | −1.0 0.0 1.0 2.0 | 3.0 4.0 | 5.0 6.0 |
|---|---|---|---|
| | Limited permeability, poor lipid solubility, poor skin absorption and distribution. | Intermediate permeability, able to cross the skin lipid bilayer but not be sequestered in the skin | Highly permeable, crosses into skin and stays sequestered in skin |

To assess the Log P partition coefficient of the entire AB-101 100% drug substance, standard Log P Partition Coefficient Test for AB-101 100% drug substance (the CPL) in its raw material liquid form were performed. Further the Log P Partition Coefficient Test for the five key components that impact antibacterial activity of the AB-101 drug substance from four different forms were performed: (1) AB-101 100% drug substance in its raw material liquid form, (2) AB-101 100% lyophilized powder resuspended in water, (3) AB-101 20% hydrogel formulation, (4) AB-101 50% hydrogel formulation.

The following Log P Partition Coefficient Test method was utilized: (a) Water and n-octanol were placed in a Glass Separatory Funnel (GSF), (b) An amount of each test form identified in the previous paragraph was measured and placed into the GSF, (c) The GSF was placed in a vortex mixer to mix and disperse the test material into the water or the n-octanol, (d) The GSF was then allowed to sit overnight to re-separate into its original two phases of water and n-octanol, (e) For AB-101 100% drug substance in its raw material liquid form, the water layer was then collected and analyzed via LCMS with this LCMS result compared to known LCMS result for each test material for the full AB-101 to determine the amount of test material in water and n-octanol, (f) all other forms the water layer was then collected and lyophilized with the remaining powder weighed and compared to the total amount of powder in AB-101 determining the amount of powder in the water layer and by subtraction the amount of powder in the n-octanol layer.

Log P for the AB-101, 100%, Drug Substance (the CPL).

The partitioning assays reported below (Table 7) determined the in vitro partitioning and release of the AB-101, 100%, drug substance (the CPL) tested in triplicate for three different quantities. These data report poor lipophilicity of AB-101, 100%, liquid form (the CPL) as defined by Log P analysis. As the skin is lipophilic, these data show that AB-101, being poorly lipophilic, will not penetrate or disperse easily into the skin when applied directly to the skin (Mtewa A G, Ngwira K, Lampiao F, Weisheit A, Tolo C U. 2018. Fundamental Methods in Drug Permeability, pKa, Log P and Log Dx Determination. J Drug Res Dev. 4(2): 2470-1009; Rolland, Y. 2011. Naturals—the return of the dragon. The Medicinal Chemist. 2015 Jul. 1; Martin, K. R. (2009). *Polyphenols as dietary supplements: A double-edged sword. Nutrition and Dietary Supplements, I.* doi: 10.2147/nds.s6422). Lack of lipophilicity further demonstrates AB-101 will not be passed through the skin into the underlying tissues or systemic circulation. AB-101 poor skin and tissue penetration demonstrates its limited ability to be absorbed into the skin resulting in even lower likelihood it will pass through the skin to reach systemic circulation or other tissues or organs. If AB-101 does reach systemic circulation, its poor tissue penetration means it will not be accumulated in tissues and will be excreted from the body.

TABLE 7

LogP Values for AB-101, 100%, Liquid Form (the CPL)

|  | AB-101, 100% 1.5 mL Sample Size | | | AB-101, 100% 5.0 mL Sample Size | | | AB-101, 100% 10.0 mL Sample Size | | |
| --- | --- | --- | --- | --- | --- | --- | --- | --- | --- |
|  | Sample 1 (0.17 mL) | Sample 2 (0.17 mL) | Sample 3 (0.17 mL) | Sample 1 (0.55 mL) | Sample 2 (0.55 mL) | Sample 3 (0.55 mL) | Sample 1 (1.10 mL) | Sample 2 (1.10 mL) | Sample 3 (1.10 mL) |
| $H_2O$ layer | 0.11 | 0.10 | 0.08 | 0.31 | 0.31 | 0.33 | 0.52 | 0.55 | 0.62 |
| Octanol layer | 0.06 | 0.07 | 0.09 | 0.24 | 0.24 | 0.22 | 0.58 | 0.55 | 0.48 |
| LogP | −0.29 | −0.15 | 0.05 | −0.11 | −0.11 | −0.18 | 0.05 | 0.00 | −0.11 |
| LogP Avg |  | −0.13 |  |  | −0.13 |  |  | −0.02 |  |

Log P for AB-101 Main Constituents and Other Compounds

Log P for the five key components that impact antibacterial activity of the AB-101 drug substance (the CPL) and AB-101's remaining unidentified compounds were tested in 4 different forms: AB-101 100% raw material liquid form (the CPL), AB-101 100% (the CPL) lyophilized and resuspended, AB-101 20% hydrogel formulation, AB-101 50% hydrogel formulation.

The partitioning assays reported here (Table 8) determined the in vitro partitioning and release of AB-101's five key components that impact antibacterial activity (the four PAC's catechin, epicatechin, epigallocatechin, gallocatechin, plus taspine) and AB-101's remaining components from four different AB-101 forms: (1) AB-101 100% liquid (the CPL) from AB-101 batches 0, 1, 2 and X, (2) AB-101 100% liquid (the CPL) from batches 0, 1, 2 and X after they were lyophilized and resuspended in water to determine the impact on partitioning of the lyophilization and resuspension processes in the event these processes are utilized in commercial production, and, (3 & 4) two AB-101 hydrogel formulations (AB-101 at 20% and AB-101 at 50%) both from AB-101 batch 1. These data report poor lipophilicity of all five key AB-101 components (the PAC's and taspine) that impact antibacterial activity and the other compounds of AB-101 as defined by Log P analysis for all four forms tested. As the skin is lipophilic, the AB-101 PAC's and taspine and the other compounds of AB-101 being poorly lipophilic will not penetrate or disperse easily into the skin when applied directly to the skin. Lack of lipophilicity further demonstrates the AB-101 PAC's and taspine and the other compounds of AB-101 will not be passed through the skin into the underlying tissues or systemic circulation. The AB-101 PAC's, taspine and the other compounds of AB-101 poor skin and tissue penetration demonstrates their limited ability to be absorbed into the skin resulting in even lower likelihood they will pass through the skin to reach systemic circulation or other tissues or organs. If any of the AB-101 PAC's, taspine or the other compounds of AB-101 do reach systemic circulation, their poor tissue penetration means they will not be accumulated in tissues and will be excreted from the body.

TABLE 8

LogP Values for the Five Key AB-101 Components that Impact Antibacterial Activity and the Remaining Compounds of AB-101 from AB-101 100% Liquid (the CPL), from AB-101 100% Liquid (the CPL) After Lyophilization and Resuspension and from Two AB-101 Hydrogel Formulations (AB-101 20% and 50%)

| AB-101 Form | AB-101 Batch # | LogP Catechin[1] $(0.51\text{-}1.8)^2$ | LogP Epicatechin[1] $(0.4\text{-}1.8)^2$ | LogP Gallocatechin[1] $(0.71\text{-}1.41)^2$ | LogP Epigallocatechin[1] $(0.00\text{-}1.49)^2$ | LogP Taspin[1] $(0.99\text{-}2.49)^2$ | LogP Remaining Compounds[3] |
|---|---|---|---|---|---|---|---|
| AB-101, 100% Liquid (the CPL) | 0 | 0.27 | −0.09 | −0.24 | −0.79 | −1.15 | 0.84 |
| Lyophilized & Resuspended | | 0.39 | 0.02 | 0.36 | 1.20 | −1.06 | 0.81 |
| AB-101, 100% Liquid (the CPL) | 1 | 0.29 | −0.02 | 0.01 | 0.27 | −1.76 | 0.63 |
| Lyophilized & Resuspended | | 0.23 | 0.02 | −0.13 | −0.11 | −0.94 | 0.01 |
| AB-101, 100% Liquid (the CPL) | 2 | 0.59 | 0.13 | 0.56 | 0.86 | −0.90 | −0.29 |
| Lyophilized & Resuspended | | 0.07 | −0.17 | −0.48 | −1.71 | −1.71 | 0.47 |
| AB-101, 100% Liquid (the CPL) | Avg. 0, 1, 2 | 0.38 | 0.01 | 0.11 | 0.11 | −1.27 | 0.39 |
| Lyophilized & Resuspended | | 0.23 | −0.04 | −0.08 | −0.21 | −1.24 | 0.43 |
| AB-101, 20% Hydrogel | 1 | −0.49 | 0.39 | 0.37 | −0.46 | −1.35 | 0.10 |
| AB-101, 50% Hydrogel | 1 | 0.62 | 0.89 | 0.93 | 0.84 | −084 | 0.09 |

[1]LogP values for reference standard PACs and Taspine do not significantly differ from PACs and Taspine from AB-101 tested in multiple forms

[2]Reference standard LogP values from ALOGPS, ChemAxon, Chemspider

[3]Other compounds present but not identified; the calculations are based on peak area of full chromatographic scan The data for AB-101, 100%, for AB-101 PAC's, for AB-101's taspine and for AB-101 hydrogel formulations support the conclusion that the chance of topical AB-101 permeating the skin layers in any appreciable amount is extremely low. The data also supports the conclusion that any AB-101 penetrating the skin will likely be metabolized/bio-transformed within the skin prior to having an opportunity for systemic absorption. Further, the likelihood of AB-101 being absorbed systemically were it to penetrate the skin is also low given the log P results, which predict little or no passage. The log P data for the hydrogel shows it provides no adverse performance factors to change the Log P partition coefficient of AB-101 within the hydrogel matrix.

Confirmation that AB-101 in the hydrogel is effective at irradicating harmful pathogens was confirmed in a well diffusion assay testing by measuring Zone of Inhibition (ZOI) and a bridging study comparing Minimum Inhibitory Concentration (MIC) to the level of AB-101 (50%) contained in the hydrogel.

The Agar diffusion assay (Remel Tryptic Soy Agar—TSA) tests were performed on the hydrogel carrier containing AB-101. The TSA plates were painted with a lawn of *S. aureus* ATCC 29213 or *P. aeruginosa* ATCC 27853. Two 4 mm holes were bored from each plate using a biopsy punch. The agar plate was then tared on an analytical balance and a small amount (around 10 mg) of hydrogel containing AB-101 was dispensed into one well. The density of AB 101 Lot 1 is 100 µL=102.4 mg, but for practical purposes 100 µL=100 mg was utilized. AB 101 Lot 1 was diluted 1:1 with sterile DI water to generate a 50% solution to match the gel's concentration of 50% AB 101. A corresponding volume of this 50% AB-101 was dispensed in the second well on the agar, TSA plates were incubated overnight, and the ZOI was measured with a ruler the next day.

TABLE 9

Well-Diffusion Zone of Inhibition for AB-101 vs. Hydrogel

| | ZOI diameter (mm) | |
|---|---|---|
| | *S. aureus* ATCC 29213 | *P. aeruginosa* ATCC 27853 |
| 50% AB-101 Lot 1 | 11 | 13 |
| 50% AB-101 hydrogel | 12 | 14 |

The results shown in Table 9 demonstrate 50% lot 1 (control) and the AB-101 hydrogel had similar ZOI, indicating equivalency of the hydrogel to AB-101 and that the hydrogel did not interfere with the effectiveness of AB-101 in inhibiting the growth of the 2 pathogens.

A bridging study was conducted to compare the relationship between the MIC of AB-101 and the hydrogel containing AB-101. The purpose of the study was to show that the hydrogel did not interfere or affect the MIC performance of AB-101 once it was released from the carrier. A 50% solution to match the gel's concentration of 50% AB 101 was used.

Using the well-diffusion method, 4 strains of *S. aureus*, 4 strains of *P. aeruginosa*, and 4 strains of *S. pyogenes* were tested against 50% AB-101 Lot 1 and against the 50% hydrogel. The strains and their AB-101 Lot 1 MIC values are listed in Table 10. For the bridging study, the weight of the hydrogel (in mg) dispensed into one well on the agar was determined on an analytical balance. The volume of 50% AB-101 Lot 1 to be added was determined by normalizing for the density of AB-101 Lot 1 (i.e., 1.02 mg/µL). For example, if 17.4 mg of hydrogel was dispensed into the first well, then 17.1 µL of 50% AB-101 Lot 1 was dispensed in the second well on the plate. The TSA plates were used for *S. aureus* and *P. aeruginosa*, while TSA+5% defibrinated sheep blood was used for *S. pyogenes*.

TABLE 10

Well-Diffusion Bridging Study Between AB-101 vs. Hydrogel

| Pathogen | Pathogen Strain | Lot 1 MIC (%) (Duplicate) | | 50% Lot 1 AB-101 ZOI Diameter (mm) | 50% hydrogel ZOI Diameter (mm) | 50% AB-101 Loaded (µl)* | 50% hydrogel loaded (mg) |
|---|---|---|---|---|---|---|---|
| *S. aureus* | CDC 228 | 3.13 | 3.13 | 13 | 15 | 12.1 | 12.39 |
| | 1674611 | 6.25 | 6.25 | 14 | 13 | 33.7 | 34.35 |
| | CDC 227 | 6.25 | 6.25 | 14 | 13 | 19.2 | 19.59 |
| | CDC 463 | 6.25 | 6.25 | 14 | 14 | 27 | 27.53 |
| *P. aeruginosa* | CDC 239 | 12.5 | 12.5 | 12 | 12 | 16.5 | 16.8 |
| | CDC 518 | 12.5 | 12.5 | 13 | 13 | 17.7 | 18.02 |
| | CDC 241 | 12.5 | 12.5 | 11 | 11 | 15 | 15.31 |
| | CDC 246 | 12.5 | 12.5 | 20 | 20 | 17.1 | 17.42 |
| *S. pyogenes* | 1744275 | 3.13 | 3.13 | 9 | 10 | 20.2 | 20.58 |
| | 20658749 | 3.13 | 3.13 | 9 | 12 | 18.7 | 19.07 |
| | 2065756 | 3.13 | 3.13 | 10 | 11 | 29.1 | 29.66 |
| | 2065762 | 3.13 | 3.13 | 9 | 10 | 16.1 | 16.43 |

*Normalized to AB-101 Lot 1 density i.e., 1.02 mg/µL

Table 10 demonstrates that the hydrogel does not interfere or alter the performance of AB-101. At the MIC levels of AB-101, the hydrogel ZOI was essential indistinguishable from the pure 50% diluted AB-101 across *S. aureus, P. aeruginosa* and *S. pyogenes*.

Example 4—Liquid Bandage and Protection

Figure 7:
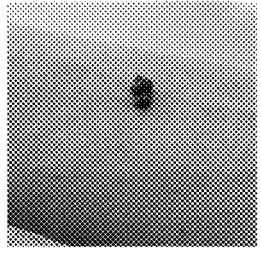
FIG. 7 depicts the liquid bandage for a film forming hydrogel containing 50% AB-101.

The hydrogel containing AB-101 at 50% has a red-brownish color prior to application. Upon application the hydrogel becomes translucent and in light color having a slight red-brownish hue. The film takes about 3 to 4 minutes to dry to touch. When the hydrogel dries, it becomes a shiny film, indicative of a liquid bandage. This liquid bandage helps to seals in the moisture from the hydrogel and provides a protective layer. Moisturization is of particular benefit to both eczema and E.B. The protective film of the liquid bandage helps to protect the skin from any impurities. FIG. 7 depicts the film forming liquid bandage properties after application to the inner forearm.

Example 5—Preparation of an AB-101 Hydrogel Formulation

The following procedures highlight the steps required to produce an AB-101 hydrogel formulation:
1) Preparing phase A by combining propanediol, methylparaben, and propylparaben to form phase A followed by mixing and heating phase A at 55° C. until the phase A is clear, once clear the heating is removed;
2) Preparing phase B by combining disodium edetate dihydrate, water, sodium benzoate, and potassium sorbate to form phase B followed by mixing and heating phase B at 55° C. until phase B is clear, once clear the heating is removed;
3) Add phase B to phase A to form phase C and stir at 600 rpm;
4) Add PHOSAL® 50 PG (phosphatidylcholine, lysophosphatidylcholine, propylene glycol, sunflower seed oil glycerides, ethanol, soya fatty acids, ascorbyl palmitate, D,L-α-tocopherol) to stirring phase C to form phase D, stir at 600 rpm for about 3 minutes;
5) Prepare phase E by combining caprylic/capric triglyceride and SEPINEO™ P 600 (acrylamide/sodium acryloyldimethyl taurate copolymer/isohexadecane/polysorbate 80) then mixing until homogenous;
6) Add phase E to phase D to form phase F, stir at 700 rpm for about 3 minutes;
7) Allow phase F to cool to 45° C. or less;
8) Add AB-101 to phase F to form phase G, stir 700 rpm for about 5 minutes.
9) Add dimethicone to phase G and stir 900 rpm for about 2 miutes to form the AB-101 hydrogel formulation.

Figure 8:
FIG. 8 depicts the hydrogel when the dimethicone is added after the hydrogel has formed.
Figure 9:
FIG. 9 depicts the hydrogel when the dimethicone is added before the hydrogel has formed.
Figure 10:
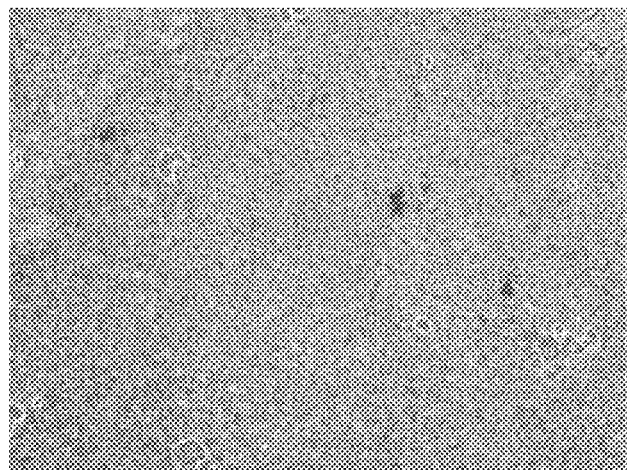
FIG. 10 depicts a microscopic picture when the dimethicone is added after the hydrogel has formed which shows a brown color demonstrating that AB-101 has been entrapped in the hydrogel matrix.
Figure 11:
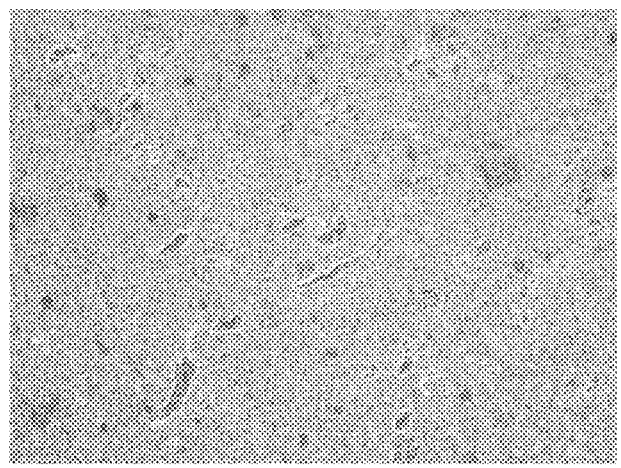
FIG. 11 depicts a microscopic picture when the dimethicone is added before the hydrogel has formed which shows a blue color demonstrating that air has been entrapped between AB-101 and the hydrogel matrix.

As shown in FIG. 8, the addition of dimethicone in the last step, after the hydrogel has formed, results in a stable and uniform product. If dimethicone is added before the hydrogel is formed the resultant product will suffer from air entrapment as shown in FIG. 9). The need to add the dimethicone after formation of the hydrogel is further demonstrated by the microscopic picture of the hydrogel formulation (FIG. 10) which shows a brown color demonstrating that AB-101 has been entrapped in the hydrogel matrix. However, when the dimethicone is added before the hydrogel is formed a microscopic picture of the hydrogel formulation (FIG. 11) shows a blue color demonstrating that air is entrapped between AB-101 and the hydrogel matrix.

Figure 12:
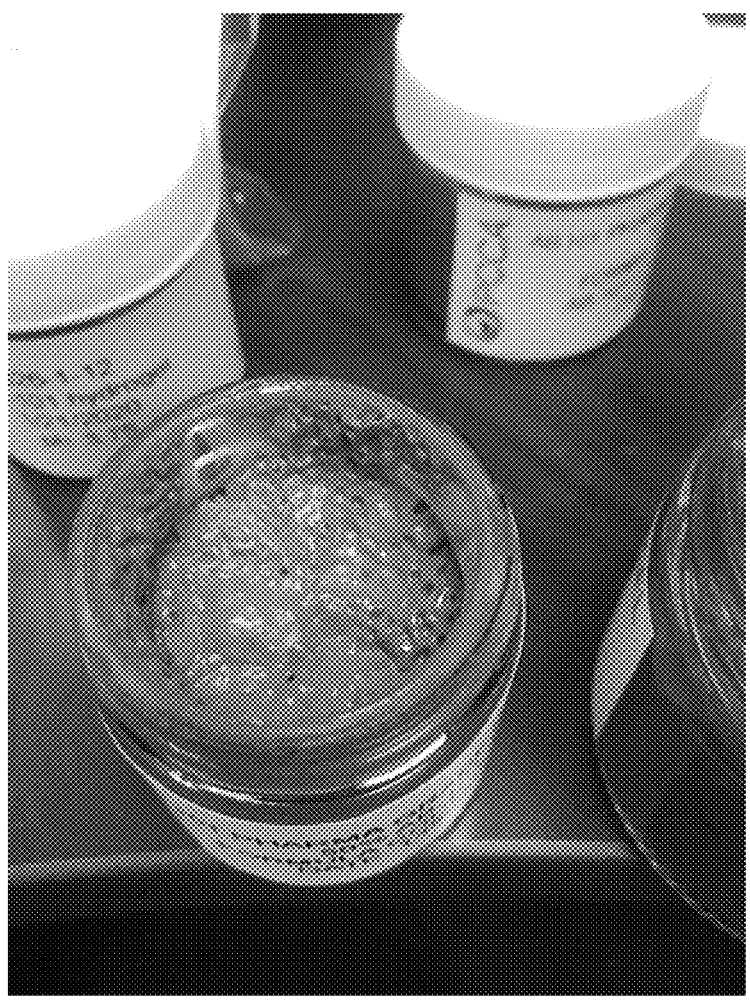
FIG. 12 depicts air entrapped in the formulation due to high shearing.
Figure 13:
FIG. 13 depicts the emulsion breaking when AB-101 is added to water before the hydrogel is created.

Stir rate during the addition of AB-101 as too much shearing with cause air to be traped in the formulation (FIG. 12) but not enough will prevent the hydrogel from forming AB-101 should be added to phase G as earlier addition (FIG. 13) of AB-101 prevents the hydrogel from forming.

To minimize the hydrogel formulations contact with air, it is best stored in an airless pump bottle.

Example 6—Study of AB-101 in the Treatment of Participants with Mild to Moderate Atopic Dermatitis with or without Secondary Infection A randomized, double-blind, multicenter study to assess the safety and efficacy of topical AB-101 versus hydrogel vehicle in the treatment of male or female participants with mild to moderate atopic dermatitis with or without secondary infection in male or female participants with mild to moderate infected or noninfected AD.

The objectives and endpoints of the study are shown in Table 11.

TABLE 11

| Objectives | Endpoints |
|---|---|
| Primary | |
| Objective: To evaluate the safety and tolerability of AB-101 hydrogel versus vehicle. | Frequency and severity of Adverse Events (AE). Study intervention discontinuation due to AEs. |
| Objective: To compare the 1-point change from baseline in IGA score between treatment arms in participants with infected (Cohort 1) and non-infected AD (Cohort 2) | Proportion of participants achieving at least a 1-point decrease in IGA score at Day 29 |
| Secondary | |
| Objective: To compare the EASI75 response between treatment arms in participants with infected (Cohort 1) and non-infected AD (Cohort 2) | EASI: Percent change from baseline in EASI total score at Day 29. |
| Objective: To compare the change in EASI score between treatment arms in participants with infected (Cohort 1) and non-infected AD (Cohort 2) | EASI: Percent change from baseline in EASI total score at Day 29. |
| Objective: To compare the 2-point change in IGA score between treatment arms in participants with infected (Cohort 1) and non-infected AD (Cohort 2) Hypothesis (H4): AB-101 is superior to vehicle alone | Proportion of participants achieving at least a 2-point decrease in IGA score at Day 29 |
| Objective: To compare the time to 1-point change in IGA score between treatment arms in participants with infected (Cohort 1) and non-infected AD (Cohort 2) | Proportion of participants achieving at least a 1-point decrease in IGA score at Day 8, 15, 22, 29 |

TABLE 11-continued

| Objectives | Endpoints |
| --- | --- |
| Objective: To compare the time to 2-point change in IGA score between treatment arms in participants with infected (Cohort 1) and non-infected AD (Cohort 2) | Proportion of participants achieving at least a 2-point decrease in IGA score at Day 8, 15, 22, 29 |
| Objective: To compare the change in SIRS between treatment arms in participants with infected (Cohort 1) and non-infected AD (Cohort 2) | SIRS calculated at Day 4, 8, 15, 22, 29 |
| Objective: To compare the change in percent BSA involvement between treatment arms in participants with infected (Cohort 1) and non-infected AD (Cohort 2) | BSA calculated using rule of nines at Day 8, 15, 22, 29 |
| Objective: To compare the change in POEM score between treatment arms in participants with infected (Cohort 1) and non-infected AD (Cohort 2) | Patient Oriented Eczema Measure reported at Day 8, 15, 22, 29 |
| Objective: To compare the change in age-specific patient-reported outcome score between treatment arms in participants with infected (Cohort 1) and non-infected AD (Cohort 2) | The Dermatology Life Quality Index (DLQI) The Children's Dermatology Life Quality Index (CDLQI) The Infants' Dermatitis Quality of Life Index (IDQOL) POEM Peak Pruritus NRS |
| Objective: To compare the bacteriology response between treatment arms in participants with infected (Cohort 1) and non-infected AD (Cohort 2) | Bacteriology response at Day 4, 8, 15, 22, 29 |

The overall study design is shown in Table 12.

TABLE 12

| | |
| --- | --- |
| Study Phase | Phase 2 |
| Primary Purpose | Treatment |
| Indication | Treatment of Mild to Moderate Atopic Dermatitis With or Without Secondary Infection |
| Population | Participants with Mild to Moderate Atopic Dermatitis |
| Study Type | Interventional |
| Intervention Model | Parallel This is a multi-site study |
| Type of Control | Vehicle |
| Study Blinding | Double-blind with in-house blinding |
| Masking | Investigator Participant Sponsor |
| Estimated Duration of Study | The Sponsor estimates that the study will require approximately 6 months from the time the first participant (or their legally accepted representative) provides documented informed consent/assent until the last participant's last study-related contact. |

Study population: Approximately 60 male/female participants aged 2 years or older with mild to moderate AD with or without secondary infection will be enrolled into this study.

Intervention groups and study duration is summarized in Table 13.

TABLE 13

| Intervention Groups | Intervention Group Name | Intervention | Drug Substance Concentration | Dose Frequency | Route of Admin. | Regimen/ Treatment Period | Use |
| --- | --- | --- | --- | --- | --- | --- | --- |
| Cohort 1—Infected AD participants | | | | | | | |
| | Arm A | AB-101 | 40% | BID | Topical | 28 days | Experimental |
| | Arm B | Vehicle | 0% | BID | Topical | 28 days | Experimental |
| Cohort 2—Non-infected AD participants | | | | | | | |
| | Arm A | AB-101 | 40% | BID | Topical | 28 days | Experimental |
| | Arm B | Vehicle | 0% | BID | Topical | 28 days | Experimental |
| Total Number | 4 intervention groups across 2 cohorts | | | | | | |
| Duration of Participation | After a Screening phase of up to 14 days, each participant will be randomized to receive intervention with AB-101 hydrogel or hydrogel vehicle in a 1:1 ratio for 28 days or until one of the conditions for discontinuation of study intervention is met. The Screening and Day 1 visits may be combined. | | | | | | |

Inclusion Criteria—Participants are eligible to be included in the study only if all the following criteria apply. Male/female participants who are ≥2 years of age on the day of providing documented informed consent/assent. Have a clinical diagnosis of AD for at least 3 months, confirmed according to the criteria of Hanifin and Rajka (1980) at the Screening visit. Mild to moderate AD indicated by IGA score of 2 (mild) or 3 (moderate) at Screening and at Day 1 prior to application of study intervention. Have AD on the head (including face, but excluding hair-bearing scalp), neck, trunk (excluding groin and genitals), or limbs, covering at least 5% of total BSA at Screening and at Day 1 (Visit 1). Have an EASI total score of ≥3 to ≤21 at Screening and at Day 1. SIRS Score of ≥8 (Cohort 1) or <8 (Cohort 2). Participant on stable regimens (consistent use 14 days before Day 1) of all allowed oral and topical medications. Willing to refrain from using any topical products and any cosmetics or skin cleansers to the Target Lesion during the study intervention application period. Willing to refrain from application of study intervention to areas of skin that are not within the Target Lesion. Participants who are willing and able to comply with all scheduled visits, treatment plan, laboratory tests, lifestyle considerations, and other study procedures. A female participant is eligible to participate if she is not pregnant, not breastfeeding, and at least one of the following conditions applies: Not a Woman of Childbearing Potential (WOCBP) or a WOCBP who agrees to follow the contraceptive guidance. The participant (or legally acceptable representative if applicable) provides documented informed consent/assent for the study.

Exclusion Criteria—Participants are excluded from the study if any of the following criteria apply. Has unstable AD or any consistent requirement for high-potency topical corticosteroids to manage AD signs and symptoms. Has an active systemic infection requiring antibiotic treatment. Has recent or anticipated concomitant use of systemic or topical therapies that might alter the course of AD. Fitzpatrick skin type score of 6. Have received prior treatment with any monoclonal antibody, TYK2 and/or JAK inhibitors within 6 months or 5 half-lives (whichever is shorter) prior to Day 1. Has undergone treatment for any type of cancer (except squamous cell carcinoma, basalcell carcinoma, or carcinoma in situ of the skin, curatively treated with cryosurgery or surgical excision only). Active or potentially recurrent dermatologic condition other than AD that may confound evaluation. Current or recent history (approximately, within 3 months) of severe, progressive, or uncontrolled renal, hepatic, hematological, gastrointestinal, metabolic, endocrine, pulmonary, cardiovascular, or neurological disease. A history of any lymphoproliferative disorder (such as Epstein Barr Virus-related lymphoproliferative disorder), history of lymphoma, leukemia, malignancies or signs and symptoms suggestive of current lymphatic disease (Note: Adults with adequately treated or excised non-metastatic basal cell or squamous cell cancer of the skin, or cervical carcinoma in situ are allowed). A history of systemic (within approximately 3 months), chronic or acute skin infection (within approximately 2 weeks) requiring hospitalization, parenteral antimicrobial, antivirals, antiparasitics, antiprotozoals, or antifungals therapy, or as otherwise judged clinically significant by the investigator. Use of systemic antibiotics or systemic corticosteroids within 28 days prior to screening. Use of topical antiviral agents, topical antibacterial agents, topical antifungal agents, or topical corticosteroid agents within 14 days prior to Day 1. A known heritable immunodeficiency disorder. Undergone significant trauma or major surgery within 1 month prior to screening at the discretion of the investigator. Known hypersensitivity to AB-101 or any component of the vehicle. Other acute or chronic medical or psychiatric condition including recent (within the past year) or active suicidal ideation or behavior or laboratory abnormality that may increase the risk associated with study participation or investigational product administration or may interfere with the interpretation of study results and, in the judgment of the investigator, would make the participant inappropriate for entry into this study. A WOCBP who has a positive urine pregnancy test within 24 hours prior to randomization or treatment allocation. If the urine test is positive or cannot be confirmed as negative, a serum pregnancy test is required (Note: If 24 hours have elapsed between the screening pregnancy test and the first dose of study intervention, another pregnancy test (urine or serum) must be performed and must be negative for participant to start receiving study intervention). Has received a live or live-attenuated vaccine within 30 days prior to the first dose of study intervention. Administration of killed vaccine and mRNA vaccines is allowed. Is currently participating in or has participated in a study of an investigational agent or used an investigational device within 28 days prior to the first dose of study intervention. Has a known history of HIV, Hepatitis B or Hepatitis C infection (Note: No testing for HIV, Hepatitis C or Hepatitis C is required unless mandated by local health authority). Investigator site staff members directly involved in the conduct of the study and their family members; site staff members otherwise supervised by the investigator, are not eligible. Has a history of alcohol or substance abuse within 6 months prior to Screening that in the opinion of the investigator will preclude participation in the study. Has a history or current evidence of any condition, therapy, or laboratory abnormality that might confound the results of this study, interfere with the participant's participation for the full duration of the study, or is not in the best interest of the participant to participate, in the opinion of the treating investigator.

Discussion of Study Design

The Phase 2a, multicenter, randomized, double-blind, vehicle-controlled, parallel group study will assess the safety and efficacy of AB-101 topical hydrogel formulation when applied twice daily in participants with mild or moderate AD with or without secondary infection.

Participants will be screened within 14 days prior to the Day 1 dose of study intervention to confirm they meet the selection criteria for the study. The Screening visit and Day 1 visit may be combined. The treatment with study intervention will be BID for up to 4 weeks (28 days), followed by a follow-up visit 1 week (7 days) later as outlined in the SoA. The total study duration for a participant is approximately 5 weeks.

Pediatric and adult participants aged 2 years of age or older with mild or moderate AD dermatitis as determined by the IGA scale with or without secondary infection as determined by the investigator and confirmed with the SIRS scale will be enrolled. The study consists of 2 cohorts with 2 arms each. Cohort 1 will enroll 20 evaluable and Cohort 2 will enroll 40 evaluable participants randomized in a 1:1 ratio to receive active or vehicle control study intervention:

Cohort 1: Mild or moderate AD with secondary infection
Cohort 2: Mild or moderate AD without secondary infection A participant will enter the screening period once he/she has agreed to participate and has signed informed consent/assent. Participants with mild to moderate AD per the IGA scale and a total body surface area (BSA) involvement of ≥5% that includes involvement in targetable areas of skin and who meet all the inclusion criteria and none of the exclusion criteria, and who successfully complete the screening process, will be eligible to be enrolled.

Once enrolled, the participant will be randomized to receive either AB-101 or hydrogel vehicle (2:1 ratio) for topical application to targeted involved AD. The first dose will be applied at the clinic. The participant will be given a diary and printed instructions on how to apply the study intervention BID, ≥8 hours between applications, for up to 28 days. Participants will return to the study clinic on Days 4, 8, 15, 22, and 29, for a total of 5 study efficacy evaluation visits after screening. All participants will also return for a follow-up study visit on Day 36 or 7 days after the last dose.

Assessments of microbiology, IGA, EASI, SIRS, and BSA involvement will occur at Day 1 and every efficacy study visit (Days 4, 8, 15, 22, 29). Photography of lesions will be performed at these visits at selected sites.

A participant in Cohort 1 whose AD is judged by the investigator to demonstrate clinical progression of existing infection in AD-involved skin in the targeted area for study will be discontinued from study intervention and End of Treatment procedures are performed.

A participant in Cohort 2 whose AD is judged by the investigator to demonstrate clinical progression to clinically overt infected AD-involved skin in the targeted area for study will be discontinued from study intervention and End of Treatment procedures are performed.

Prematurely discontinued participants in Cohort 1 and Cohort 2 will continue study participation for 7 days to obtain follow-up outcome data.

Assuming 20% dropout rate, a total of approximately 72 participants (24 per Cohort 1 and 48 per Cohort 2) will be randomized to ensure completion of approximately 60 participants (20 per Cohort 1 and 40 per Cohort 2).

Investigators, participants, and the Sponsor study team will be blinded regarding study intervention.

All primary and secondary endpoints will be achieved.

Example 7—Polydispersity Index Analysis of AB-101

To determine the PDI, an HPLC-UV method using gel permeation chromatography (GPC) and/or size exclusion (SEC) chromatography for this polymer analysis was developed. The polymer size distribution is calculated using the following equation: $PDI=M_w/M_n$, where $M_w$ is weight average molecular weight and $M_n$ is the number of the average molecular weight.

Sample Preparation: AB-101 was prepared by aliquoting 5 mL of material and lyophilizing the samples overnight. Samples were then weighed out and re-suspended in water at a concentration of 5 mg/mL. Samples were then diluted in water prior to GPC-UV/CAD analysis for PDI determination. Details of the HPLC method are below:

Column: Jordi Resolve columns 5 µm (7.8 mm ID×300 mm L), Porosity: 500 Å
HPLC Conditions: Isocratic: Dimethylformamide (DMF)
Flow rate: 0.7 mL/min
Injection volume: 20 µL
Column temperature: 40° C.
Detection: CAD
Standards: Polymethyl methacrylate (PMMA) EasiVials (Agilent)

Figure 14:
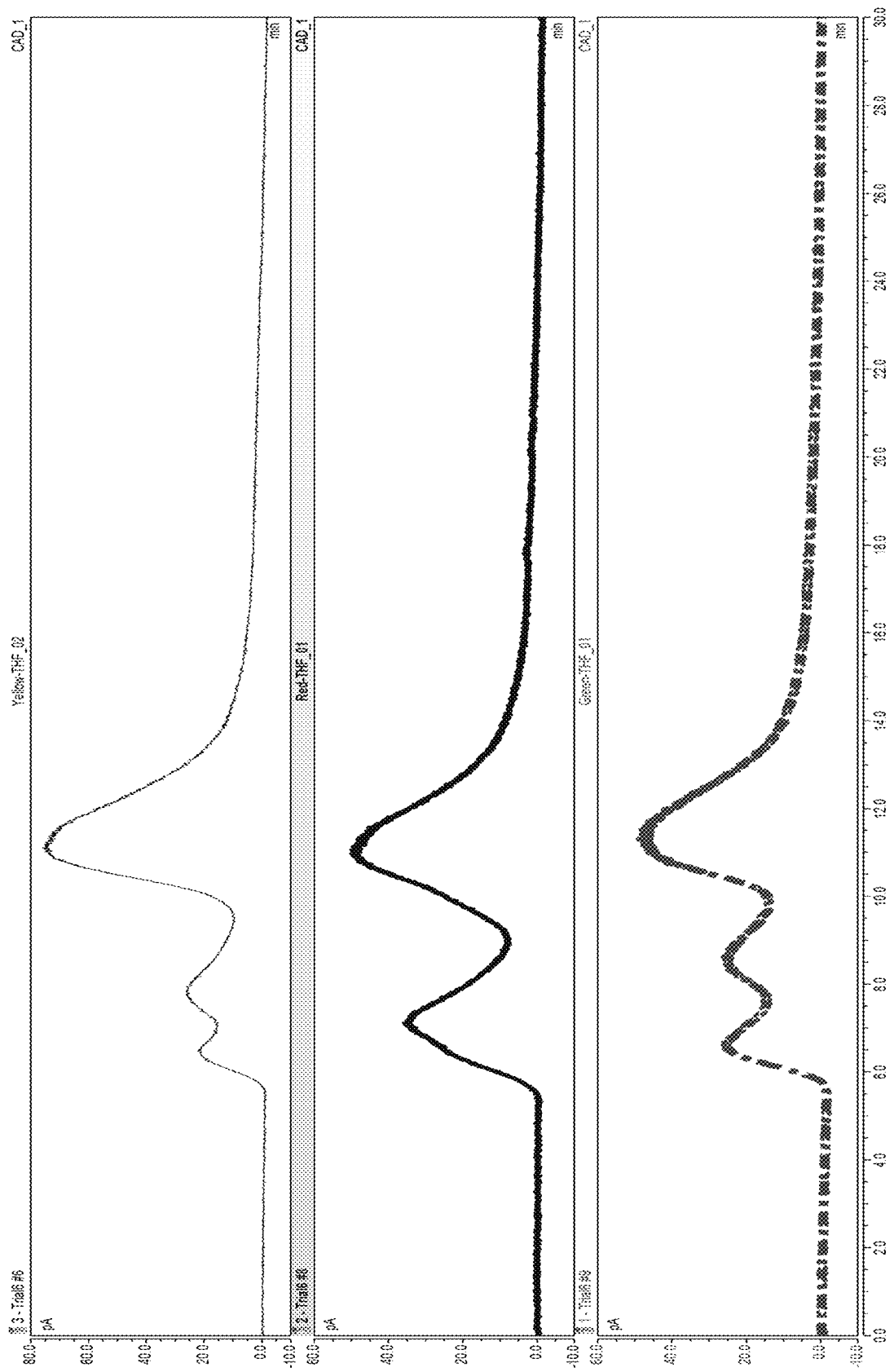
FIG. 14 depicts the gel permeation chromatogram of each of the 3 PMMA standards.
Figure 15:
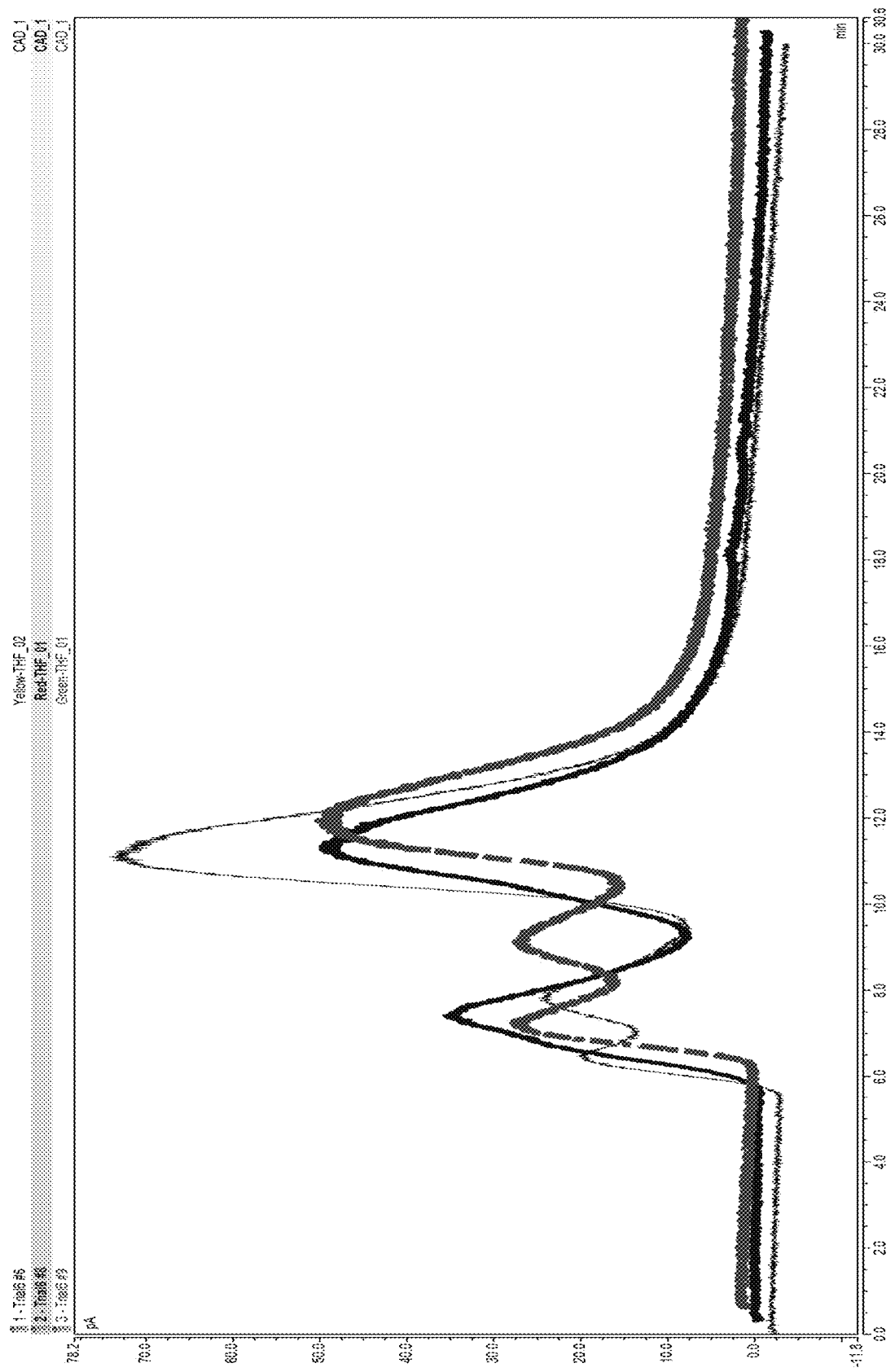
FIG. 15 depicts the overlay of the gel permeation chromatogram of the 3 PMMA standards.
Figure 16:
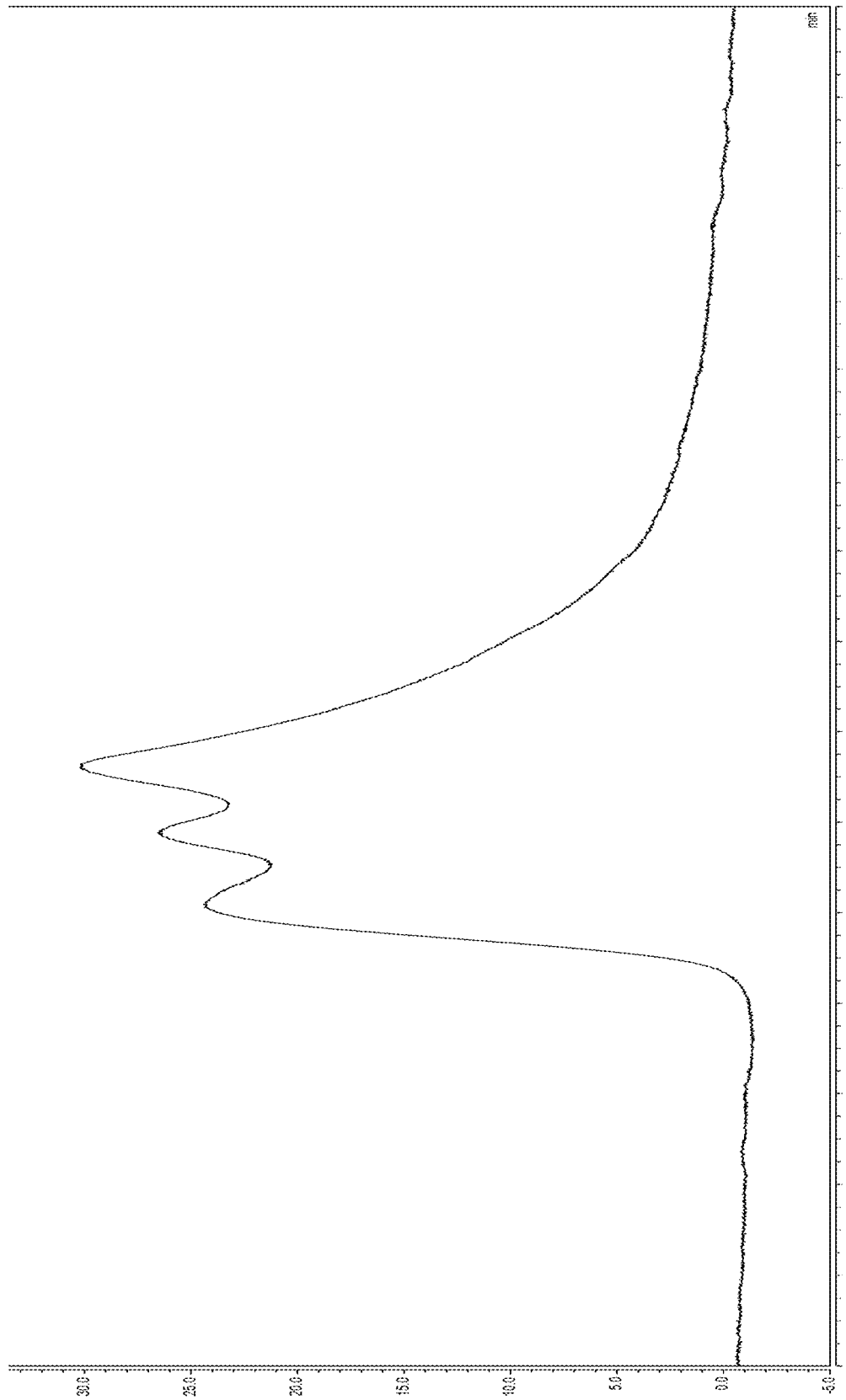
FIG. 16 depicts the AB-101 Lot 01 chromatograms at a 1.25 mg/mL concentration.

FIGS. 14 and 15 show the gel permeation chromatogram of 3 PMMA standards analyzed and now being detected. Top line is standard Yellow. Thicker line in the middle is standard Red. Dashed line on the bottom is standard Green. These standards were run at 2 mg/mL. The chromatograph demonstrated discerning peaks that enables calculation of PDI. FIG. 16 depicts the AB-101 Lot 01 chromatograms at a 1.25 mg/mL concentration.

Figure 17A:
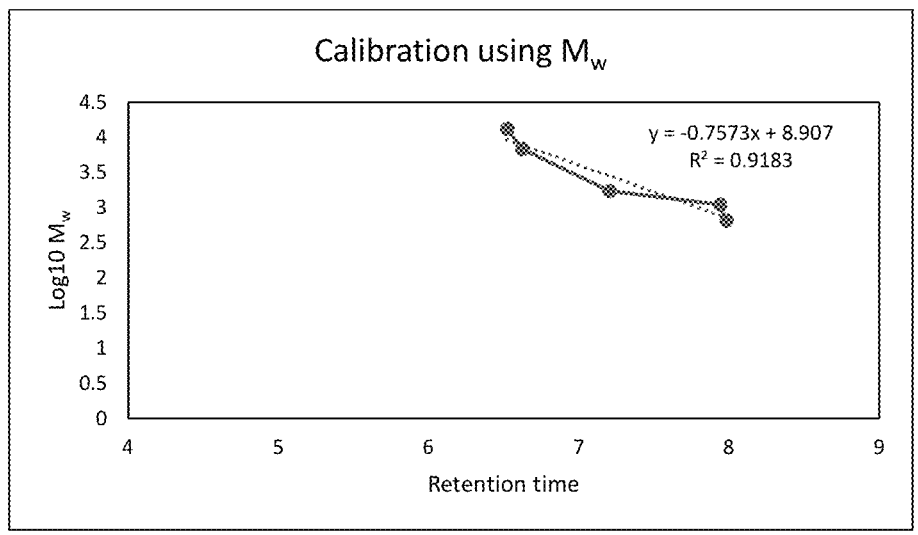
FIG. 17A depicts the calibration curve for $M_w$.
Figure 17B:
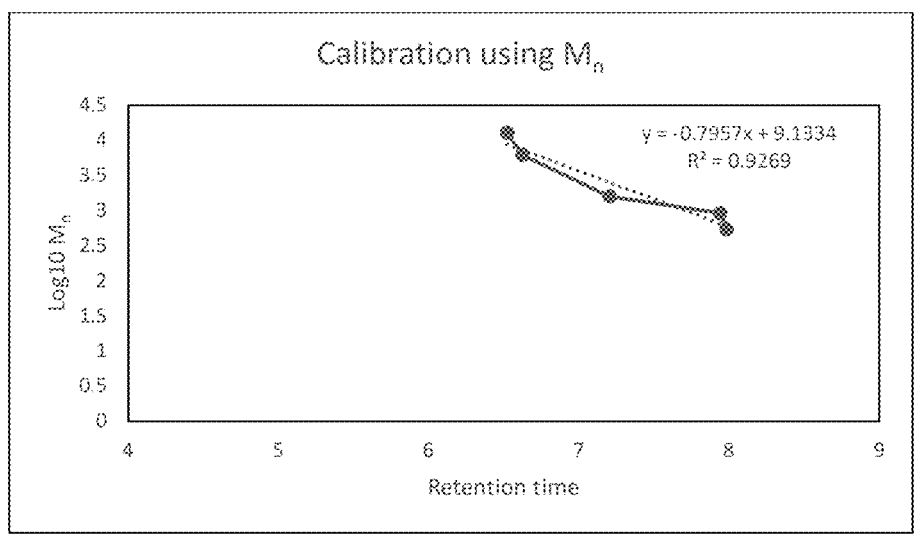
FIG. 17B depicts the calibration curve for $M_n$.

Polydispersity Index Calculations: Sample analysis for AB-101 Lot 01 using the developed method was performed. Calibration curves were generated based on Log $M_w$ vs. retention time and Log $M_n$ vs. retention time. The calibration curves are shown in FIGS. 17A and 17B. Using the calibration curves, the PDI was able to calculate the $M_w$ and $M_n$ values from AB-101 Lot 01 based on the peak retention times. Results are shown in Table 14.

TABLE 14

| RT (min) | Log $M_w$ | $M_w$ | Log $M_n$ | $M_n$ |
| --- | --- | --- | --- | --- |
| 6.8 | 2.78 | 1.02 | 2.93 | 1.08 |
| 7.8 | 1.46 | 0.33 | 1.68 | 0.52 |
| 8.0 | 1.20 | 0.18 | 1.42 | 0.35 |
|  | Average | 0.53 | Average | 0.65 |
|  |  |  | PDI | 0.81 |

Lot 01 of AB-101 has a PDI of 0.81. This is in contrast to the PDI range of 0.9-1.2 for crofelemer as disclosed in WO 2012/101008. The larger PDI for crofelemer indicates that through the refining and fractionation process, crofelemer has greater heterogeneity in cross linking, network formation, chain length and branching than AB-101.

Example 8—Particle Size Analysis of AB-101

AB-101 is a colloidal suspension based on the particle size analysis. This inherently makes formulation challenging since colloidal suspensions are inherently unstable. Shown for the first time in a hydrogel is a method to significantly improve the stability of the hydrogel containing the pharmaceutical grade of AB-101.

Figure 18:
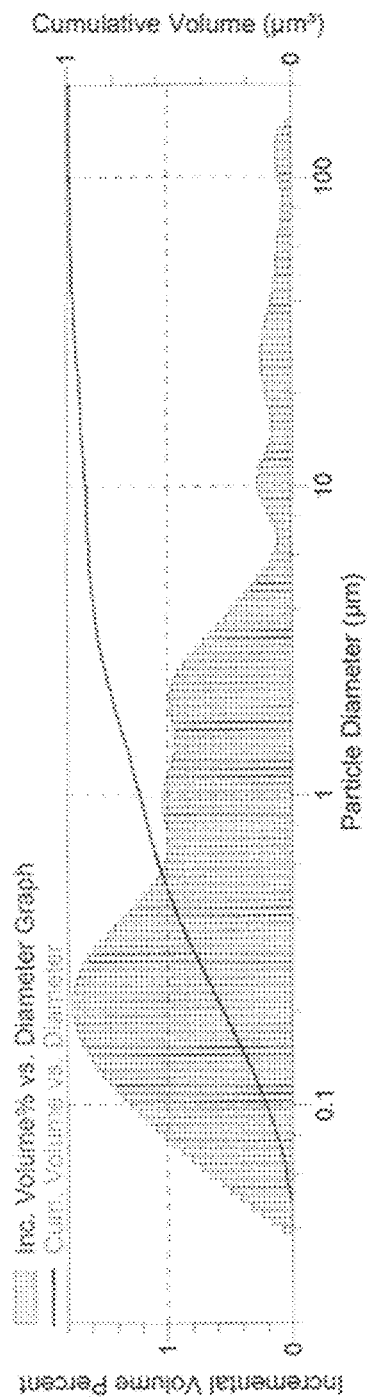
FIG. 18 depicts the result of the particle size distribution analysis of a lot of AB-101.

One of the main contributors to colloidal suspension stability is the particle size distribution. As a natural plant extract, AB-101 has a large particle size distribution. The particle size distribution for AB-101 was measured by Particle Testing Authority, a division of Micromeritics Instrument Corporation using a Saturn DigiSizer Model 5205 Laser Particle Size Analyzer. The result of the particle size distribution analysis is shown in FIG. 18.

The particle size distribution of pharmaceutical grade of AB-101 is very broad. The Average Particle Diameter (µm) range is between 0.040 µm to 150.335 µm. At the low end of the range, comprising 19.6% of the particles, the particle distribution spread was 0.040 µm to 0.142 µm. The top end of the range comprising 19.5% of the particles, the particle distribution spread was from 2.249 µm to 150.335 µm. This is a very large particle distribution. A product with a smaller, more uniform particle size is more stable and less likely to separate out. This broad colloidal particle distribution presents inherent challenges to maintain stability in a hydrogel containing AB-101.

Example 9—Zeta Potential of AB-101

The zeta potential is an important and readily measurable indicator of the stability of colloidal dispersions. The magnitude of the zeta potential indicates the degree of electrostatic repulsion between adjacent, similarly charged particles in a dispersion. For molecules and particles that are small enough, a high zeta potential will confer stability, i.e., the solution or suspension will resist aggregation. When the potential is small, attractive forces may exceed this repulsion and the dispersion may coagulate, flocculate, and eventually solidify. So, colloids with high zeta potential (negative or positive) are electrically stabilized while colloids with low zeta potentials tend to coagulate or flocculate as outlined in the Table 15.

TABLE 15

Zeta Potential and Stability Behavior

| Zeta potential (mV) | Stability behavior |
| --- | --- |
| 0 to ±5 | Rapid coagulation or flocculation |
| 10 to ±30 | Incipient instability |
| ±30 to ±40 | Moderate stability |
| ±40 to ±60 | Good stability |
| >61 | Excellent stability |

Figure 19:
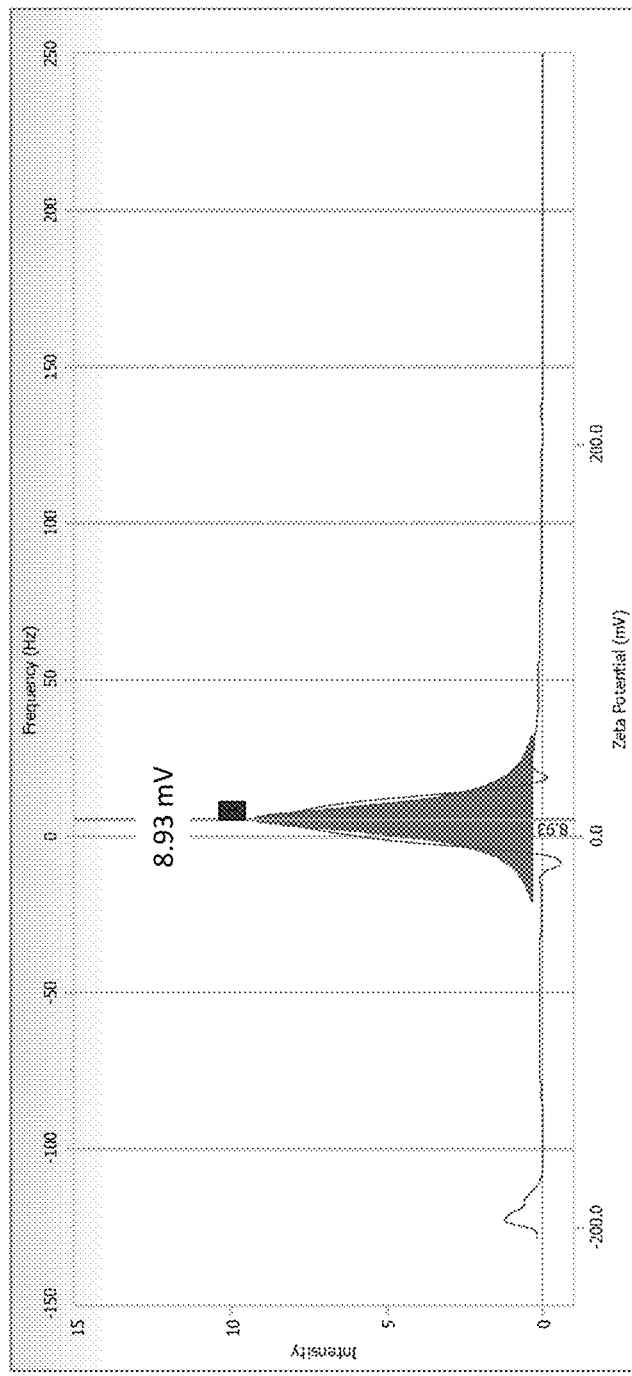
FIG. 19 depicts the mobility distribution for zeta potential for a lot of pharmaceutical AB-101 extract.

The zeta potential for the pharmaceutical grade of the whole AB-101 extract was conducted by Particle Testing Authority using NanoPlus HD Zeta Potential and Nano Particle Analyzer. The AB-101 result for the zeta potential is 8.93 mV as shown in FIG. 19. Table 15 characterizes the properties of AB-101 as exhibiting "rapid flocculation to incipient instability" behavior. Hydrogels formulated with pharmaceutical grade AB-101 would form hydrogels that would lack stability. This would result in a formula that would not meet FDA requirements to provide a reliable drug delivery system.

Formulating a physically stable hydrogel containing high concentration of AB-101 is a significant accomplishment. The challenge is to maintain the pharmaceutical bioactivity of the API, the sufficient release of AB-101 from the hydrogel, the hydrogel spread ability, while maintaining the pH targets. Physical stability of the formulated hydrogel necessitates preventing coagulation, flocculation, and solidification of the hydrogel overtime and at higher temperatures.

For the first time, pharmaceutical grade AB-101 was formulated into a novel long-term physically stable hydrogel using deflocculants. The hydrogel formula containing AB-101 using deflocculant stabilization is shown in Table F. This formula demonstrated for the first time a significant advancement in improving formulation stability via increasing the zeta potential while maintaining both the pharmaceutical and aesthetic properties of AB-101 hydrogel.

Figure 20:
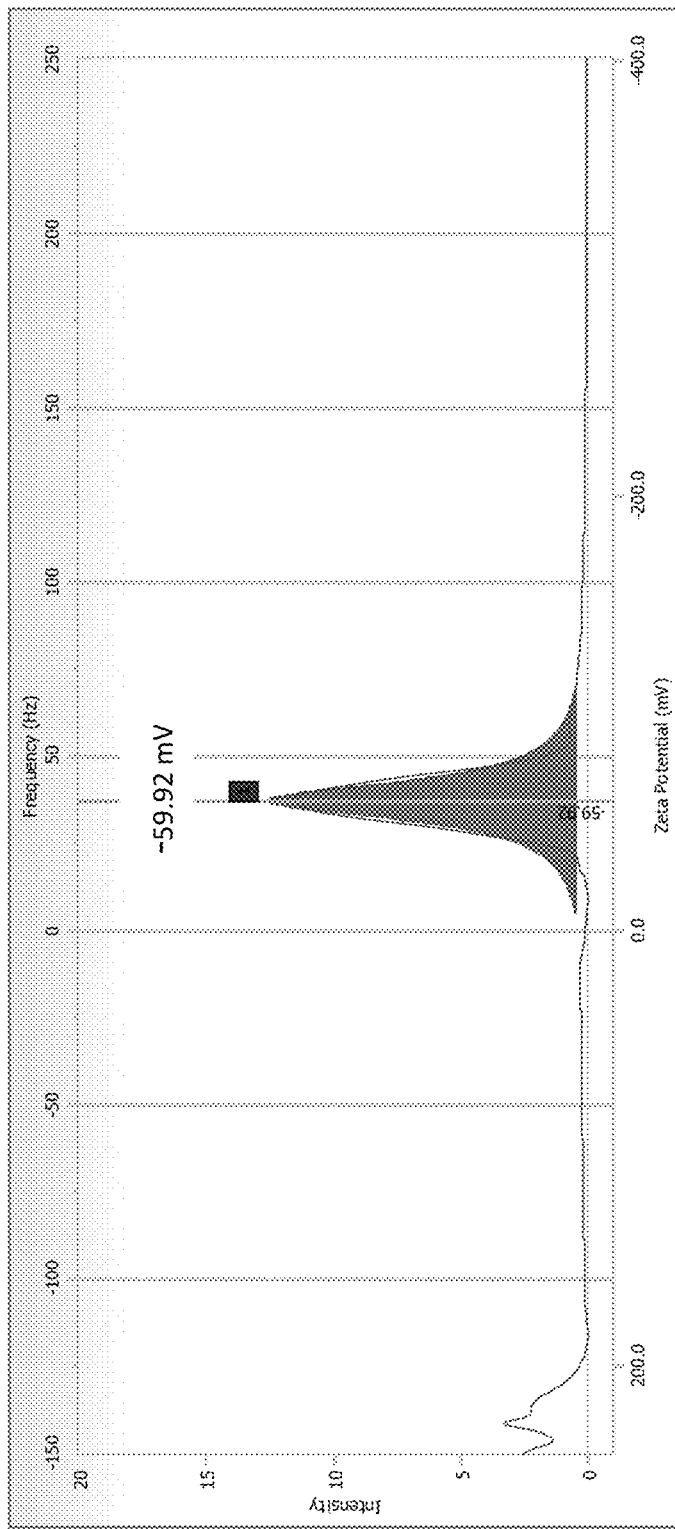
FIG. 20 depicts the mobility distribution for zeta potential for a lot of AB-101 hydrogel.

As shown in Table F, the deflocculants used are: sodium phosphate dibasic heptahydrate, sodium phosphate monobasic anhydrous and sodium hexametaphosphate. These deflocculants release negatively-charged phosphate groups that act by electrostatically stabilizing the particles where they are adsorbed on the surface of AB-101 and therefore increasing the zeta potential. This causes the particles to repulse each other and hence minimize coagulation and flocculation. The first two deflocculants (sodium phosphate dibasic heptahydrate and sodium phosphate monobasic anhydrous) belong to the phosphate family of deflocculants where they provide immediate electrostatic stabilization by dissociation into an immediate charged anion. Sodium hexametaphosphate is a long chain polyphosphate that dissociates over time or when exposed to higher temperatures to release phosphate groups which provides long term electrostatic stabilization. FIG. 20 depicts the zeta potential measurement of hydrogel formula of Table F. Phosphates and hexametaphosphate raise the pH of the hydrogel to near neutral (6) which is ideal for dermal wound healing applications.

Improved stability can be seen by comparing the zeta potential from the pharmaceutical AB-101 extract in FIG. 19 to the zeta potential of the AB-101 hydrogel formula of Table F as shown in FIG. 20.

The zeta potential for AB-101 hydrogel of Table F containing deflocculants shown in FIG. 20 is −59.92 mV. This represents a significant improvement versus the 8.93 mV zeta potential of the pharmaceutical AB-101 extract. Table 15 characterizes the properties of AB-101 hydrogel as exhibiting "good stability" behavior. This hydrogel formula would result in a formula that would meet FDA requirements to deliver reliable drug delivery.

The invention claimed is:

1. A hydrogel formulation comprising:
    filtered latex of *Croton lechleri*, glycerin, methylparaben, propylparaben, water, sodium phosphate dibasic heptahydrate, sodium phosphate monobasic, sodium hexametaphosphate, medium chain triglycerides, acrylamide, sodium acryloyldimethyl taurate copolymer, isohexadecane, and polysorbate 80;
    wherein the *Croton lechleri* contains at least about 110 PPM of Gallocatechin, at least about 780 PPM of Epigallocatechin, at least about 1.6 PPM of Catechin, at least about 2 PPM of Epicatechin, at least about 45 PPM Taspine, at least about 0.1 PPM of dimethylcedrusin and wherein the *Croton lechleri* has a polydispersity index of about 0.5 to about 0.85.

2. The hydrogel formulation of claim 1, wherein the filtered latex of *Croton lechleri* is filtered latex of *Croton lechleri* Müll.Arg.

3. The hydrogel formulation of claim 1, wherein the filtered latex of *Croton lechleri* is in an amount of about 5 wt % to about 80 wt %.

4. The hydrogel formulation of claim 1, wherein the glycerin is in an amount of about 1 wt % to about 5 wt %.

5. The hydrogel formulation of claim 1, wherein the methylparaben is in an amount of about 0.05 wt % to about 0.5 wt %.

6. The hydrogel formulation of claim 1, wherein the propylparaben is in an amount of about 0.005 wt % to about 0.05 wt %.

7. The hydrogel formulation of claim 1, wherein the water is in an amount of about 20 wt % to about 80 wt %.

8. The hydrogel formulation of claim 1, wherein the sodium phosphate dibasic heptahydrate is in an amount of about 1 wt % to about 3 wt %.

9. The hydrogel formulation of claim 1, wherein the sodium phosphate monobasic is in an amount of about 0.1 wt % to about 0.4 wt %.

10. The hydrogel formulation of claim 1, wherein the sodium hexametaphosphate is in an amount of about 0.005 wt % to about 0.02 wt %.

11. The hydrogel formulation of claim 1, wherein the medium chain triglycerides are in an amount of about 1 wt % to about 6 wt %.

12. The hydrogel formulation of claim 1, wherein the acrylamide, sodium acryloyldimethyl taurate copolymer, isohexadecane, and polysorbate 80 is in an amount of about 0.5 wt % to about 10 wt %.

13. The hydrogel formulation of claim 1, wherein the hydrogel formulation has a pH of about 3.0 to about 7.0.

14. A method of treating a dermatological condition in a subject in need thereof comprising topically administering to the subject a therapeutically effective amount of the hydrogel formulation of claim 1, wherein said treating is selected from alleviating symptoms of said dermatological condition, diminishing the extent of said dermatological condition, stabilizing the state of said dermatological condition, slowing the progression of said dermatological condition, ameliorating said dermatological condition, achieving remission of said dermatological condition, improving said dermatological condition and combinations thereof; wherein the dermatological condition is selected from the group consisting of atopic dermatitis, epidermolysis bullosa, impetigo, psoriasis, wounds, skin colonized with a pathogen, and combinations thereof.

15. The method of claim 14 wherein the pathogen is selected from the group consisting of *Staphylococcus aureus*, methicillin-resistant *Staphylococcus aureus* (MRSA), mupirocin-resistant MRSA, and combinations thereof.

16. The method of claim 14, wherein the administration is until the dermatological condition is treated.

17. The method of claim 14, wherein the topical administration is directly to the dermatological condition.

18. The hydrogel formulation of claim 1, wherein the filtered latex of *Croton lechleri* is in an amount of about 40 wt %.

19. The method of claim 14, wherein the subject has atopic dermatitis with an infection selected from a *Staphylococcus aureus* infection, a methicillin-resistant *Staphylococcus aureus* (MRSA) infection, a mupirocin resistant MRSA infection, and combinations thereof.

20. The method of claim 14, wherein the subject has epidermolysis bullosa with an infection selected from a *Staphylococcus aureus* infection, a methicillin-resistant *Staphylococcus aureus* (MRSA) infection, a mupirocin resistant MRSA infection, a *Streptococcus pyogenes* infection, a *Pseudomonas aeruginosa* infection, and combinations thereof.

21. The method of claim 14, wherein the subject has impetigo with an infection selected from a *Staphylococcus aureus* infection, a methicillin-resistant *Staphylococcus aureus* (MRSA) infection, a mupirocin resistant MRSA infection, a *Streptococcus pyogenes* infection, and combinations thereof.

22. The method of claim 14, wherein the subject has psoriasis with an infection selected from a *Staphylococcus aureus* infection, a methicillin-resistant *Staphylococcus aureus* (MRSA) infection, a mupirocin resistant MRSA infection, and combinations thereof.

23. The method of claim 14, wherein the subject has wounds with an infection selected from a *Staphylococcus aureus* infection, a methicillin-resistant *Staphylococcus aureus* (MRSA) infection, a mupirocin resistant MRSA infection, a *Streptococcus pyogenes* infection, a *Pseudomonas aeruginosa* infection, and combinations thereof.

24. A hydrogel formulation comprising:
filtered latex of *Croton lechleri*, glycerin, methylparaben, propylparaben, water, sodium phosphate dibasic heptahydrate, sodium phosphate monobasic, sodium hexametaphosphate, medium chain triglycerides, acrylamide, sodium acryloyldimethyl taurate copolymer, isohexadecane, and polysorbate 80;
wherein the *Croton lechleri* contains Gallocatechin, Epigallocatechin, Catechin, and Epicatechin.

25. The hydrogel formulation of claim 24, wherein the filtered latex of *Croton lechleri* is filtered latex of *Croton lechleri* Müll.Arg.

26. The hydrogel formulation of claim 24, wherein the filtered latex of *Croton lechleri* is in an amount of about 5 wt % to about 80 wt %.

27. The hydrogel formulation of claim 24, wherein the filtered latex of *Croton lechleri* is in an amount of about 40 wt %.

28. The hydrogel formulation of claim 24, wherein the glycerin is in an amount of about 1 wt % to about 5 wt %.

29. The hydrogel formulation of claim 24, wherein the methylparaben is in an amount of about 0.05 wt % to about 0.5 wt %.

30. The hydrogel formulation of claim 24, wherein the propylparaben is in an amount of about 0.005 wt % to about 0.05 wt %.

31. The hydrogel formulation of claim 24, wherein the water is in an amount of about 20 wt % to about 80 wt %.

32. The hydrogel formulation of claim 24, wherein the sodium phosphate dibasic heptahydrate is in an amount of about 1 wt % to about 3 wt %.

33. The hydrogel formulation of claim 24, wherein the sodium phosphate monobasic is in an amount of about 0.1 wt % to about 0.4 wt %.

34. The hydrogel formulation of claim 24, wherein the sodium hexametaphosphate is in an amount of about 0.005 wt % to about 0.02 wt %.

35. The hydrogel formulation of claim 24, wherein the medium chain triglycerides are in an amount of about 1 wt % to about 6 wt %.

36. The hydrogel formulation of claim 24, wherein the acrylamide, sodium acryloyldimethyl taurate copolymer, isohexadecane, and polysorbate 80 is in an amount of about 0.5 wt % to about 10 wt %.

37. The hydrogel formulation of claim 24, wherein the hydrogel formulation has a pH of about 3.0 to about 7.0.

38. A method of treating a dermatological condition in a subject in need thereof comprising topically administering to the subject a therapeutically effective amount of the hydrogel formulation of claim 24, wherein said treating is selected from alleviating symptoms of said dermatological condition, diminishing the extent of said dermatological condition, stabilizing the state of said dermatological condition, slowing the progression of said dermatological condition, ameliorating said dermatological condition, achieving remission of said dermatological condition, improving said dermatological condition and combinations thereof; and wherein the dermatological condition is selected from the group consisting of atopic dermatitis, epidermolysis bullosa, impetigo, psoriasis, wounds, skin colonized with a pathogen, and combinations thereof.

39. The method of claim 38, wherein the subject has atopic dermatitis with an infection selected from a *Staphylococcus aureus* infection, a methicillin-resistant *Staphylococcus aureus* (MRSA) infection, a mupirocin resistant MRSA infection, and combinations thereof.

40. The method of claim 38, wherein the subject has epidermolysis bullosa with an infection selected from a *Staphylococcus aureus* infection, a methicillin-resistant *Staphylococcus aureus* (MRSA) infection, a mupirocin resistant MRSA infection, a *Streptococcus pyogenes* infection, a *Pseudomonas aeruginosa* infection, and combinations thereof.

41. The method of claim 38, wherein the subject has impetigo with an infection selected from a *Staphylococcus aureus* infection, a methicillin-resistant *Staphylococcus aureus* (MRSA) infection, a mupirocin resistant MRSA infection, a *Streptococcus pyogenes* infection, and combinations thereof.

42. The method of claim 38, wherein the subject has psoriasis with an infection selected from a *Staphylococcus aureus* infection, a methicillin-resistant *Staphylococcus*

*aureus* (MRSA) infection, a mupirocin resistant MRSA infection, and combinations thereof.

43. The method of claim 38, wherein the subject has wounds with an infection selected from a *Staphylococcus aureus* infection, a methicillin-resistant *Staphylococcus aureus* (MRSA) infection, a mupirocin resistant MRSA infection, a *Streptococcus pyogenes* infection, a *Pseudomonas aeruginosa* infection, and combinations thereof.

44. The method of claim 38, wherein the administration is until the dermatological condition is treated.

45. The method of claim 38, wherein the topical administration is directly to the dermatological condition.

46. A hydrogel formulation comprising:
   about 5 wt % to about 80 wt % filtered latex of *Croton lechleri* Müll.Arg, about 1 wt % to about 5 wt % glycerin, about 0.05 wt % to about 0.5 wt % methylparaben, about 0.005 wt % to about 0.05 wt % propylparaben, about 20 wt % to about 80 wt % water, about 1 wt % to about 3 wt % sodium phosphate dibasic heptahydrate, about 0.1 wt % to about 0.4 wt % sodium phosphate monobasic, about 0.005 wt % to about 0.02 wt % sodium hexametaphosphate, about 1 wt % to about 6 wt % medium chain triglycerides, about about 0.5 wt % to about 10 wt % of a combination of acrylamide, sodium acryloyldimethyl taurate copolymer, isohexadecane, and polysorbate 80; and
   wherein the hydrogel formulation has a pH of about 3.0 to about 7.0.

47. The hydrogel formulation of claim 46, wherein the filtered latex of *Croton lechleri* is in an amount of about 40 wt %.

48. A method of treating a dermatological condition in a subject in need thereof comprising topically administering to the subject a therapeutically effective amount of the hydrogel formulation of claim 46, wherein said treating is selected from alleviating symptoms of said dermatological condition, diminishing the extent of said dermatological condition, stabilizing the state of said dermatological condition, slowing the progression of said dermatological condition, ameliorating said dermatological condition, achieving remission of said dermatological condition, improving said dermatological condition and combinations thereof; and wherein the dermatological condition is selected from the group consisting of atopic dermatitis, epidermolysis bullosa, impetigo, psoriasis, wounds, skin colonized with a pathogen, and combinations thereof.

49. The method of claim 48, wherein the subject has atopic dermatitis with an infection selected from a *Staphylococcus aureus* infection, a methicillin-resistant *Staphylococcus aureus* (MRSA) infection, a mupirocin resistant MRSA infection, and combinations thereof.

50. The method of claim 48, wherein the subject has epidermolysis bullosa with an infection selected from a *Staphylococcus aureus* infection, a methicillin-resistant *Staphylococcus aureus* (MRSA) infection, a mupirocin resistant MRSA infection, a *Streptococcus pyogenes* infection, a *Pseudomonas aeruginosa* infection, and combinations thereof.

51. The method of claim 48, wherein the subject has impetigo with an infection selected from a *Staphylococcus aureus* infection, a methicillin-resistant *Staphylococcus aureus* (MRSA) infection, a mupirocin resistant MRSA infection, a *Streptococcus pyogenes* infection, and combinations thereof.

52. The method of claim 48, wherein the subject has psoriasis with an infection selected from a *Staphylococcus aureus* infection, a methicillin-resistant *Staphylococcus aureus* (MRSA) infection, a mupirocin resistant MRSA infection, and combinations thereof.

53. The method of claim 48, wherein the subject has wounds with an infection selected from a *Staphylococcus aureus* infection, a methicillin-resistant *Staphylococcus aureus* (MRSA) infection, a mupirocin resistant MRSA infection, a *Streptococcus pyogenes* infection, a *Pseudomonas aeruginosa* infection, and combinations thereof.

54. The method of claim 48, wherein the administration is until the dermatological condition is treated.

55. The method of claim 48, wherein the topical administration is directly to the dermatological condition.

56. The method of claim 48, wherein the filtered latex of *Croton lechleri* is in an amount of about 40 wt % of the hydrogel formulation.

* * * * *